(12) United States Patent
Bilgicer et al.

(10) Patent No.: US 10,342,846 B2
(45) Date of Patent: Jul. 9, 2019

(54) NANOPARTICLE DRUG DELIVERY SYSTEMS

(71) Applicant: University of Notre Dame du Lac, South Bend, IN (US)

(72) Inventors: Zihni Basar Bilgicer, Granger, IN (US); Jonathan Ashley, South Bend, IN (US); Tanyel Kiziltepe Bilgicer, Granger, IN (US); Jared Stefanick, Mishawaka, IN (US); Nathan J. Alves, South Bend, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 43 days.

(21) Appl. No.: 14/765,620

(22) PCT Filed: Feb. 4, 2014

(86) PCT No.: PCT/US2014/014727
§ 371 (c)(1),
(2) Date: Aug. 4, 2015

(87) PCT Pub. No.: WO2014/121291
PCT Pub. Date: Aug. 7, 2014

(65) Prior Publication Data
US 2016/0038607 A1 Feb. 11, 2016

Related U.S. Application Data

(60) Provisional application No. 61/849,858, filed on Feb. 4, 2013, provisional application No. 61/849,869, filed on Feb. 4, 2013.

(51) Int. Cl.
| | | |
|---|---|---|
| *A61K 47/69* | (2017.01) | |
| *A61K 38/07* | (2006.01) | |
| *A61K 9/127* | (2006.01) | |
| *A61K 9/48* | (2006.01) | |
| *A61K 38/05* | (2006.01) | |
| *A61K 47/54* | (2017.01) | |
| *A61K 47/62* | (2017.01) | |
| *A61K 9/00* | (2006.01) | |
| *A61K 9/20* | (2006.01) | |

(52) U.S. Cl.
CPC .......... *A61K 38/07* (2013.01); *A61K 9/1271* (2013.01); *A61K 9/4858* (2013.01); *A61K 38/05* (2013.01); *A61K 47/542* (2017.08); *A61K 47/62* (2017.08); *A61K 47/6911* (2017.08); *A61K 9/008* (2013.01); *A61K 9/0014* (2013.01); *A61K 9/0019* (2013.01); *A61K 9/2054* (2013.01)

(58) Field of Classification Search
None
See application file for complete search history.

(56) References Cited

U.S. PATENT DOCUMENTS

| | | | | |
|---|---|---|---|---|
| 7,153,933 | B2 * | 12/2006 | Wu ..................... | A61K 9/1271 530/334 |
| 7,179,785 | B2 * | 2/2007 | Greene ................. | C07K 16/32 424/1.69 |
| 8,236,330 | B2 | 8/2012 | Zale et al. | |
| 8,246,968 | B2 | 8/2012 | Zale et al. | |
| 8,367,113 | B2 | 2/2013 | Gu et al. | |
| 2011/0033468 | A1 | 2/2011 | Shih et al. | |
| 2011/0104258 | A1 | 5/2011 | Pit et al. | |
| 2011/0171666 | A1 * | 7/2011 | Weinberg ............... | C07F 9/091 435/7.25 |
| 2011/0244048 | A1 | 10/2011 | Amiji et al. | |
| 2015/0152140 | A1 * | 6/2015 | Sorensen ................ | C07K 7/08 424/186.1 |

FOREIGN PATENT DOCUMENTS

| | | |
|---|---|---|
| WO | 2007016542 A2 | 2/2007 |
| WO | 2009031859 A2 | 3/2009 |
| WO | 2011112999 A2 | 9/2011 |
| WO | 2013067537 A1 | 5/2013 |

OTHER PUBLICATIONS

Takeoka, S., et al., J. Am. Chem. Soc. 122: 7927-7935, 2000.*
Fee et al (European Pharmaceutical Review, Feb. 2010, issue 1, 23 pages).*
Reynolds et al (Toxicology and Applied Pharmacology, 2012, 262:1-10, IDS).*
Takeoka (Takeoka, S., et al., J. Am. Chem. Soc. 122: 7927-7935, 2000).*
Kiziltepe et al (Blood Cancer Journal, 2012, 2:e64; published online Apr. 20, 2012, IDS).*
Watanabe et al (International Journal of Nanomedicine, 2012, 7:3679-3688).*
Kim et al (Langmuir, 2005, 21:8852-8857).*
European Patent Office, "Extended European Search Report for European Patent Application No. 14746863.1", dated Aug. 19, 2016; 8 pgs.

(Continued)

*Primary Examiner* — Laura B Goddard
(74) *Attorney, Agent, or Firm* — Haukaas Fortius PLLC; Michael H. Haukaas

(57) ABSTRACT

The invention provides pharmaceutical compositions and method of using the compositions, wherein the compositions comprise liposomes or micelles that contain one or more targeting peptides and/or anticancer drugs. In various embodiments, the components of the liposomes can include a) a phospholipid and optionally a lipid that is not a phospholipid; b) a pegylated lipid; c) a peptide-ethylene glycol (EG)-lipid conjugate wherein the peptide is a targeting ligand, and d) one or more drug-conjugated lipid, encapsulated drugs, or a combination thereof. The peptide-EG-lipid conjugate can be, for example, a compound of Formula (I) or Formula (II). The ethylene glycol (EG) segments of the peptide-EG-lipid conjugate can be, for example, EG6 to about EG36; and the EG segment can be conjugated to one or more lysine moieties.

24 Claims, 33 Drawing Sheets
Specification includes a Sequence Listing.

(56) References Cited

OTHER PUBLICATIONS

Zhaohui et al., "The Use of a Tumor Metastasis Targeting Peptide to Deliver Doxorubicin-Containing Liposomes to Highly Metastatic Cancer", Biomaterials, vol. 33, No. 33; Aug. 31, 2012; pp. 8451-8460; Elsevier Ltd.
International Search Report dated Aug. 28, 2014; Application No. PCT/US14/14727, filed Feb. 4, 2014.
Kiziltepe, T. et al., "Rationally engineered nanoparticles target multiple myeloma cells, overcome cell-adhesion-mediated drug resistance, and show enhanced efficacy in vivo," Blood Cancer Journal, 2012, 10 pages, 2.
Noble, Gavin T. et al., "Ligand-targeted liposome design: challenges and fundamental considerations," Trends in Biotechnology, 2014, 32-45, 32.
Reynolds, Joseph G. et al., "HER2-targeted liposomal doxorubicin displays enhanced anti-tumorigenic effects without associated cardiotoxicity," Toxicology and Applied Pharmacology, 2012, 1-10, 262.
Stefanick, Jared F. et al., "A Systematic Analysis of Peptide Linker Length and Liposomal Polyethylene Glycol Coating on Cellular Uptake of Peptide-Targeted Liposomes," ACS Nano, 2013, 2935-2947, 7.
Stefanick, Jared F. et al., "Enhanced Cellular Uptake of Peptide-Targeted Nanoparticles through Increased Peptide Hydrophilicity and Optimized Ethylene Glycol Peptide-Linker Length," ACS Nano, 2013, 8115-8129, 7.
Written Opinion dated Aug. 28, 2014; Application No. PCT/US14/14727, filed Feb. 4, 2014.
Xiao, Haihua et al., "Micellar nanoparticle formation via electrostatic interactions for delivering multinuclear platinum (II) drugs," Chemical Communications, 2013, 4809-4811, 49.
Xiao, Haihua et al., "Photosensitive Pt(IV)-azide prodrug-loaded nanoparticles exhibit controlled drug release and enhanced efficacy in vivo," Journal of Controlled Release, 2014, 11-17, 173.

\* cited by examiner

| Receptor | Ligand | PEG coating | PEG linker length | Liposome diameter | Diagnostic/therapeutic agent | Cancer cell type | Outcome (effect of targeting) |
|---|---|---|---|---|---|---|---|
| α4b1 | Peptide | 350 | EG12 | 100 nm | Fluorescein/rhodamine | Human multiple myeloma (NCI-H929) | 100-fold enhancement in cellular uptake with PEG350 coating/EG12 linker compared to non-targeted control in vitro. Negligible uptake observed for traditional formulations of PEG2000 coating and linker |
| αvb3 | RGD peptide | 2000 | 2000 | 90 nm | Combretastatin/doxorubicin | Murine melanoma (B16, B16F10) | Twofold decrease in IC50 values compared to non-targeted liposomes in vitro |
| αvb3 | RGD peptide | 2000 | 2000 | 100 nm | Doxorubicin | Murine colon carcinoma (C26) | Ligand targeted liposomes enhanced tumor growth inhibition, despite equal tumor biodistribution, compared to non-targeted controls in vivo |
| αvb3 | RGD peptide | 2000 | 2000 | 116 nm | Paclitaxel | Human ovarian (SKOV-3) | Enhanced cellular uptake and threefold reduction in IC50 in vitro compared to non-targeted controls. Modest enhancement in tumor growth inhibition in vivo |
| αvb3 | RGD peptide | Not specified | 88/264 | 76 nm | Doxorubicin | Murine colon carcinoma (C26) | Increased tumor growth inhibition in vivo compared with non-targeted controls and free doxorubicin |
| αvb3 | RGD peptide | 2000 | None | 99 nm | None | Human lung carcinoma (A549) | Fourfold enhancement in tumor biodistribution compared to non-targeted liposomes in vivo |
| ASGPR | Lactose | 2000 | None | 96 nm | Doxorubicin | Human liver (HepG2) | Enhanced intracellular uptake fourfold over non-targeted control in vitro. Enhanced tumor biodistribution, tumor growth inhibition and mean survival time in vivo compared to non-targeted control |
| CD19 | mAb, scFv, Fab | 2000 | 2000 | 100 nm | Doxorubicin | Human B-cell lymphoma (Raji) | Reduced IC50; fivefold over non-targeted control in vitro. Significantly extended survival times in vivo compared to non-targeted control and free doxorubicin |
| CD19, CD20 | mAb | 2000 | 2000 | 100 nm | Doxorubicin/vincristine | Human B-cell lymphoma (Namalwa) | Enhanced mean survival time in vivo compared to non-targeted controls. Co-delivery of CD19 and CD20-targeted liposomes showed further increases in survival time |
| CD19 | mAb | 2000 | 2000 | 110 nm | Doxorubicin | Human B-cell lymphoma (Namalwa) | Enhanced intracellular uptake threefold, and four- to sixfold reduction in IC50 over non-targeted control in vitro. Increased survival time in vivo |
| CD19, CD20 | mAb | 2000 | 2000 | 100 nm | Doxorubicin | Human B-cell lymphoma (Namalwa) | Enhanced binding and uptake, and tenfold reduction in IC50 in vitro compared to non-targeted controls. Dual-targeting provided further enhancements |

*Figure 36*

| Receptor | Ligand | PEG coating | PEG linker length | Liposome diameter | Diagnostic/therapeutic agent | Cancer cell type | Outcome (effect of targeting) |
|---|---|---|---|---|---|---|---|
| CD19 | mAb | 2000 | 2000 | 120 nm | Doxorubicin | Human B-cell lymphoma (Namalwa) | Two- to 30-fold reduction in $IC_{50}$ in vitro compared to non-targeted controls. pH-triggered release gave modest improvements in vitro and in vivo |
| CD20, HER2 | mAb | 2000 | 2000 | 110 nm | Trastuzumab, rituximab | Human breast (MCF7, LCC6), human Burkitt's lymphoma (Ramos) | Up to 25-fold increase in antibody potency in vitro compared with free drug. Enhanced tumor reduction in vivo compared with free drug |
| Receptor | Ligand | PEG coating | PEG linker length | Liposome diameter | Diagnostic/therapeutic agent | Cancer cell type | Outcome (effect of targeting) |
| CD20 | mAb | 2000 | 2000 | 56 nm | siRNA (Bcl-2) | Human B-cell lymphoma (Raji) | Immunoliposomes exhibited efficient delivery of the oligonucleotide in vivo and induced apoptosis with diminished immunostimulatory |
| Folic acid receptor | Folate | None | None/3350 | 66 nm | Calcein | Human cervical (KB) | Cellular uptake of folate-targeted liposomes modified with PEG3350 linker increased by rv37- fold over folate-targeted liposomes with |
| Folic acid receptor | Folate | None/2000 | 2000/3350 | 70–90 nm | 3H-cholesteryl hexadecyl ether | Murine lung carcinoma (M109), human cervical (KB) | Use of a PEG3350 linker enhanced cellular binding by rvfourfold over the use of PEG2000 linker in vitro |
| Folic acid receptor | Folate | 2000 | 2000/3400/5000 | 100 nm | Doxorubicin | Murine lung carcinoma (M109), human cervical (KB) | LTLs with sufficiently long PEG spacers (5000) enhanced tumor inhibition in vivo compared to non-targeted controls |
| Folic acid receptor | Folate | 2000 | 3350 | 70–90 nm | Doxorubicin | Human cervical (KB), murine lymphoma (J6456) | Significant enhancements in tumor growth inhibition and mean survival time compared to non-targeted controls in vivo |
| Glucose transporter | Glucose | None | 200/400/1000/2000 | 100 nm | DiR | Blood–brain barrier model | PEG400, 1000, and 2000 linkers achieved greatest brain targeting in vitro, with PEG1000 proving optimal in vivo |
| GRPR | Peptide (bombesin) | None | EG28 | 146–165 nm | Doxorubicin | Human prostate (PC-3) | Enhanced tumor growth inhibition (60%) compared to non-targeted liposomes (36%) in vivo |
| HER2 | Fab | 2000 | None/2000 | 70–100 nm | HPTS/Rhodamine | Human breast (SK-BR-3, BT-474) | LTLs with Fabs conjugated to PEG2000 linker demonstrated increased cellular binding and internalization compared to Fabs with no linker |
| HER2 | mAb, Fab, scFv | 2000 | 2000 | 90–110 nm | Doxorubicin | Human breast (BT-474, MCF7, MDA-MB-453) | Superior antitumor efficacy in vivo, with overall cure rates of 16% compared to no cures for free or non-targeted liposomal doxorubicin |
| HER2 | Fab, scFv | 2000 | 2000 | 90–110 nm | Colloidal goal/cyanine dye | Human breast (BT-474) | Enhanced intracellular uptake of targeted liposomes by up to rvsixfold compared to non-targeted liposomes in vivo, despite similar |
| HER2 | mAb | 2000 | 2000 | <200 nm | Paclitaxel | Human breast (BT-474, SK-BR-3) | Enhanced antitumor efficacy compared to non-targeted and free drug in vivo |

*Figure 36 (cont.)*

| Target | Ligand | PEG1 | PEG2 | Size | Drug | Cancer type | Results |
|---|---|---|---|---|---|---|---|
| HER2 | scFv | 2000 | | Not specified | Doxorubicin | Human breast (BT-474, SK-BR-3) | Enhanced in vivo tumor uptake r/v twofold and r/v20-fold compared to non-targeted liposomes and free drug, respectively |
| HER2 | Peptide | 2000 | | 108 nm | Doxorubicin | Human breast (BT-474) | pH-responsive lipids unmask HER2 targeting peptide at tumor site, decreasing tumor volume by 160% compared to non-targeted controls in |
| HER2 | Peptide | 350 | | EG6 – EG72 | Fluorescein/rhodamine | Human breast (BT-474, SK-BR-3) | Ninefold enhancement in cellular uptake with PEG350 coating/EG12 linker compared to non-targeted control in vitro. Negligible uptake |
| LHRH receptor | Peptide | 2000 | | 100 nm | Paclitaxel | Human small lung carcinoma (H69), non-small lung carcinoma (A549) | 50% enhancement in uptake and tenfold reduction in $IC_{50}$ over non-targeted control In vitro. Reduced liver toxicity and significant reduction in tumor volume (2.5-fold) in vivo compared to non-targeted control (20% increase) |
| LHRH receptor | Peptide | 2000 | | 120–150 nm | Mitoxantrone | Human breast (MCF-7), human ovarian (SK-OV-3) | Enhanced uptake and 20-fold reduction in $IC_{50}$ compared to non-targeted controls in vitro |
| PSMA | Folate | 2000 | | 104–207 nm | Luciferase-encoding plasmid DNA (pCMV-Luc) | Human prostate (LNCaP) | Ninefold enhancement in luciferase production after transfection compared to non-targeted controls in vitro |
| PSMA | mAb | 2000 | | 3400 | 200 nm | Doxorubicin | Human prostate (LNCaP, PC-3, DU145), human non-small lung carcinoma (A549) | Enhanced cytotoxicity over non-targeted control in vitro |
| SSTR2 | Peptide (octreotide) | 2000 | | 86–94 nm | Doxorubicin | Human small cell lung carcinoma (NCI-H446) | Twofold enhancement in intracellular uptake and two- to threefold reduction in $IC_{50}$ compared to non-targeted controls in vitro. Enhanced drug accumulation in tumor and improved cancer efficacy despite decreased circulation in vivo relative to non-targeted liposomes |
| SSTR2 | Peptide (octreotide) | None | | 3400 | 134–154 nm | Irinotecan | Human thyroid medullary carcinoma (TT) | Enhanced in vitro $IC_{50}$ compared to free drug and non-targeted controls. In vivo median survival increased for targeted versus non-targeted from 103 to 217 days |
| Transferrin receptor | Transferrin | 1000 | | 2000 | 115 nm | Ceramide | Human ovarian (A2780) | Twofold reduction in $IC_{50}$ in vitro, and twofold reduction in tumor volume in vivo over non-targeted control |
| Transferrin receptor | Holo-transferrin | Not specified | | 129 nm | Cisplatin | Human cisplatin-resistant ovarian carcinoma (A2780cis) | Enhanced Pt uptake into drug resistant cells and twofold enhancement in $IC_{50}$ in vitro over non-targeted control |
| Transferrin receptor | Holo-transferrin | 2000 | | 2000 | 175.5 nm | siRNA (anti-BCR-ABL) | Human leukemia (K562, LAMA-84) | Selective delivery of siRNA into cells in vitro with no siRNA delivered by non-targeted control |

*Figure 36 (cont.)*

| | | | | | | |
|---|---|---|---|---|---|---|
| Transferrin receptor | Transferrin | Not specified | Not specified | 180-200 nm | Cisplatin | Human gastric cancer (MKN45) | Up to eightfold enhancement of in vitro intracellular uptake and twofold enhancement in tumor uptake in vivo over non-targeted controls. Significant extension in mean survival time compared to non-targeted control |
| Transferrin receptor | Holo-transferrin | 3000 | 2000 | 125-195 nm | siRNA (Bcl2) | Human leukemia (K562) | 50% downregulation of Bcl-2 protein with 100 nM siRNA in K562 cells and 8% for free siRNA in vitro. Twofold reduction in IC$_{50}$ of doxorubicin compared to non-targeted control |
| Transferrin receptor | Holo-transferrin | 2000 | 2000 | 141 nm | siRNA (Bcl-2) | Human leukemia (K562) | 3.5-fold enhancement in tumor uptake over free siRNA in vivo. Improves tumor growth inhibition and extended mean survival time over non-targeted controls |
| Transferrin receptor | Holo-transferrin | 2000 | 2000 | 70 nm | Doxorubicin | Human hepatocellular carcinoma (HepG2) | Fourfold reduction in IC$_{50}$ over non-targeted controls in vitro. Enhanced tumor biodistribution over non-targeted controls in vivo. Enhanced tumor growth inhibition versus free doxorubicin and non-targeted control |
| Transferrin receptor | Transferrin | 2000 | 3000 | 100 nm | Oxaliplatin | Mouse colon (C26) | 20% enhancement in tumor accumulation of Pt over non-targeted control in vivo. Tumor volume growth 10% versus 30% for non-targeted control |
| Transferrin receptor | Transferrin | 2000 | 2000 | 100 nm | Doxorubicin/verapamil | Human leukemia (K562) | Enhanced intracellular uptake and fivefold reduction in IC$_{50}$ in Dox-resistant cells in vitro compared to non-targeted controls |
| Transferrin receptor | Transferrin | None | None | 120 nm | Doxorubicin | Human small lung carcinoma (SBC-3) | Enhanced intracellular uptake and at least 30-fold reduction in IC$_{50}$ for drug resistant cell line in vitro |
| Transferrin receptor | scFv | None | None | 92.9 nm | Luciferase-encoding plasmid DNA (p53) | Human prostate (DU145), human breast (MDA-MB-435), human head and neck (DU145, JSQ-3) | Four- to tenfold enhancement in gene transcription in vitro compared to non-targeted controls. High level of plasmid expression in tumor with targeted liposome |

*Figure 36 (cont.)*

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Cyclic peptide

<400> SEQUENCE: 1

Tyr Cys Asp Gly Phe Tyr Ala Cys Tyr Met Asp Val
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Cyclic peptide

<400> SEQUENCE: 2

Tyr Cys Asp Pro Cys
1               5
```

NANOPARTICLE DRUG DELIVERY SYSTEMS

RELATED APPLICATIONS

This application is a National Stage filing under 35 U.S.C. § 371 of International Application No. PCT/US2014/014727, filed Feb. 4, 2014, which claims priority under 35 U.S.C. § 119(e) to U.S. Provisional Patent Application Nos. 61/849,858 and 61/849,869, both filed Feb. 4, 2013, which applications are incorporated herein by reference.

SEQUENCE LISTING

The instant application contains a Sequence Listing which has been submitted electronically in ASCII format and is hereby incorporated by reference in its entirety. Said ASCII copy, created on Sep. 17, 2015, is named 501.018US1_ST25.txt and is 693 bytes in size.

BACKGROUND OF THE INVENTION

Polyethylene glycol (PEG) coated liposomal nanoparticles of a defined size range of 100 to 200 nm are efficient drug delivery systems because they combine increased stability, high circulation times, increased tumor accumulation, and decreased systemic toxicity. Despite these particular advantages liposomal nanoparticles provide when compared to small molecule drugs, lack of selectivity for cancer cells still remains a major problem. An important feature of liposomal drug delivery nanoparticles is that they present particularly attractive scaffolds for the display of multiple functional groups on their surfaces. To overcome the selectivity problem, many researchers have taken the approach of active targeting by conjugating targeting ligands such as antibodies, antibody fragments, small molecules, and targeting peptides to improve the tumor targeting and cellular uptake of nanoparticle-based drug carriers. However, active targeting of nanoparticles has not consistently shown successful outcomes. At present, there is still an extensive debate on the relative contributions of active versus passive targeting in nanoparticle-based drug delivery systems. The apparent discrepancy observed in the field of targeted liposomal nanoparticles has in part been attributed to differences in type of tumor models. However, there is still a great amount of uncertainty regarding the source of the lack of consistent targeting outcomes.

Accordingly, there is a need for a nanoparticle drug delivery systems that can effectively target tumors and cancer cells for the delivery of active agents with reduced or eliminated systemic toxicity. There is also a need for novel nanoparticle drug delivery formulations and methods for delivering their drug cargo using pharmaceutically acceptable components that avoid immunogenic responses.

SUMMARY

The invention provides liposomal and micellar drug delivery systems that display enhanced cellular uptake compared to commonly used nanoparticles having longer PEG chains in their nanoparticle halos. The nanoparticles of the invention can be used to deliver a variety of therapeutic agents including encapsulated anticancer drugs and conjugated pro-drugs, such as proteasome inhibitors.

The invention therefore provides a pharmaceutical composition comprising liposomes or micelles that contain one or more anticancer drugs. In one embodiment, the liposomes comprise:

a) a phospholipid, and optionally a lipid that is not a phospholipid (such as cholesterol);
b) a pegylated lipid;
c) a peptide-ethylene glycol (EG)-lipid conjugate wherein the peptide is a targeting ligand, and
d) one or more drug-conjugated lipid, encapsulated drugs, or a combination thereof;

wherein the ethylene glycol (EG) segment of the peptide-EG-lipid conjugate is EG6 to about EG36; and the EG segment is conjugated to a lysine moiety wherein the conjugation comprises an amide linkage, and wherein the lysine moiety is conjugated to two $(C_{14}-C_{24})$acyl moieties through amide bonds.

The liposomes or micelles can include one or more different peptide-ethylene glycol (EG)-lipid conjugate (e.g., 2, 3, 4, or 5 different conjugates having different targeting ligands), for example, wherein the targeting ligand is different on one or more of the conjugates, to provide increased selectivity or affinity to various targets.

In one embodiment, the phospholipid is hydrogenated soy L-α-phosphatidylcholine (HSPC). In some embodiments, about 80 mol % to about 95 mol % of the liposome is a phospholipid.

In one embodiment, the lipid that is not a phospholipid is cholesterol. In some embodiments, about 5 mol % to about 15 mol %, or about 10 mol %, of the liposome is a lipid that is not a phospholipid.

In one embodiment, the pegylated lipid is PEG-DSPE. In some embodiments, about 2 mol % to about 10 mol % of the liposome is a pegylated lipid. In one embodiment, about 2 mol % to about 6 mol %, or about 5 mol %, or about 3 mol % of the molecules of the liposome are PEG350-lipids.

In one embodiment, the pegylated lipids have about 6 repeating PEG moieties to about 36 repeating PEG moieties. In other embodiments, the PEG portion of the pegylated lipids can any mass of a pegylated group described herein, for example, PEG-2000, or PEG-5000.

In one embodiment, about 0.1 mol % to about 6 mol %, about 1 mol % to about 6 mol %, or about 5 mol %, about 3 mol %, or about 2 mol % of the molecules of the liposome are peptide-EG-lipid conjugates.

In one embodiment, the peptide of the peptide-EG-lipid conjugate is HER2-pep (SEQ ID NO: 1).

In one embodiment, the peptide of the peptide-EG-lipid conjugate is VLA4-pep (SEQ ID NO: 2).

In one embodiment, the $(C_{14}-C_{24})$acyl moieties are palmitate moieties, or another fatty acid moiety of a fatty acid or fatty acid ester described herein.

In one embodiment, the components of the liposome comprise HSPC, cholesterol (CHOL), DSPE-PEG2000 or DSPE-PEG350, VLA4-pep, and an encapsulated free drug. In various embodiments, the components HSPC:CHOL:DSPE-PEG2000 or DSPE-PEG350:VLA4-pep are present in a ratio of about 95:10:3:2, wherein the term about refers to a variation of plus or minus 20%.

In one embodiment, the components of the liposome comprise HSPC, cholesterol (CHOL), DSPE-PEG2000 or DSPE-PEG350, HER2-pep, and an encapsulated free drug. In one specific embodiment, the components HSPC:CHOL:DSPE-PEG2000 or DSPE-PEG350:HER2-pep are present in a ratio of about 95:10:3:2, wherein the term about refers to a variation of plus or minus 20%.

In one embodiment, the peptide-EG-lipid conjugate comprises about 1 mol % to about 3 mol % of the molecules in the liposomes.

In one embodiment, the peptide-EG-lipid conjugate comprises about 2 mol % of the molecules in the liposomes.

In one embodiment, the pegylated lipid has a PEG moiety of PEG750 or greater and the peptide-EG-lipid conjugate comprises a hydrophilic oligolysine chain between the peptide and the EG moiety, wherein the oligolysine comprises 2, 3, 4, or 5 lysine units. In certain specific embodiments, the oligolysine comprises 3 lysine units, or 4 lysine units.

In one embodiment, the liposome further comprises an active targeting ligand conjugated to a lipid, wherein the targeting ligand is an antibody, an antibody fragment, or a small molecule.

In one embodiment, the diameter of the liposomes is about 30 nm to about 200 nm. In another embodiment, the diameter of the liposomes is about 30 nm to about 125 nm. In another embodiment, the diameter of the liposomes is about 75 nm to about 125 nm. In another embodiment, the diameter of the liposomes is about 30 nm to about 110 nm. In another embodiment, the diameter of the liposomes is about 90 nm to about 110 nm. In yet another embodiment, the diameter of the liposomes is about 30 nm to about 50 nm.

In various embodiments, micelles can be prepared using one or more of the same components as described for the liposomes herein. The diameter of the micelles can be about 10 nm to about 50 nm, or about 15 nm to about 35 nm, or about 20 nm to about 30 nm. The micelles can be prepared with similar mol % amounts of the various components described above for the liposomes.

In one embodiment, the peptide-ethylene glycol (EG)-lipid conjugate is a compound of Formula (I):

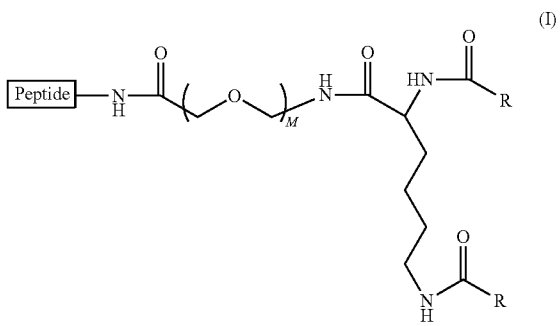

wherein
M is about 6 to about 36;
each R is independently a $(C_{13}$-$C_{23})$alkyl, wherein the alkyl is a straight chain or branched, saturated or partially unsaturated with one to three double bonds; and
Peptide is an amino acid chain, optionally cyclic, of 3 to about 50 amino acids; or an ion or salt thereof.

In another embodiment, the peptide-ethylene glycol (EG)-lipid conjugate is a compound of Formula (II):

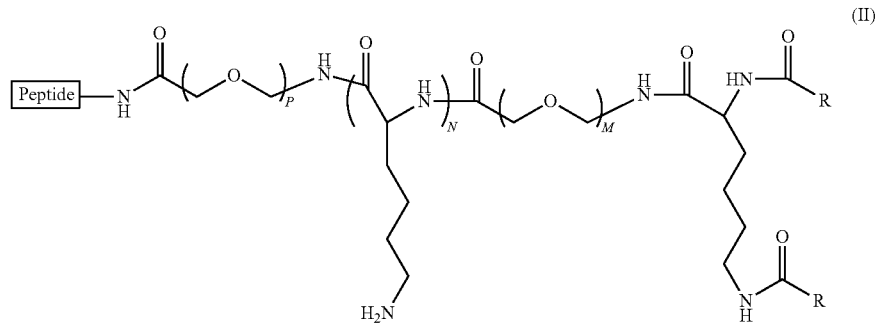

wherein
M is about 6 to about 36;
N is 2, 3, 4, 5, or 6;
P is 1-6;
each R is independently a $(C_{13}$-$C_{23})$alkyl, wherein the alkyl is a straight chain or branched, saturated or partially unsaturated with one to three double bonds; and
Peptide is an amino acid chain, optionally cyclic, of 3 to about 50 amino acids; or an ion or salt thereof.

With respect to the compounds of Formulas (I) and (II):
In various embodiments, M can be about 6, about 12, about 18, about 24, about 30, or about 36.

In various embodiments, R, in combination with carbonyl to which it is attached, can be any $(C_{14}$-$C_{24})$ fatty acid-derived moiety; such as the fatty acids described herein. In one specific embodiment, R is a straight-chain $(C_{15})$alkyl (i.e., R, in combination with carbonyl to which it is attached, is derived from palmitic acid).

In various embodiments, Peptide is HER2-pep. In some embodiments, Peptide is VLA4-pep. In additional embodiments, some compounds of the liposome or micelle include a Peptide where the Peptide is HER2-pep, and other compounds of the same liposome or micelle include a Peptide where the Peptide is VLA4-pep. Peptide can also be any other peptide described herein wherein the peptide can be conjugated to a compound of Formula (I) or (II). Thus, the micelles and liposomes can include a variety of combinations of compounds with different peptides conjugated to compounds in their components.

In some embodiments, Peptide is cyclic. In some embodiments, Peptide is linear. In certain embodiments, Peptide is branched. Peptide can include 3 to about 50 amino acids, for example, about 5 to about 50 amino acids, about 10 to about 50 amino acids, about 15 to about 50 amino acids, about 20 to about 50 amino acids, about 30 to about 50 amino acids, 3 to about 40 amino acids, 3 to about 30 amino acids, 3 to about 20 amino acids, 3 to about 15 amino acids, 5 to about 15 amino acids, or 5 to about 10 amino acids, or any range between any two of the aforementioned integers.

With respect to the compounds of Formula (II):
N can be 2-6. In one embodiment, N is 3. In another embodiment, N is 4.

P can be 2-6. In one embodiment, P is 2. In one embodiment, P is 3. In another embodiment, P is 4. In another embodiment, P is 5. In another embodiment, P is 6.

As would be readily recognized by one of skill in the art, the variables and elements of Formulas (I) and (II) can be varies for their specific cell targeting purpose, for example, so that Peptide is positioned near, at, or above the PEG coating of the liposome or micelle.

The liposomes or micelles described herein can have any combination of the components described above, including one or more different specific components, including one or more different compounds of Formula (I), one or more different compounds of Formula (II), or combinations thereof.

In one embodiment, the encapsulated drug comprises carfilzomib, an HDAC inhibitor, or another drug or active agent described herein, or combinations thereof. In various embodiments, the one or more drug-conjugated lipids can include bortezomib, doxorubicin; or another drug or active agent in the form of a drug-conjugated lipid described herein; a combination thereof. Of course, the liposomes or micelles may include combinations of various encapsulated drugs and various drug-conjugated lipids in their various compositions and formulations.

The invention further provides methods for delivering a drug to a cancer cell, in vitro or in vivo, for example, in a patient. The invention also provides methods for treating cancer in a patient. The methods can include contacting a cancer cell with a pharmaceutical composition described herein. The methods can also include administering to a subject in need of cancer therapy an effective amount of a pharmaceutical compositions described herein. The composition can include a drug-conjugated lipid or encapsulated drug, wherein the drug is effective for treating the cancer, and wherein the composition is taken up by cancer cells, for example, in the subject, and the composition releases the drug in the cancer cells. The cancer cells are thereby killed, or inhibited from growing, thereby treating the cancer.

In one embodiment, the cancer is breast cancer. The breast cancer cells can include Human Epidermal Growth Factor Receptor 2 (HER2) overexpressing breast cancer cells.

In another embodiment, the cancer is multiple myeloma. The multiple myeloma cells can include Very Late Antigen-4 (VLA-4) overexpressing multiple myeloma cancer cells.

The invention thus provides novel compositions as described herein, intermediates for the preparations of the compositions, as well as methods of preparing and purifying the compositions. The invention further provides for the use of the compositions described herein for use in medical therapy. The medical therapy can be treating cancer, for example, breast cancer, lung cancer, pancreatic cancer, prostate cancer, or colon cancer. The invention also provides for the use of a composition as described herein for the manufacture of a medicament to treat a disease in a mammal, for example, cancer cells or cancerous tumors in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 36. Summary of LTL characteristics and biological outcomes for commonly targeted receptors. Abbreviations: Fab, fragment antigen-binding; GRPR, gastrin-releasing peptide receptor; HER2, human epidermal growth factor receptor 2; $IC_{50}$, half-maximal inhibitory concentration; RGD, cyclic Arg-Gly-Asp peptide with neuropilin-1 binding motif; LHRH, luteinizing-hormone-releasing hormone; LTL, ligand-targeted liposome; mAb, monoclonal antibody; PEG, polyethylene glycol; PSMA, prostate-specific membrane antigen; scFv, single-chain variable fragment; siRNA, small interfering RNA; SSTR2, somatostatin receptor 2.

DETAILED DESCRIPTION

Figure 1:
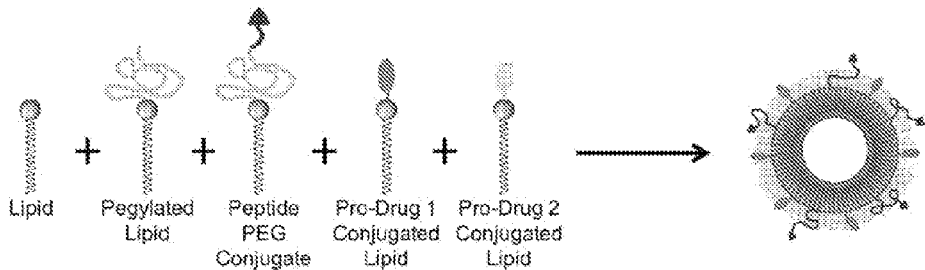
FIG. 1. A schematic representation of components of certain liposomes of the invention, according to one embodiment. One or more pro-drug conjugated lipids are optional in other embodiments, for example, when drugs are encapsulated in the liposomes.
Figure 2:
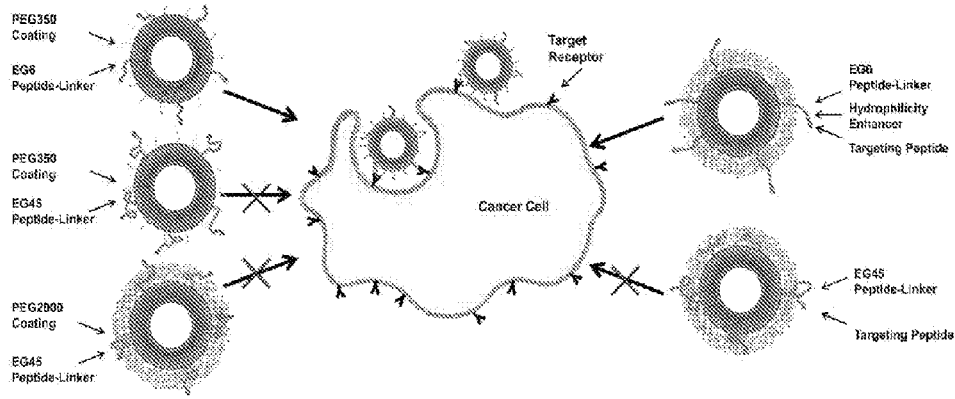
FIG. 2. A schematic representation of enhanced cellular update of shorter-length PEG-containing liposomes as described herein into a cancer cell, relative to the cellular uptake of standard PEG2000 coated liposomes and liposomes having EG45 peptide linkers.

PEGylated liposomes are attractive pharmaceutical nanocarriers. However, literature reports of ligand-targeted nanoparticles have not consistently shown successful drug delivery results. Described herein is a multifaceted synthetic strategy to prepare peptide-targeted liposomal and micellar nanoparticle drug delivery systems with high purity, reproducibility, and precisely controlled stoichiometry of functionalities. The roles of liposomal PEG coating, peptide EG-linker length, and peptide valency on cellular uptake are described and evaluated in a systematic manner. These parameters were analyzed in two distinct disease models where the liposomes were functionalized with either HER2- or VLA-4-antagonistic peptides to target HER2-overexpressing breast cancer cells or VLA-4-overexpressing myeloma cells, respectively. When targeting peptides were tethered to nanoparticles with an EG45 (~PEG2000) linker in a manner similar to a more traditional formulation, their cellular uptake was not enhanced compared to non-targeted versions regardless of the liposomal PEG coating used. Conversely, reduction of the liposomal PEG to PEG350 and the peptide linker to EG12 (~PEG530) dramatically enhanced cellular uptake by ~9-fold and ~100-fold in the breast cancer and multiple myeloma cells, respectively. Uptake efficiency reached a maximum and a plateau with ~2% peptide density in both disease models. Taken together, these results demonstrate the significance of using effective design elements such as the appropriate peptide EG-linker length in coordination with the appropriate liposomal PEG coating and optimal ligand density in efficient cellular uptake of liposomal nanoparticles.

Additionally, ligand-targeted nanoparticles are provided as drug delivery vehicles for cancer therapy. The cellular uptake of peptide-targeted liposomes and micelles is demonstrated herein to be significantly enhanced by increasing the hydrophilicity of the targeting peptide sequence while simultaneously optimizing the EG peptide-linker length. Two distinct disease models were analyzed as the nanoparticles were functionalized with either VLA-4 or HER2 antagonistic peptides to target multiple myeloma or breast cancer cells, respectively. Our results demonstrated that including a short oligolysine chain adjacent to the targeting peptide sequence effectively increased cellular uptake of targeted nanoparticles up to ~80 fold using an EG6 peptide-linker in liposomes and ~27 fold using an EG18 peptide-linker in micelles for the VLA-4/multiple myeloma system. Similar trends were also observed in the HER2/breast cancer system with the EG18 peptide-linker resulting in optimal uptake for both types of nanoparticles. These results further demonstrate the significance of using appropriately effective design elements, as described herein, to improve the cellular uptake of nanoparticles.

Accordingly, the invention provides liposomal and micellar drug delivery systems that display enhanced cellular uptake compared to commonly used nanoparticles having longer PEG chains in their nanoparticle halos. The nanoparticles of the invention can be used to deliver a variety of therapeutic agents including encapsulated anticancer drugs and conjugated pro-drugs, such as proteasome inhibitors.

Proteasomes are proteins responsible for the degradation of misfolded proteins. They also play a role in some cell signaling pathways. Proteasome inhibitors are therefore an important target in oncology. Bortezomib and carfilzomib are FDA approved first and second generation proteasome inhibitors for the treatment of multiple myeloma. Despite being effective treatments, they still remain dose limited by their non-specific toxicities. In various embodiments, the invention provides for the incorporation of bortezomib and carfilzomib, as well as other therapeutics, into long circulating liposomes for improved drug delivery and enhanced tumor accumulation. The drug-loaded nanoparticles are internalized by and cytotoxic to cancer cells such as multiple myeloma cell lines. Xenograph models show that the nanoparticles show reduced systemic toxicity with improved tumor growth inhibition compared to the corresponding free drug. This disclosure demonstrates the successful incorporation and administration of drugs such as bortezomib- and carfilzomib-loaded nanoparticles. These methods can be extended to other therapeutic agents such as anticancer therapeutics.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to one embodiment", an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and the include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase one or more is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", more than", or "more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

A "targeting molecule" or "targeting agent" is a peptide, cyclic peptide, peptidomimetic, or other molecule that binds to a targeted moiety (e.g., a cell surface molecule of a cell targeted for treatment, and/or an extracellular matrix component). Optionally, the binding affinity of the targeting molecule may be in the range of 1 nM to 1 µM. In some embodiments, the targeting molecule may be an antagonist of a receptor on the surface of a targeted cell.

A "therapeutic agent", "active agent", or "drug" refers to any molecule used in the treatment, cure, prevention, or diagnosis of a disease or other medical condition. Examples of therapeutic agents include, but are not limited to, FDA-approved drugs, experimental anti-cancer drugs, antibiotics, and nucleic acids (e.g., siRNA, DNA). Specific examples of therapeutic agents include, but are not limited to, bortezomib, carfilzomib, and platinum-containing drugs (e.g., cisplatin, carboplatin, derivatives thereof), as well as other therapeutic agents described herein.

As used herein, a "nanoparticle" refers to a micelle or liposome.

The term "HSPC" refers to the lipid Hydro Soy PC, or hydrogenated soy L-α-phosphatidylcholine, CAS Number 97281-48-6, a versatile phospholipid useful for preparing micelles or liposomes.

The term "DSPE" refers to "1,2-distearoyl-sn-glycero-3-phosphoethanolamine. DSPE can be readily conjugated to poly(ethylene glycol) to provide a pegylated phospholipid (PEG-DSPE) for the preparation of micelles or liposomes. DSPE and PEG-DSPE are commercially available from suppliers such as Avanti Polar Lipids, Inc.

The ($C_{14}$-$C_{24}$)acyl moieties of the compounds described herein can be derived from fatty acids or fatty acid esters. A "fatty acid" refers to an alkanoic acid or an alkanoic acid moiety (i.e., the residue left after formal removal of the acid hydrogen), where the fatty acid includes at least about nine or ten carbon atoms. Non-limiting examples of fatty acids include decanoic acid (10:0), undecanoic acid (11:0), 10-undecanoic acid (11:1), lauric acid (12:0), cis-5-dodecanoic acid (12:1), tridecanoic acid (13:0), myristic acid (14:0), myristoleic acid (cis-9-tetradecenoic acid, 14:1), pentadecanoic acid (15:0), palmitic acid (16:0), palmitoleic acid (cis-9-hexadecenoic acid, 16:1), heptadecanoic acid (17:1), stearic acid (18:0), elaidic acid (trans-9-octadecenoic acid, 18:1), oleic acid (cis-9-octadecanoic acid, 18:1), nonadecanoic acid (19:0), eicosanoic acid (20:0), cis-11-eicosenoic acid (20:1), 11,14-eicosadienoic acid (20:2), heneicosanoic acid (21:0), docosanoic acid (22:0), erucic acid (cis-13-docosenoic acid, 22:1), tricosanoic acid (23:0), tetracosanoic acid (24:0), nervonic acid (24:1), pentacosanoic acid (25:0), hexacosanoic acid (26:0), heptacosanoic acid (27:0), octacosanoic acid (28:0), nonacosanoic acid (29:0), triacosanoic acid (30:0), trans vaccenic acid (trans-11-octadecenoic acid, 18:1), tariric acid (octadec-6-ynoic acid, 18:1), and ricinoleic acid (12-hydroxyoctadec-cis-9-enoic acid, 18:1) and ω3, ω6, and ω9 fatty acyl residues such as 9,12,15-octadecatrienoic acid (α-linolenic acid) [18:3, ω3]; 6,9,12,15-octadecatetraenoic acid (stearidonic acid) [18:4, ω3]; 11,14,17-eicosatrienoic acid (dihomo-.alpha.-linolenic acid) [20:3, ω3]; 8,11,14,17-eicosatetraenoic acid [20:4, ω3]; 5,8,11,14,17-eicosapentaenoic acid [20:5, ω3]; 7,10,13,16,19-docosapentaenoic acid [22:5, ω3]; 4,7,10,13,16,19-docosahexaenoic acid [22:6, ω3]; 9,12-octadecadienoic acid (linoleic acid) [18:2, ω6]; 6,9,12-octadecatrienoic acid (γ-linolenic acid) [18:3, ω6]; 8,11,14-eicosatrienoic acid (dihomo-γ-linolenic acid) [20:3, ω6]; 5,8,11,14-eicosatetraenoic acid (arachidonic acid) [20:4, ω6]; 7,10,13,16-docosatetraenoic acid [22:4, ω6]; 4,7,10,13,16-docosapentaenoic acid [22:5, ω6]; 6,9-octadecadienoic acid [18:2, ω9]; 8,11-eicosadienoic acid [20:2, ω9]; 5,8,11-eicosatrienoic acid (Mead acid) [20:3, ω9]; trans-10,cis-12 octadecadienoic acid; cis-10,trans-12 octadecadienoic acid; cis-9, trans-11 octadecadienoic acid; and trans-9,cis-11 octadecadienoic acid. The acyl residues of a fatty acid moiety can also be conjugated, hydroxylated, epoxidized, and/or hydroxyepoxidized acyl residues. Thus, the ($C_{13}$-$C_{23}$)acyl moieties can be derived from any one or more of these fatty acids.

The term lipid includes mono-, di- and triacylglycerols, phospholipids, free fatty acids, fatty alcohols, cholesterol, cholesterol esters, and the like.

The term "phospholipid" as used herein refers to a glycerol phosphate with an organic headgroup such as choline, serine, ethanolamine or inositol and zero, one or two (typically one or two) fatty acids esterified to the glycerol backbone. Phospholipids include, but are not limited to, phosphatidylcholine, phosphatidylethanolamine, phosphatidylserine and phosphatidylinositol as well as corresponding lysophospholipids.

The terms "active agent", "therapeutic agent", "anticancer agent", "drug", and the like, are readily recognized by those of kill in the art. The micelles and liposomes described herein can encapsulate various drugs, such as those drugs exemplified in the description herein, including anticancer agents such as for example, etoposide, bortezomib, staurosporine, doxorubicin, tamoxifen, cisplatin, carboplatin, paclitaxel, or another chemotherapeutic or otherwise active agent known in the art.

Nanoparticle Components

In addition to the nanoparticle components described in the Examples below, the nanoparticles can include additional components including hydrophobic or hydrophilic drugs, encapsulated in the micelle or liposome interior, or in the liposome bilayer. Various drugs conjugated to PEG or a lipid, such as a phospholipid, can also be incorporated into the nanoparticles. One specific example of an additional component is doxorubicin, either as a cargo molecule or conjugated to a lipid (see Kiziltepe et al., *Blood Cancer J.* 2012, 2, e64).

In certain embodiments, nanoparticle components can include Pt(IV)-azide prodrug conjugates such as those described by Xiao and coworkers (*J. Cont. Release* 173 (2014), 11-17). In various embodiments, nanoparticle components can include multinuclear Pt(II) drug moieties such as those described by Xiao and coworkers (*Chem. Commun.* 2013; DOI: 10.1039/c3cc39119a). In further embodiments, the nanoparticles can include diagnostic agents or therapeutic agents such as those described by Noble and coworkers (*Trends Biochem.* 2014, 32(1), 32-45. Examples of such diagnostic agents and therapeutic agents, and the types of cancer they can treat are illustrated in FIG. 36.

In some embodiments, the nanoparticles can include targeting molecules on their surfaces. Targeting molecules can be an antagonists of a target cell surface receptor. In some embodiments, a targeting molecule can be a VLA-4 antagonist. In the certain specific embodiments, the targeting molecule can be is a VLA-4 antagonist peptide ("VLA-4-pep") that is configured to bind to fibronectin and/or to VLA-4. Other examples of VLA-4 antagonists that can be used as targeting molecules include, but are not limited to, peptide sequences with a consensus LDV sequence, cyclic peptides with an RCD motif, peptides derived from fibronectin CS-1, peptides derived from fibronectin RGD tripeptide, peptides derived from fibronectin RGD and vascular cell adhesion molecule-1, peptides derived from anti-α4 monoclonal antibody, and other VLA-4 antagonists known in the art. Additional examples of VLA-4 antagonists are described in Jackson et al., *J. Med. Chem*, 40, 3359-3368, 1997; Lin et al., *Curr. Opin. Chem. Biol.*, 2, 453-457, 1998; and Tilley, *Expert Opin. Ther. Pat.*, 18, 8, 841-859, 2008. Alternatively, a targeting molecules may be antagonists and/or ligands of other receptors. Examples of other targeting molecules include, but are not limited to, folate (binds folate receptor), RGD peptide sequences against the αvβ3 integrin, and peptide antagonists of the Human Epidermal Growth Factor Receptor 2 (HER2).

Nanoparticle Methods

In various embodiments, the invention provides pharmaceutical compositions comprising a plurality of nanoparticle and a pharmacologically acceptable excipient. The nanoparticle may have a therapeutic agent coupled to the outer portion of the particle, as well as a targeting agent coupled to the surface and exposed outside a PEG corona of the nanoparticle. Administration of drug loaded or drug conjugated nanoparticles can treat cancerous tissue or cells by contacting the tissue or cells and being taken up by the cells, and degrading to release the therapeutic agent(s).

Pharmaceutical Formulations

The nanoparticles described herein can be used to prepare therapeutic pharmaceutical compositions, for example, by combining the nanoparticles with a pharmaceutically acceptable diluent, excipient, or carrier. The nanoparticles described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The nanoparticles described herein may be systemically administered in combination with a pharmaceutically acceptable vehicle, such as an inert diluent or an assimilable edible carrier. For oral administration, nanoparticles can be enclosed in hard or soft shell gelatin capsules, compressed into tablets, or incorporated directly into the food of a patient's diet. Nanoparticles may also be combined with one or more excipients and used in the form of ingestible tablets, buccal tablets, troches, capsules, elixirs, suspensions, syrups, wafers, and the like. Such compositions and preparations typically contain at least 0.1% of the nanoparticles. The weight percentage of the nanoparticles in the preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the nanoparticles may be incorporated into sustained-release preparations and devices.

The nanoparticles may be administered intravenously or intraperitoneally by infusion or injection. Solutions of the nanoparticles can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the nanoparticles for the extemporaneous preparation of sterile injectable or infusible solutions or dispersions. The ultimate dosage form for injection or infusion should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the nanoparticles in the required amount in the appropriate solvent or carrier with various other ingredients enumerated above, as required, optionally followed by filter sterilization. In the case of sterile powders for the preparation of sterile injectable solutions, methods of preparation can include vacuum drying and freeze drying techniques, which yield a powder of the nanoparticles plus any additional desired ingredient present in the composition.

For topical administration, nanoparticles may be applied in pure form or as a solution. However, it will generally be desirable to administer the nanoparticles to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which nanoparticles can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the nanoparticles described herein where an ingredient of such compositions can optionally be replaced by a compound or composition described herein, or a compound or composition described herein can be added to the composition.

Useful dosages of the nanoparticles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of nanoparticles required for use in treatment will vary not only with the particular active compound of the nanoparticles but also with the route of administration, the nature of the condition being treated, and the age and condition of the patient, and will be ultimately at the discretion of an attendant physician or clinician.

The active compound of the nanoparticles can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The nanoparticles described herein can be effective anti-tumor compositions and have higher potency and/or reduced toxicity as compared to the corresponding free active drug in the nanoparticles. The invention provides therapeutic methods of treating cancer in a mammal, which involve administering to a mammal having cancer an effective amount of a nanoparticles composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the methods described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Systematic Analysis of Peptide Linker Length and Liposomal PEG Coating on Cellular Uptake of Peptide-Targeted Liposomes There is currently an extensive debate on the relative contributions of active versus passive targeting in nanoparticle-based drug delivery systems. The apparent discrepancy observed in the field of targeted liposomal nanoparticles has in part been attributed to differences in type of tumor models. However, the discrepancy most likely originates from the PEG coatings of the particles, linkers used to conjugate the targeting ligands, as well as the different types of targeting ligands. Solutions to the challenges of effective targeting are provided in this Example.

On liposomal nanoparticles, PEG serves two functions: i) to provide stealth to the particles for increased circulation time and ii) to act as a linker to connect the targeting ligand to the particle. The current clinical and research standard for establishing optimal in vivo circulation enhancement is the incorporation of a 5 mole percent methoxy-PEG2000-DSPE (PEG2000; a mean of ~45 repeating units of ethylene glycol: EG45) in the liposome formulation (Allen et al., *Anti-cancer Agents in Med. Chem.* 2006, 6, 513-523; Allen et al., *Biochim. Biophys. Acta* 1991, 1066). This polymer length and percentage provides complete PEG coating of the liposome surface while maintaining particle stability. PEG2000 has also been used as a linker to conjugate targeting ligands. In certain particle designs, use of a longer linker such as PEG3350 or PEG5000 has been preferred presumably because longer linkers may present the targeting ligand above the PEG coating more effectively (Sapra et al., *Curr. Drug Deliv.* 2005, 2, 369-381; Sapra et al., *Prog. Lipid Res.* 2003, 42, 439-462; Gabizon et al., *Clin. Cancer Res.* 2003, 9; Yamada et al., *Clin. Cancer Res.* 2008, 14).

Figure 3A:
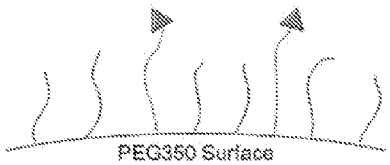
FIG. 3. A schematic representation of targeting peptides (triangles) tethered to a liposome surface in the presence of (A) a liposome having a surface coated with PEG350, wherein the peptide tether is an EG6-EG18 tether, and (B) a liposome having a surface coated with PEG2000 wherein the peptide tether longer than EG18.
Figure 3B:
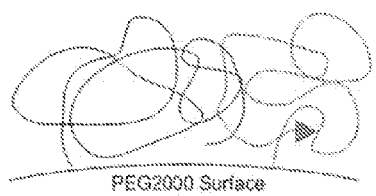

However, it is well established that long PEG polymers including PEG2000, PEG3350, and PEG5000 do not have a linear conformation in water. Rather, they fold into a mushroom like globular structure, burying a large fraction of the conjugated ligand into the PEG coating and sterically hindering the association of the ligand-targeted liposome with its target receptor (see FIG. 3B). Although PEG itself has been determined to be an ideal molecule to enhance bioavailability of liposomal nanoparticles, the use of PEG2000 specifically as a liposomal coating and linker has been, in part, due to traditional reasons rather than scientific reasoning. Several reports in literature demonstrate that similar bioavailability profiles and in vivo circulation half-life can be achieved with liposomal PEG molecules such as PEG350, PEG550, and PEG750, despite the estimated PEG coverage of <100%. Furthermore, a shorter peptide linker may provide a more favorable thermodynamic receptor-ligand interaction. Although enthalpic parameters would remain the same regardless of linker length, a short linker would restrict the translational and conformational freedom of the peptide, reducing the overall entropic loss when the liposome binds to the cell. These provide a strong scientific rationale to evaluate the effect of shorter peptide linker lengths, in coordination with various liposomal PEG coatings, on tumor cell targeting and uptake.

In studies to date, the most common method of generating ligand-targeted nanoparticles involves coupling targeting elements directly to pre-formed nanoparticles as a second step following the preparation of the nanoparticles. However, this approach results in significant variations in coupling yields and decreases binding activity due to side reactions that can yield chemical and conformational changes to the ligand. This process causes batch-to-batch variations in ligand-targeted nanoparticle preparation and results in highly heterogeneous nanoparticle populations with inconsistent outcomes in cellular uptake and tumor targeting.

In this Example, a multifaceted synthetic strategy was employed where the targeting ligand is synthesized as a lipid conjugate and subsequently purified prior to nanoparticle preparation. The liposomal components are then mixed at various molar ratios during nanoparticle preparation (see, for example, Table 1.2), a procedure that yields highly reproducible results with high purity and precisely controlled stoichiometric loading of targeting ligands. The precision and purity of nanoparticles prepared with this method enables effective selection of liposomal PEG coating, peptide linker length, and peptide density on cellular uptake in a systematic manner, without other compounding factors.

In particular, by using well-characterized liposomes, the effect of these parameters on cellular uptake by Human Epidermal Growth Factor Receptor 2 (HER2) overexpressing breast cancer cells were evaluated in detail. HER2 is overexpressed in 25% of breast cancer cases and is associated with poor prognosis, making it an ideal receptor to target this disease. In our approach, we used a short cyclic-peptide antagonist of HER2 as the targeting ligand and identified the optimal design elements for maximum cellular uptake. We then validated our findings by applying and evaluating the optimized design elements in a Very Late Antigen-4 (VLA-4) overexpressing multiple myeloma model. In both disease models, we consistently demonstrated that cellular uptake is significantly enhanced when a shorter peptide linker such as EG12 was used in combination with PEG350 liposomal coating instead of the industry standard PEG2000. These results established the significance of using the right design elements, such as the appropriate peptide EG-linker length in coordination with the appropriate liposomal PEG coating and optimal ligand density in efficient targeting of tumors.

Results and Discussion.

Figure 4:
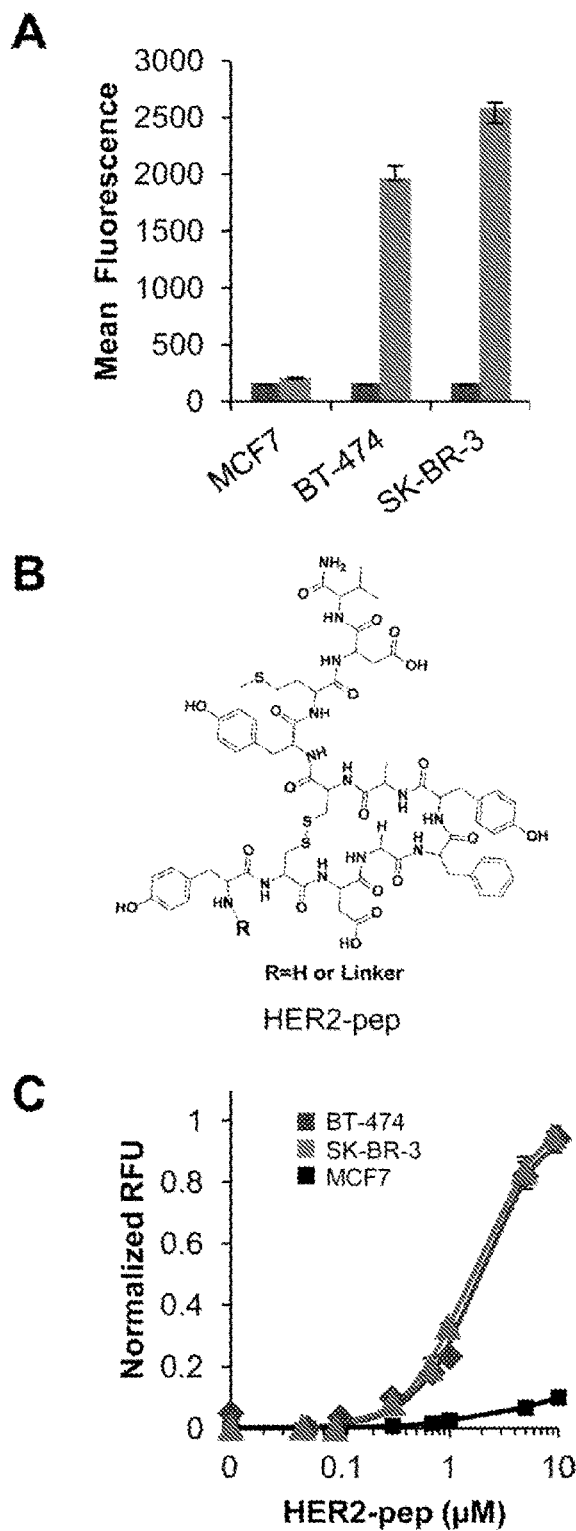
FIG. 4. HER2 expression in breast cancer cells and identification of a HER2-antagonist peptide. (A) HER2 expression levels in MCF7, BT-474, and SK-BR-3 were determined in a flow cytometry assay using a primary anti-HER2 antibody followed by a fluorescein labeled secondary antibody (right-side columns). Isotype controls are shown in the left-side columns. (B) Structure of HER2-antagonist peptide (HER2-pep) is shown, which may be conjugated to other moieties (R), such as a PEG linker or other compounds described herein. C) Cellular binding assays were performed using fluorescein labeled HER2-pep and binding to BT-474 (diamond), SK-BR-3 (triangle), and MCF-7 (square) was detected by flow cytometry. Control experiments were performed with fluorescein labeled non-specific peptide and the background binding was subtracted for each data point. Fluorescence signal was normalized based on the highest and lowest observed values for the BT-474 and SK-BR-3 cell lines. All experiments were done in triplicates and data represents means (±s.d.).

Validation of the Selective Binding of a HER2-Antagonist Peptide to HER2-Overexpressing Breast Cancer Cells. HER2 is overexpressed in 25% of breast cancer cases and there are several HER2-overexpressing breast cancer cell lines, including BT-474 and SK-BR-3, that provide useful tools to evaluate and optimize HER2-targeted liposomal nanoparticles. We validated HER2 expression in these cell lines in a flow cytometry assay by using an anti-HER2 primary antibody followed by a fluorescein labeled secondary antibody. HER2 expression levels were consistent with values previously reported in literature, with both the BT-474 and SK-BR-3 cell lines overexpressing HER2 in significant quantities (FIG. 4A). The MCF7 breast cancer cell line was used as a negative control with very low levels of HER2 expression.

In our approach, to target HER2-overexpressing cells, we used a short cyclic-peptide sequence as the targeting ligand for the various advantages provided over the use of conventional antibody macromolecules (or their fragments) including ease of preparation, lower cost, lower antigenicity, decreased opsonization, and increased stability to degradation. With a broad range of affinities, peptide targeted therapies can provide selectivity through multiple low to moderate affinity interactions (Owen et al., *ChemBioChem* 2007, 8, 68-82; Mammen et al., *Angew. Chem.-Int. Edit.* 1998, 37, 2755-2794). Liposomes also provide excellent scaffolds for multivalent presentation of the peptide ligands, enhancing the binding avidity and selectivity for overexpressed receptors. The cyclic peptide sequence, YCDGFYA-CYMDV (SEQ ID NO: 1) (HER2-pep; FIG. 4B), was previously identified as a HER2-antagonist by Berezov et al. and has been reported to bind to an extracellular HER2 domain with submicromolar affinity ($K_d$=150 nM) (*J. Med. Chem.* 2001, 44, 2565-2574).

We demonstrated selective binding of this peptide to SK-BR-3 and BT-474 cells in a cellular binding assay, where we incubated the cells on ice with a fluorescein labeled version of this peptide and detected peptide binding using flow cytometry (FIG. 4C). Control experiments performed with labeled non-specific peptide showed only minimal background binding and was subtracted from each data point. HER2-pep demonstrated efficient and selective binding to both SK-BR-3 ($K_d$=1.75 µM) and BT-474 ($K_d$=1.97 µM) cell lines. Only minimal binding was observed to the MCF7 cells, consistent with the negligible levels of HER2 expression. It is noteworthy that we observed ~10 fold weaker binding affinity in cellular binding assays compared to the binding reported for the recombinant HER2 protein. This apparent difference most likely emerges from the steric and structural differences between the HER2 receptor that is overexpressed on the surface of cancer cells and the recombinantly expressed soluble HER2 protein that was used in the previous studies.

Development of a Multifaceted Synthetic Strategy for Preparation of Ligand-Targeted Liposomal Nanoparticles with Precisely Controlled Stoichiometry of Functionalities. In the most commonly employed methods to date, targeting ligands are coupled directly to preformed nanoparticles resulting in significant fluctuations in coupling yields, decreased ligand activity, surface heterogeneity, and substantial batch-to-batch variation. To overcome these problems, we employed a multifaceted synthetic strategy in our approach, where we synthesized and purified the peptide-EG-lipid conjugates to >98% purity prior to nanoparticle preparation. This method of peptide incorporation has several advantages when compared to the post-insertion methods commonly used including: precise control over the number of targeting ligands, elimination of variability in coupling yield, and elimination of decreased binding activity due to chemical side reactions. In addition, this strategy eliminates the need to purify the liposomes that are formed, ensuring maximal particle recovery. This approach results in highly homogeneous particle populations with high purity while minimizing batch-to-batch variability.

Figure 5:
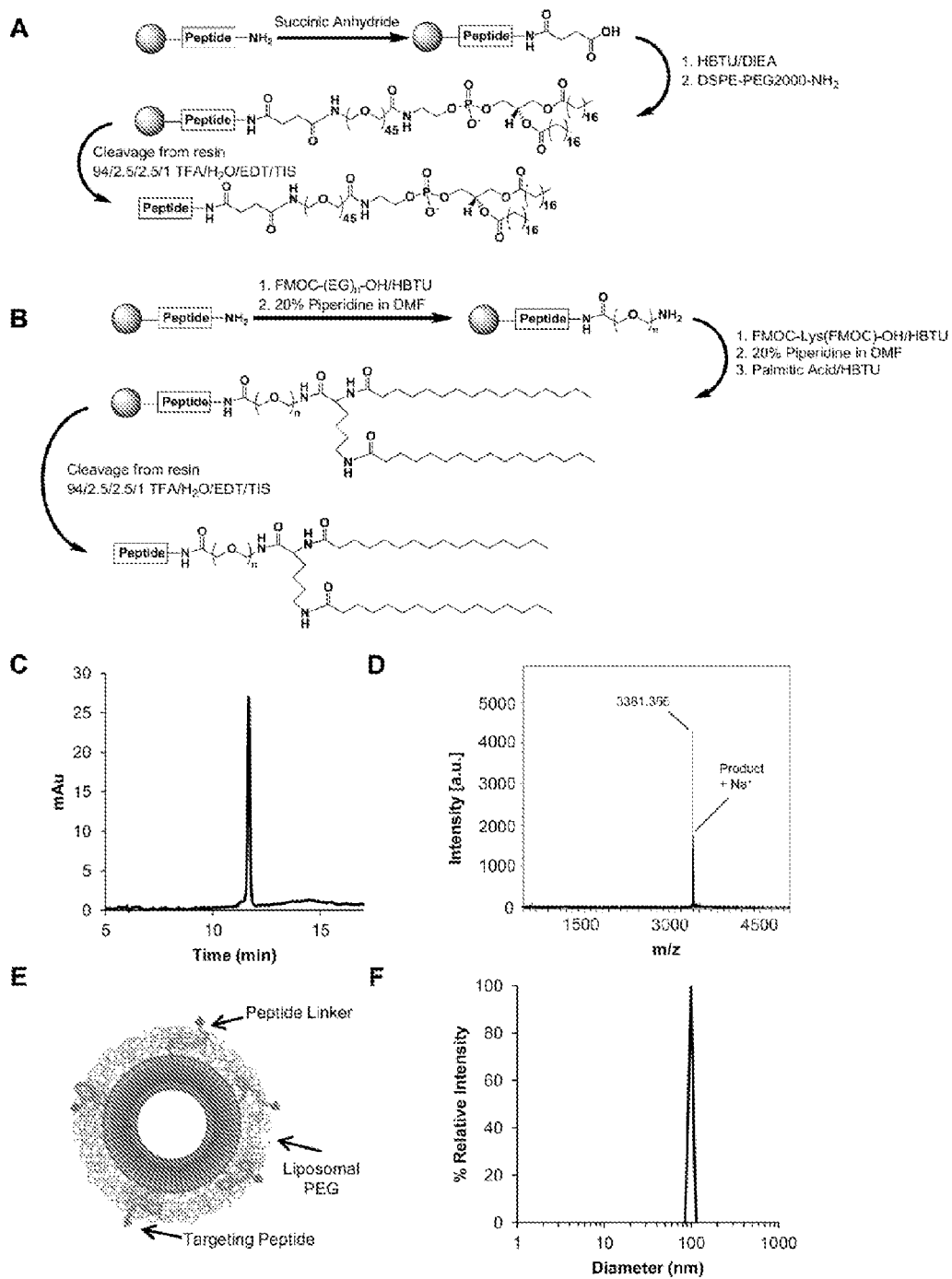
FIG. 5. Synthesis and characterization of targeting peptide conjugated liposomes. (A) Schematic of the synthetic steps for peptide conjugation to DSPE-PEG2000-NH$_2$ (~45 EG units) using solid support. (B) Schematic of the synthesis of amphiphilic molecules with various peptide EG-linker lengths, including EG6, EG12, EG18, EG24, EG30, EG36, and EG72. C) Representative RP-HPLC chromatograph of HER2-pep with EG12 peptide linker showing high purity of synthesized molecules. D) Representative MALDI-MS spectrum of HER2-pep with EG12 linker. Expected mass 3380.85. Found mass 3381.356. (E) Schematic of the synthesized ligand-targeted liposomes. (F) Dynamic light scattering analysis of nanoparticles.

We performed the synthesis of the peptide-EG-lipid conjugates on a solid support, using standard Fmoc chemistry protocols (FIG. 5). Because the various peptide EG-linker lengths that were employed in this study had different chemical functionalities, two different synthetic strategies on the solid support were employed to create the desired products. The first synthetic strategy, schematically illustrated in FIG. 5A, was used to conjugate DSPE-PEG2000-NH₂ to the targeting peptide, which was synthesized on either the Rink amide or Wang resin. Following the last Fmoc protecting group removal, succinic anhydride was introduced to react with the free N-terminus to generate a carboxylic acid moiety at the distal end of the peptide. This carboxylic acid was activated with HBTU, which was followed by introduction of DSPE-PEG2000-NH$_2$ in DMF, and the reaction was run overnight. The resulting product was cleaved from the resin and purified via RP-HPLC. Peptide cyclization through disulfide bond formation was performed in DMF with DIEA at room temperature overnight and re-purified.

This approach dramatically increased the product yield (~20%) compared to a conjugation strategy where the carboxylic acid is positioned on the PEG2000 linker and is coupled to the amine terminus of the peptide, which yielded practically no product. Nevertheless, with the shorter EG linkers, the coupling yields for the reactions where the carboxylic acid terminus was on the EG was merely satisfactory (10-65% product yield), hence we followed a different synthetic approach (FIG. 5B). As in the first strategy, the peptide was synthesized on a resin, followed by the coupling of an EG linker of a desired length. The EG linker contains a carboxylic acid moiety to couple to the amine containing peptide and an Fmoc protected amine functionality for continued synthesis. After removal of the Fmoc from the peptide coupled EG, an L-lysine residue is coupled to provide branching. Two fatty acyl chains are then coupled to both the α- and ε-amines to generate the hydrophobic tail of the molecule that will embed into the lipid bilayer of the liposomes. Palmitic acid was chosen in lieu of a conventional carboxylic acid terminated phospholipid, such as DPPE-GA, because of its greater chemical stability due to the lack of the phosphoester bond and increased solubility in typical solid phase reaction solvents such as DMF and DCM. The products were then cleaved from the resin and purified via RP-HPLC. Purity of the synthesized conjugates were characterized by analytical HPLC and mass spectrometry analysis, where we routinely achieved greater than 98% purity as demonstrated by the representative HPLC (FIG. 5C) and MS peaks (FIG. 5D) of EG12 conjugated HER2-pep. Mass spectrometry data and product yields of the synthesized peptide-EG-lipid conjugates were recorded (see Stefanick et al., ACS NANO 2013, 7(4), 2935-2947 and its Supporting Information, and Table 1.1).

TABLE 1.1

Mass spectrometry data and yields for peptide(K$_N$)-EG$_{linker}$-lipid conjugates.

Peptide(K$_N$)-EG$_{linker}$-Lipid Characterization

| | | VLA4pep(K$_N$) | | | HER2pep(K$_N$) | | |
|---|---|---|---|---|---|---|---|
| Linker (EG units) | # Lysine Residues[a] | Expected Mass (Da) | Found Mass (Da)[b] | Product Yield (%) | Expected Mass (Da) | Found Mass (Da)[b] | Product Yield (%) |
| 6 | 0 | 1722.98 | 1723.543 | 73.2 | 2573.33 | 2574.344 | 62.9 |
| 6 | 1 | 2152.715 | 2153.24 | 71.5 | — | — | — |
| 6 | 2 | 2208.3 | 2208.872 | 70.6 | — | — | — |
| 6 | 3 | 2266.36 | 2289.414[c] | 75.6 | 3116.71 | 3117.724 | 57.2 |
| 6 | 4 | 2394.29 | 2395.33 | 70.2 | — | — | — |
| 12 | 0 | 2059.17 | 2059.963 | 66.7 | 2837.48 | 2838.038 | 56.5 |
| 12 | 3 | 2602.55 | 2603.343 | 64.4 | 3380.86 | 3381.418 | 51.4 |
| 18 | 0 | 2393.37 | 2394.033 | 49.7 | 3171.67 | 3172.857 | 52.1 |
| 18 | 1 | 2823.095 | 2824.13 | 48.6 | 3601.41 | 3602.440 | 41.3 |
| 18 | 2 | 2878.68 | 2879.12 | 42.1 | 3656.99 | 3657.430 | 45.6 |
| 18 | 3 | 2936.74 | 2937.413 | 49.5 | 3715.05 | 3716.237 | 47.4 |
| 18 | 4 | 3064.67 | 3065.71 | 40.5 | 3842.98 | 3844.020 | 47.2 |
| 24 | 0 | 2515.45 | 2516.736 | 39.4 | 3364.79 | 3366.121 | 45.8 |
| 24 | 3 | 3058.83 | 3060.116 | 40.2 | 3908.17 | 3909.501 | 41.6 |
| 30 | 0 | 2850.65 | 2851.249 | 33.6 | 3699.98 | 3700.256 | 34.8 |
| 30 | 3 | 3394.03 | 3394.629 | 35.6 | 4243.36 | 4243.636 | 31.6 |
| 36 | 0 | 3191.9 | 3192.836 | 31.5 | 4035.18 | 4036.335 | 33.7 |
| 36 | 3 | 3735.28 | 3736.216 | 30.5 | 4578.56 | 4579.715 | 30.6 |
| 45 | 0 | 3485.9 | 3486.731 | 22.1 | 4381.86 | 4382.964 | 19.4 |
| 45 | 3 | 4029.28 | 4030.111 | 25.1 | 4925.24 | 4926.344 | 17.6 |
| 72 | 0 | 4826.86 | 4827.723 | 11.2 | 5676.18 | 5677.062 | 10.6 |
| 72 | 3 | 5370.24 | 5371.581 | 10.2 | 6219.56 | 6220.442 | 9.6 |

[a]Ala used in place of Lys in molecules with 1, 2, or 3 Lys residues to preserve peptide linker length.
[b]Mass determined by MALDI-TOF MS.
[c]Represents mass + Na$^+$ adduct.

Liposomes were prepared using purified peptide-EG-lipid conjugates, PEG-DSPE, HSPC, and cholesterol, which were mixed to produce nanoparticles with the desired peptide linker length and liposomal PEG coating (FIG. 5E). The components were mixed at specific stoichiometries to achieve precise control over the number of functional ligands on each particle, while maintaining reproducibility in nanoparticle production. Nanoparticles with varying liposomal PEG coating, varying peptide EG-linker length, and varying peptide densities were prepared to evaluate the effect of these parameters on cellular uptake and tumor targeting. The liposomes were sized via extrusion through a polycarbonate membrane to yield an average diameter of 100 nm as detected by DLS analysis (FIG. 5F). Lissamine rhodamine B PE or fluorescein PE was incorporated into the liposomes for cellular uptake and imaging experiments. Regardless of liposomal formulation, including the addition of fluorescent imaging agents or targeting agents, the mean diameter of the particles remained constant (Table 1.2 for particle sizing and zeta potential measurements).

TABLE 1.2

Particle size and zeta potential for select liposome and micelle formulations.
The particle size and zeta potential of non-targeted nanoparticles and targeted optimal liposome and micelle formulations

| Nanoparticle | Formulation | Particle Size (nm) | Zeta-potential (mV) |
|---|---|---|---|
| Liposome | | | |
| Control | 95:10:5 HSPC:CHOL:PEG2000 | 101.5 ± 3.5 | −23.9 ± 2.5 |
| VLA4pep($K_3$)[1] | 93:10:5:2 HSPC:CHOL:PEG2000:VLA4($K_3$)-pep | 103.4 ± 2.1 | −22.4 ± 3.7 |
| HER2pep($K_3$)[2] | 93:10:5:2 HSPC:CHOL:PEG2000:HER2($K_3$)-pep | 99.9 ± 4.5 | −22.2 ± 2.1 |
| Micelle | | | |
| Control | 90 PEG2000 | 17.7 ± 2.8 | −13.1 ± 5.1 |
| VLA4pep($K_3$)[2] | 80:10 PEG2000:VLA4($K_3$)-pep | 18.8 ± 4.1 | −12.3 ± 3.1 |
| HER2pep($K_3$)[2] | 75:15 PEG2000:HER2($K_3$)-pep | 16.7 ± 3.2 | −11.1 ± 2.9 |

Figure 6:
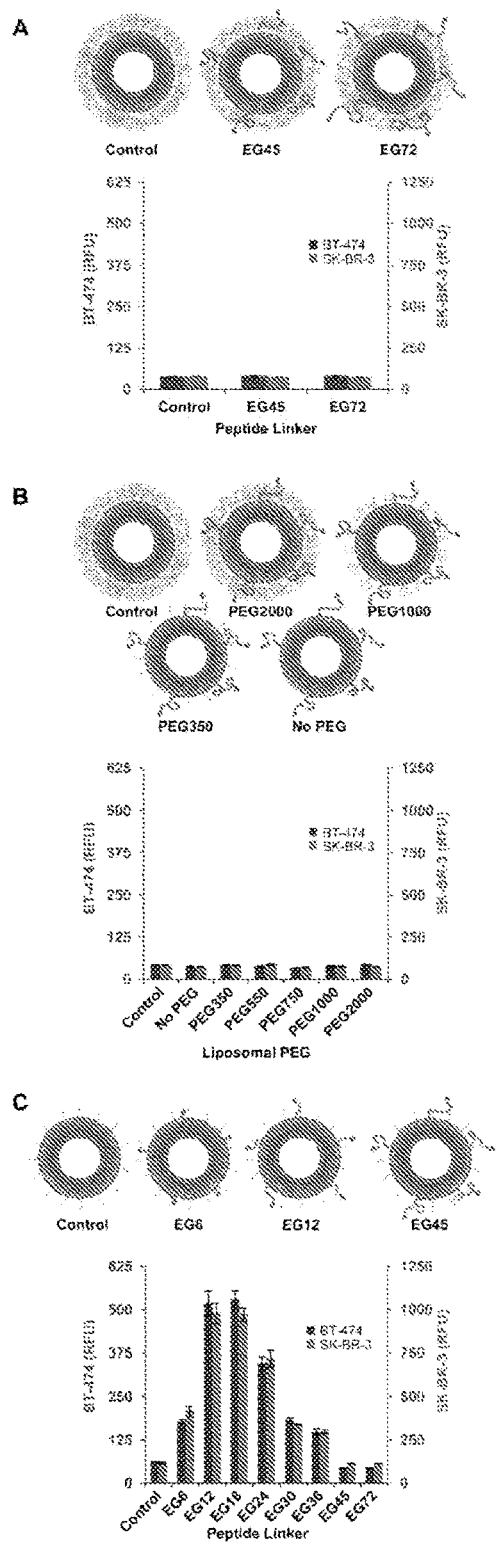
FIG. 6. Effect of liposomal PEG coating and peptide EG-linker length on the cellular uptake of HER2-targeted liposomes. A) Liposomes composed of PEG2000 liposomal coating with and without the EG45 or EG72 peptide linker were assayed for cellular uptake. B) The effect of liposomal PEG length on the uptake of HER2 targeted liposomes with EG45 linker. The liposomal PEG lengths investigated include: PEG350, PEG550, PEG750, PEG1000, and PEG2000. C) The effect of peptide-EG-linker length on the uptake of liposomes with PEG350 liposomal coating. The peptide linker lengths investigated include: EG6, EG12, EG18, EG24, EG30, EG36, EG45, and EG72. Non-targeted controls were also included. Cellular uptake by BT-474 cells (left y-axis; left-side columns) and SK-BR-3 cells (right y-axis; right-side columns) were determined by flow cytometry. All experiments were done in triplicates and data represents means (±s.d.).

[1]Targeting peptides contain EG6 peptide-linker
[2]Targeting peptides contain EG18 peptide-linker Effect of Liposomal PEG Coating on Cellular Uptake. The standard method for generating stealth nanoparticles for an increased in vivo circulation half-life is the incorporation of 5% PEG2000. Literature reports suggest that for efficient active targeting, length of the linker molecule has to be at least as long as the PEG coating (Sapra et al., *Curr. Drug Deliv.* 2005, 2, 369-381; Sapra et al., *Prog. Lipid Res.* 2003, 42, 439-462). Therefore, in targeted liposome preparations, attaching the targeting ligand onto the distal end of functionalized PEG molecules—that are of at least ~45 ethylene glycol units (EG45 ≈PEG2000)—has become the standard for both academic and industrial research. However, it is well established that long PEG molecules do not have a linear conformation in water, but rather fold into a globular mushroom like structures, possibly hindering the accessibility of the targeting ligand on the liposome surface. Furthermore, in our experiments performed with HER2-pep targeted liposomes, we observed no difference in the uptake of targeted (95:10:3:2 HSPC:CHOL:PEG2000:HER2-pep) or non-targeted (95:10:5 HSPC:CHOL:PEG2000) nanoparticles prepared by a PEG2000 liposomal coating and an EG45 or EG72 peptide linker, further supporting this hypothesis (FIG. 6A). This prompted the question of whether the standard way of preparing targeted liposomes is optimal for maximal cellular targeting. Importantly, it has been demonstrated that 5% PEG350, PEG550, and PEG750 coatings, despite providing less than 100% surface coverage, can achieve similar circulation half-lives to 5% PEG2000 coating. This provides a strong rationale to elucidate the effects of shorter liposomal PEG coating in coordination with shorter peptide linker lengths in tumor targeting.

In our approach, we first examined the effect of liposomal PEG coating while keeping the peptide linker length of EG45 constant (FIG. 6B). Liposomal nanoparticles (100 nm) with varying PEG coatings were prepared. The liposomal PEG lengths chosen for the study include PEG350, PEG550, PEG750, PEG1000, and PEG2000, which correspond to mean EG repeat units of approximately 8, 12, 17, 22, and 45, respectively. Targeting liposomes were formulated with 95:10:3:2 HSPC:CHOL:PEGX-DSPE:HER2-pep-EG45-DSPE where X corresponds to the PEG molecular weights listed above. A non-targeted, non-PEGylated control liposome (100:10 HSPC:CHOL) was included in addition to non-targeted liposomes with variable liposomal PEG lengths (95:10:5 HSPC:CHOL:PEGX-DSPE).

For cellular uptake studies, 0.2% fluorescein PE was added as a fluorescent marker and cellular uptake was quantitatively evaluated in HER2-overexpressing breast cancer cell lines using flow cytometry. To distinguish between nanoparticle association and uptake, cells were trypsinized before flow cytometric analysis. Interestingly, our flow cytometric analysis revealed that regardless of liposomal PEG coating, there is no detectable enhancement in nanoparticle uptake with an EG45 linker, despite the addition of the HER2-pep targeting ligand (FIG. 6B). This indicates that the EG45 peptide linker itself limited the availability of the peptide to bind to its respective receptor independent of the liposomal PEG coating. Given that EG45 linker does not preserve an extended linear structure in water, but rather folds into a globular mushroom like structure, it is likely that the targeting peptides remain buried in the PEG cloud instead of being surface exposed, sterically hindering the association of the ligand with the target receptor. This led to our investigation into the effect of shorter ligand linker length to achieve enhanced cellular uptake.

Evaluation of Peptide EG-Linker Length on Uptake. Due to the success of PEG2000 in increasing liposome bioavailability in vivo, little work has been performed in evaluating shorter peptide EG-linker length in coordination with shorter liposomal PEG coatings in effective targeting. Because PEG lengths as short as PEG350 can elicit similar plasma circulation lifetimes as PEG2000, we evaluated if active targeting and cellular uptake can be enhanced by using liposomes with 5% PEG350 coating. We predicted that the use of PEG350 as the liposomal PEG will enable the use of shorter peptide EG-linker lengths to avoid the problems associated with EG45, yet still be longer than liposomal PEG350 coating to enable active targeting. Therefore, we formulated liposomes that incorporated PEG350 liposomal coating and HER2-pep conjugated lipids with varying linker lengths of EG6, EG12, EG18, EG24, EG30, EG36, EG45, and EG72 (FIG. 6C).

Targeted liposomes were formulated as 95:10:3:2 HSPC:CHOL:PEG350:HER2-pep with a non-targeted control (95:10:5 HSPC:CHOL:PEG350). Cellular uptake was evaluated with both BT-474 and SK-BR-3 cell lines. When EG6 linker was incorporated as the targeting element, there was minimal uptake presumably due to the peptide not being presented beyond the liposomal PEG coating. Alternatively, the linker may not provide enough length for the peptide to reach the binding pocket on the receptor. A remarkable enhancement in uptake was observed when using an EG12 linker (~9 fold greater than control). This trend continued for an EG18 linker, but gradually declined when EG24 linker was used and completely diminished with an EG45 and EG72 linker. Similar trends were observed at longer time points with the EG12 linker showing a ~5 fold and ~4 fold enhancement greater than control liposomes at 24 h for BT-474 and SK-BR-3, respectively.

The dramatic enhancement observed with EG12 linker is likely due to a variety of factors. Tethering the peptide to a shorter linker restricts the translational and conformational freedom of the peptide, thereby reducing the overall entropic loss when the liposome binds to the cell. Cellular binding experiments performed with targeting liposomes (95:10:3:2 HSPC:CHOL:PEG350:HER2-pep) containing either a EG12, EG24, or EG36 linker showed apparent $K_d$'s in the order of $K_d^{EG12} < K_d^{EG24} < K_d^{EG36}$ for both BT-474 and SK-BR-3 cell lines. This suggests that shortening the linkers to an optimal size does increase the avidity of the system which then facilitates binding and subsequent internalization. Furthermore, a shorter EG linker will adopt a more linear conformation, unlike a longer linker which will fold upon itself to form a globular, mushroom like structure. This decreased flexibility may also limit the nonspecific interactions of the peptide with the lipid bilayer.

It is also worthwhile to evaluate the effect of lipid tail content on uptake efficiency. To this end, we synthesized HER2-pep with an EG12 peptide linker and a variety of lipid tail designs including stearic acid, DPPE, DSPE, and DOPE to compare to the results with the palmitic acid tails. Targeted liposomes were formulated as 95:10:3:2 HSPC:CHOL:PEG350:HER2-pep with a non-targeted control consisting of 95:10:5 HSPC:CHOL:PEG350. Results show near identical results when stearic acid, DPPE, and DSPE are used a lipid tails in lieu of palmitic acid, but incorporation of DOPE decreased the uptake efficiency. These results indicate that, provided that peptides are tethered to saturated lipid tails carbons in length, the presence of the phospholipid does not adversely affect the accessibility of the peptide to bind or the net uptake of liposomes. However, the use of an unsaturated lipid (DOPE) decreased the uptake to approximately half of the observed values. This is likely due to the non-uniform packing of unsaturated lipid in the predominantly saturated lipid bilayer, which may affect the peptide presentation. It should be noted that due to our method for coupling traditional phospholipid molecules to peptides on the solid support, extra spacing is provided from the lipid anchor to the peptide due to the presence of succinic acid, ethanolamine, and a phosphoester bond. Thus, net linker length will vary depending on synthetic method used and optimal EG linker length may shift to a slightly shorter length when phospholipids are used in place of fatty acyl chains.

As an additional control experiment, we synthesized a PEGylated lipid with PEG350 and palmitic acid tails (PEG350-PA), incorporated the molecule into both non-targeted (95:10:5 HSPC:CHOL:PEG350) and liposomes targeted with HER2-pep conjugated to an EG12 linker (95:10:3:2 HSPC:CHOL:PEG350:HER2-pep-EG12-PA) and compared their efficacy to liposomes consisting of the commercially available PEG350-DSPE. The results show that incorporation of PEG350-PA does not change the behavior of either the targeting or non-targeting liposome relative to PEG350-DSPE. It is also noteworthy that zeta potential did not differ significantly between samples (see Table 1.2). Collectively, these results demonstrated that a shorter liposomal PEG coating than the standard PEG2000, in coordination with a shorter peptide EG-linker length than the standard EG45, provided much enhanced cellular targeting and uptake.

It is noteworthy that some groups have established that increasing the linker length in PEG2000 based liposome designs increases the uptake of liposomes. For example, Gabizon et al. showed that the use of PEG3350 (~76 EG units) as a linker significantly out performs the PEG2000 counterpart in folate targeted therapies (*Bioconjug. Chem.* 1999, 10, 289-298). Yamada et al. published similar findings with the use of a PEG5000 (~113 EG units) linker (*Clin. Cancer Res.* 2008, 14). However, these are special circumstances where the ligand in analysis possesses a very high affinity for the target receptor ($K_d$~1 nM) and multivalent interactions of the ligand with the cell surface receptors are likely not as essential compared to low to moderate affinity ligands. Similarly, when the targeting ligand is an antibody or antibody fragment, PEG2000 liposomal coating and PEG2000 linker may not cause a steric shielding problem since these targeting ligands are significantly larger (25-150 kDa) and readily water soluble compared to some targeting peptides. Thus, while a PEG2000 liposomal coating and a linker length of PEG2000 or longer may provide promising outcomes when the targeting ligand has very high affinity for the receptor or larger biomolecules such as antibodies are used as targeting ligands, our results demonstrated that a finer design is imperative when working with smaller, low to moderate affinity ligands such as peptides (e.g., peptides or oligopeptides having about 3 to about 100 amino acids).

Figure 7:
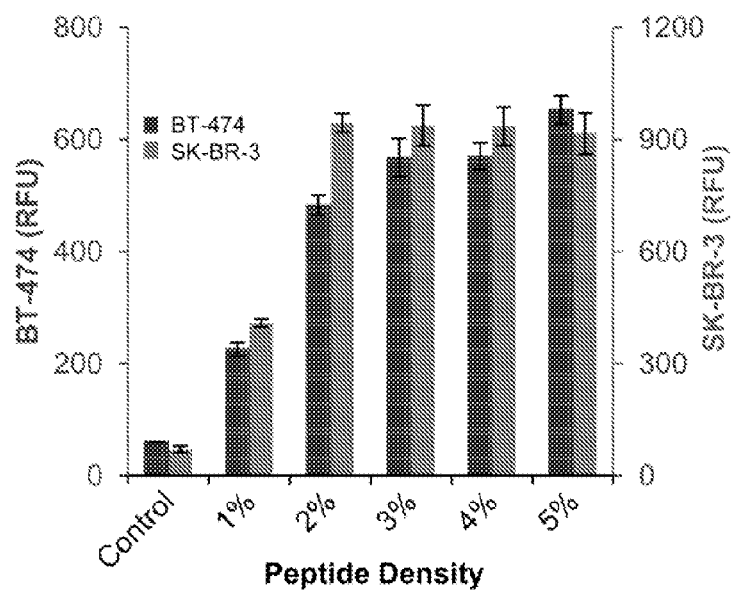
FIG. 7. Effect of peptide density on the cellular uptake of HER2-targeted liposomes. Liposomes with PEG350 coating and EG12 peptide linker were prepared at the indicated HER2-pep densities. The valency of HER2-pep was varied between 0-5% of the total lipid. Cellular uptake by BT-474 cells (left y-axis; left-side columns) and SK-BR-3 cells (right y-axis; right-side columns) were determined by flow cytometry. All experiments were done in triplicates and data represents means (±s.d.).

Evaluation of Peptide Valency on Nanoparticle Uptake. Our multifaceted synthetic strategy allows precise control over the exact number of targeting ligands per liposome. Therefore, we next examined the relationship between peptide valency and cellular uptake. We prepared liposomes with peptide densities of 0, 1, 2, 3, 4, and 5% of the total phospholipids (95:10:(5-n):n HSPC:CHOL:PEG350:HER2-pep-EG12-PA where n=0-5) to find the optimal conditions for maximal uptake using PEG350 as the liposomal coating and EG12 as the peptide linker (FIG. 7). For both the BT-474 and SK-BR-3 cell lines, the maximal uptake took place at ~2% and then reached a plateau. The observed plateau is likely due to the saturation of cellular surface receptors and the corresponding uptake mechanisms. Although these results establish 2% peptide density as the optimal density for maximum cellular uptake in vitro, this may not be directly transferable to in vivo studies. The high surface density of peptide on the liposome surface may accelerate clearance of the particles from blood circulation by opsonization and subsequent detection by the reticulo-endothelial system (RES). Ongoing research is currently evaluating the effect of peptide valency in tumor targeting and uptake in vivo.

Figure 8:
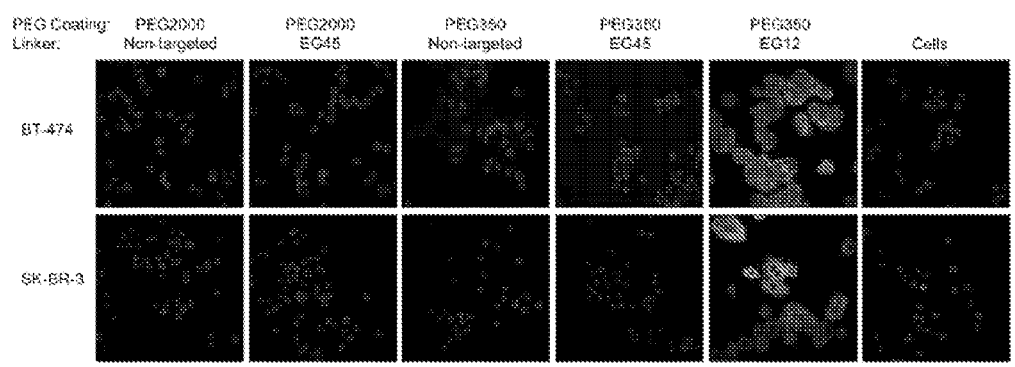
FIG. 8. Determination of cellular uptake via confocal microscopy. Rhodamine labeled liposomes with the indicated liposomal PEG coating and EG-linker were prepared and incubated with BT-474 (top) and SK-BR-3 (bottom) cell lines for 3 hours at 37° C. Non-targeted liposomes were included as controls. Internalization of nanoparticles was determined with a Nikon A1R confocal microscope using a 40× oil lens. Image acquisition was performed by Nikon Elements Ar software.

Validation of Cellular Uptake Results with Confocal Microscopy. While flow cytometry provides us with a powerful quantitative tool, it does not distinguish between cellular association and cellular internalization. To confirm cellular uptake and internalization of the nanoparticles by the HER2-overexpressing cells, confocal microscopy experiments were performed with rhodamine labeled liposomes (95:10:5 HSPC:CHOL:PEGX-DSPE for control liposomes and 95:10:3:2 HSPC:CHOL:PEGX-DSPE:HER2-pep for targeted liposomes). In both the BT-474 and SK-BR-3 cell lines, efficient uptake was observed when PEG350 liposomal coating and EG12 peptide linker was used, confirming the results observed with flow cytometry experiments (FIG. 8).

As seen before, the use of EG45 as the peptide linker, regardless of either PEG350 or PEG2000 liposomal PEG, provided no enhancement in cellular uptake. Additional imaging experiments, using confocal microscopy, were performed by labeling intracellular acidic vesicles (endosomes/lysosomes) with LysoTracker Red and examining the co-localization of fluorescein labeled nanoparticles (95:10:5 HSPC:CHOL:PEG350 for the control liposome and 95:10:3:2 HSPC:CHOL:PEG350:HER2-pep-EG12-PA for the targeted liposome). Significant internalization into lysosomes was observed with the EG12 liposomal formulation in both cell lines, with no internalization evident with a non-targeted liposome.

Figure 9:
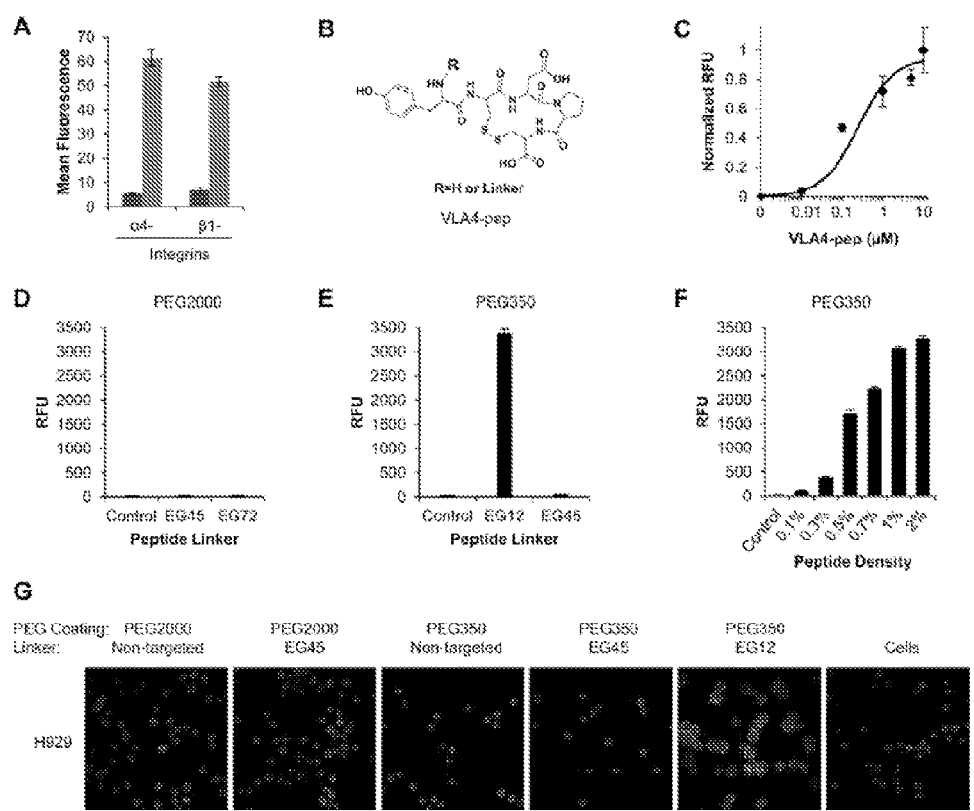
FIG. 9. Cellular uptake of VLA-4-targeted liposomes by VLA-4 expressing multiple myeloma cells. (A) NCI-H929 myeloma cells express VLA-4 subunits $\alpha_4$- and $\beta_1$-integrins as determined by flow cytometry. Right-side columns are primary antibodies and left-side columns are isotype controls. (B) Structure of VLA-4-antagonist peptide (VLA4-pep) is shown. (C) Cellular binding assays were performed using fluorescein labeled VLA4-pep and was detected by flow cytometry. Control experiments were done with fluorescein labeled non-specific peptide and the background binding was subtracted for each data point. VLA4-pep binds to NCI-H929 with an apparent $K_d$ of ~250 nM. D) Liposomes composed of PEG2000 coating and either EG45 or EG72 peptide linker were assayed for cellular uptake. E) Liposomes composed of PEG350 coating and either EG12 or EG45 peptide linker were assayed for cellular uptake. (F) The effect of peptide density on the uptake of VLA4-pep targeted liposomes prepared with PEG350 liposomal coating and EG12 peptide linker is shown. (G) Confocal microscopy images of rhodamine labeled liposome formulations with the indicated liposomal PEG coating and peptide EG-linker are shown. Non-targeted liposomes were included as controls. Internalization of nanoparticles was determined with a Nikon A1R confocal microscope using a 40× oil lens. Image acquisition was performed by Nikon Elements Ar software.
Figure 10:
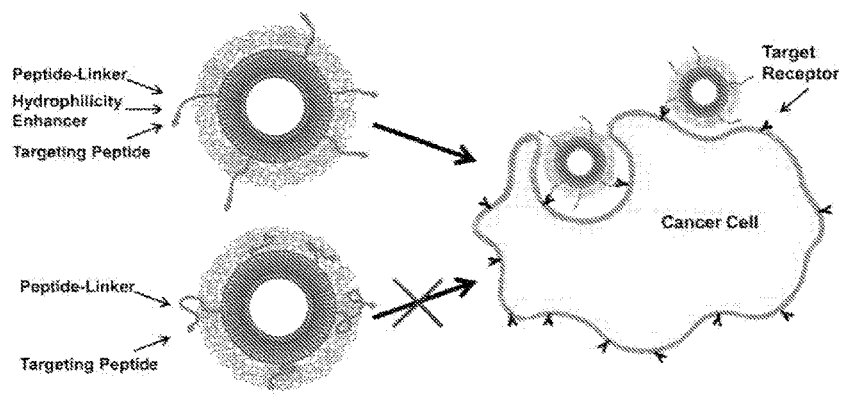
FIG. 10. Schematic illustration of the inability of nanoparticles (e.g., liposomes) to penetrate cancer cells when they lack an appropriate hydrophilicity enhancer, as described herein.

Effect of Liposomal PEG Coating and EG Linker Length on Cellular Uptake in VLA-4 Overexpressing Multiple Myeloma Model. To confirm that the conclusions derived from the experiments presented with HER2-targeting liposomes can be applied broadly to other peptide targeted liposomal delivery systems, we have undertaken a similar analysis with VLA-4 overexpressing multiple myeloma cells. It has been demonstrated that multiple myeloma cell lines express the VLA-4 subunits and $\alpha_4$- and $\beta_1$-integrins. First, we validated $\alpha_4\beta_1$ integrin expression in the NCI-H929 myeloma cell line (FIG. 9A). Several antagonistic peptides of VLA-4 have been identified and the cyclic peptide sequence, YCDPC (SEQ ID NO: 2) (VLA4-pep; FIG. 9B), has been shown to bind to VLA-4 expressing myeloma cells with specificity. We validated selective binding of VLA4-pep to NCI-H929 cells (FIG. 9C) and prepared VLA-4 targeted liposomal nanoparticles with varying liposomal PEG coating and peptide EG-linker lengths. We then analyzed cellular uptake in NCI-H929 myeloma cells by flow cytometry and confocal microscopy.

Our results obtained with myeloma cells demonstrated consistent results with the HER2 system. There was almost no enhancement in cellular uptake when PEG2000 coated liposomes (95:10:5 HSPC:CHOL:PEG2000 for control liposomes and 95:10:3:2 HSPC:CHOL:PEG2000:VLA4-pep for targeted liposomes) were used with EG45 or EG72 linkers (FIG. 9D). However, liposomes prepared using PEG350 coating with the shorter EG12 linker (95:10:5 HSPC:CHOL:PEG350 for control liposomes and 95:10:3:2 HSPC:CHOL:PEG350:VLA4-pep-EG12-PA for targeted liposomes) showed a dramatic enhancement of cellular uptake reaching up to ~100 fold (FIG. 9E). Similar to the HER2 system, uptake declined at longer linker lengths, completely diminishing at EG45. Uptake again reached a maximum and a plateau at 1-2% peptide density (95:10:(5-n):n HSPC:CHOL:PEG350:VLA4-pep-EG12-PA where n=0-2) (FIG. 9F).

Nanoparticle internalization (95:10:5 HSPC:CHOL:PEGX-DSPE for control liposomes and 95:10:3:2 HSPC:CHOL:PEGX-DSPE:VLA4-pep for targeted liposomes) was also confirmed by confocal microscopy (FIG. 9G). Co-localization studies with performed with the lysosomal marker Lysotracker Red and fluorescein labeled nanoparticles (95:10:5 HSPC:CHOL:PEG350 for the control liposome and 95:10:3:2 HSPC:CHOL:PEG350:VLA4-pep-EG12-PA for the targeted liposome) showed significant internalization of the liposomes targeted with the EG12 linker into lysosomes.

These results were consistent with the HER2 targeting system validating that the drawn conclusions can be applied broadly to other peptide targeted liposomes and are not disease, receptor, or peptide specific. It is noteworthy that the exact optimal linker length between different model systems may shift slightly depending on the intrinsic chemical properties of each peptide. For example, a peptide sequence with several hydrophobic residues may require a longer EG-linker to help increase its solubility and enhance its accessibility for its target receptor. Specific ligand-receptor interactions may also play a significant role in the optimal EG linker length depending on the depth of the binding pocket on the receptor for that particular peptide, since deeper pockets may require longer linker lengths for maximal targeting. Finally, although same trends were observed both for the VLA-4 and HER2 system regarding the optimal PEG coating, and EG-linker length, VLA-4 targeting was significantly more efficient than the HER2 targeting for cellular uptake as only 0.3% VLA-4-pep was required to achieve ~10 fold enhancement compared to 2% HER2-pep. This is most probably as a result of differences in the trafficking of the VLA-4 receptors in myeloma cells and HER2 receptors on the breast cancer cells. For this reasoning alone, the VLA-4 targeting system may prove more efficacious for an in vivo drug delivery application due to the significantly less peptide density required to achieve comparable uptake to the HER2 system.

Conclusions. Nanotechnology has been recognized by National Cancer Institute as a paradigm-changing opportunity with the potential to make significant breakthroughs in various applications including cancer diagnosis and therapy. Ligand-targeted nanoparticles, however, have not consistently delivered successful outcomes. One major factor that contributes to the observed inconsistencies is the commonly used synthetic methods to prepare targeted nanoparticles, which result in a heterogeneous surface with variable number of attachments and deactivated binding sites. Another major factor is the differences in the PEG coating of the particles, linkers used to conjugate the targeting ligands, as well as the type of targeting ligands. In this study, we have employed a multifaceted synthetic strategy to prepare ligand-targeted liposomal nanoparticles with high purity and precisely controlled stoichiometry of functionalities to evaluate the role of liposomal PEG coating, peptide EG-linker length, and peptide valency on cellular uptake.

Our studies demonstrated that the cellular uptake of nanoparticles can be significantly enhanced by generating liposomes consisting of PEG350 liposomal coating and a shorter peptide linker such as EG12. In particular, our results show that if the peptide linker is shorter than the liposomal PEG coating (i.e. EG6 linker), the peptide is hindered in its ability to bind to the receptor. As the linker length increases and the ligand begins to extend beyond the PEG coating, the peptide efficiently binds to its respective receptor, thereby enabling efficient uptake. In the HER2 overexpressing breast cancer model, EG12 and EG18 peptide linkers, which are 1.5 and 2.25 times longer than the liposomal PEG350 length when linear, enhanced cellular uptake by ~9 fold. As the linker length increased beyond these values, however, the binding of the ligand to the HER2 receptor decreased, returning to background levels at the EG45 (~PEG2000) linker length. These results and conclusions were established both in HER2-overexpressing breast cancer model, as well as VLA-4-overexpressing multiple myeloma model, demonstrating that our observations are not disease, receptor, or peptide specific. Taken together, the results presented here demonstrates the importance of using effective design elements as described herein, such as the appropriate peptide EG-linker length in coordination with the appropriate liposomal PEG coating, and optimal ligand density in efficient cellular uptake of liposomal nanoparticles.

Although one can argue that the in vitro evaluation of nanoparticulate systems may have reduced direct relevance in in vivo applications, as we demonstrated here, without cellular testing, it would be impossible to identify the design features for achieving enhanced cellular uptake. For successful in vivo administration, several factors will have a combined effect on the therapeutic outcome of targeted liposomal drug delivery systems such as: i) selective targeting of tumors; ii) uptake of nanoparticles by the tumor cell; iii) clearance by RES; and iv) tumor tissue penetration. Evaluation of the overall effect of these parameters on therapeutic outcomes is currently being assessed by incorporating therapeutic agents into our peptide-targeted nanoparticles and studying end points including tumor growth inhibition and systemic toxicity on several mouse models of cancers. In addition, we are analyzing how each of these factors contributes to the overall outcome.

The results of the in vivo studies may also vary depending on the inherent chemical properties of the selected peptide, expression level and trafficking of the targeted receptors, as well as the differences in the tumor models used. Additional liposome parameters such as the effect of cholesterol, bulk lipid selection (saturated/unsaturated phospholipids), and chemotherapeutic incorporation and loading techniques may have further implications in targeting efficiency and in vivo effectiveness. Each of these variables may be varied and modified for the compositions and methods described herein. Importantly, the nanoparticle synthetic strategy employed in this study addresses several major hurdles in nanoparticle preparation by providing precise control over the number of functionalities conjugated to each nanoparticle, thereby minimizing particle surface heterogeneity, polydispersity, and batch-to-batch variability in synthesis. This multifaceted synthetic strategy, combined with the identification of the optimal design elements for targeting various cancers, enables the successful applications of ligand-targeted liposomes in medicine.

Methods

Materials. N-Fmoc-amino acids, NovaPEG Rink amide resin, Wang resin, 2-(1H-Benzotriazole-1-yl)-1,1,3,3-tetramethyluronium hexafluorophosphate (HBTU), and bovine serum albumin (BSA) from EMD Millipore (Billerica, Mass.); Fmoc-(EG)$_n$-OH modification reagents from Quanta Biodesign (Powell, Ohio); palmitic acid, cholesterol (CHOL), N,N-diisopropylethylamine (DIEA), trifluoroacetic acid (TFA), triisopropylsilane (TIS), acetonitrile (ACN), 2-propanol, N,N-dimethylformamide (DMF), dichloromethane (DCM), and piperidine from Sigma-Aldrich (St. Louis, Mo.); fluorescein 5-isothiocyanate (FITC) from Toronto Research Chemicals (Toronto, Canada); secondary goat anti-human fluorescein conjugated antibody from Jackson ImmunoResearch (West Grove, Pa.); all methoxy PEG-DSPE (PEG-DSPE) lipids, DSPE-PEG2000-NH$_2$, fluorescein PE, and lissamine rhodamine B PE from Avanti Polar Lipids, Inc (Alabaster, Ala.). Humanized mouse mAb Herceptin was provided by Dr. Rudolph Navari (Indiana University School of Medicine).

Synthesis of Peptides and Peptide-EG-Lipid Conjugates. Ligands were synthesized using Fmoc chemistry on a solid support using Rink amide or Wang resin. Residues were activated with HBTU and DIEA in DMF for 3 minutes and coupling efficiency was monitored using Keiser test. The Fmoc protected residues were de-protected with three applications of 20% piperidine in DMF for 3 minutes each time. The molecules were cleaved from the solid support using 94/2.5/2.5/1 TFA/H$_2$O/EDT/TIS mixture twice for 30 minutes each time. We purified the molecules using RP-HPLC on an Agilent (Santa Clara, Calif.) 1200 series system with a semi-preparative Zorbax C$_{18}$ column or Zorbax C$_3$ column with either acetonitrile or isopropanol gradients in the mobile phase. We monitored the column eluent with a diode array detector allowing a spectrum from 200 to 400 nm to be analyzed. The purified product was characterized using a Bruker Autoflex III Smartbeam Matrix Assisted Laser Desorption Ionization Time of Flight Mass Spectrometer (MALDI-TOF-MS, Billerica, Mass.). Peptide cyclization through disulfide bond formulation was performed in DMF with DIEA under stirring overnight.

Characterization of Liposomes. Particle size was measured using DLS analysis via the 90Plus Nanoparticle Size Analyzer (Brookhaven Instruments Corp., Long Island, N.Y.), using 658 nm light observed at a fixed angle of 90° at 20° C. Zeta potential was measured using the ZetaPlus zeta potential analyzer (Brookhaven Instruments Corp.).

Cell Culture. SK-BR-3 and NCI-H929 cell lines were obtained from American Type Culture Collection (Rockville, Md.). BT-474 cells were a generous gift from John Park at the University of California San Francisco. SK-BR-3 cells were cultured in McCoy's 5A (ATCC) media, while BT-474 and NCI-H929 cell lines were cultured in RPMI 1640 media (Cellgro, Manassas, Va.). All lines were supplemented with 10% fetal bovine serum (FBS), 2 mM L-glutamine (Gibco, Carlsbad, Calif.), 100 U/mL penicillin, and 100 μg/mL streptomycin (Gibco). NCI-H929 cells were supplemented with an additional 10% FBS and 55 μM 2-mercaptoethanol.

HER2 or VLA-4 Expression Analysis and Cell-Based Peptide Binding Assays. For antibody binding assays, cells were incubated with the primary antibody in binding buffer (1.5% BSA in PBS pH 7.4) on ice for 1 hour and were washed twice. Fluorescein conjugated secondary antibody was added for 1 hour on ice, samples were washed, and analyzed on Guava easyCyte 8HT flow cytometer (Millipore). For cell-based peptide binding assays, cells were incubated with increasing concentrations of fluorescein-conjugated peptides for 2 hours on ice. Samples were washed twice and analyzed on Guava easyCyte 8HT flow cytometer.

Liposome Preparation. Liposomes were prepared by dry film hydration as described previously (Olson et al., *Biochim. Biophys. Acta* 1979, 557). Briefly, a lipid mixture of chloroform stocks was prepared and dried to form a thin film using nitrogen gas then placed under vacuum overnight to remove residual solvent. The lipid films were hydrated at 65° C. in PBS pH 7.4, gently agitated, and extruded at 65° C. through a 0.1 μM polycarbonate filter. Liposomes all adhered to the following formula 95:10:(5-n):n HSPC:CHOL:PEGX-DSPE:peptide-EG-lipid conjugate, where n was varied between 0-5 to control the peptide density and X represents PEG molecular weights, including 350, 550, 750, 1000, or 2000.

In Vitro Liposome Uptake and Binding Assays. $1 \times 10^5$ cells/well were plated 24 hours prior to each experiment in a 24 well dish. Liposomes were added at 100 μM phospholipid concentration and incubated for 3 hours at 37° C. 0.2% fluorescein PE was added as a fluorescent marker to each liposomal formulation. For adherent cells, after incubation, cells were washed 3 times with PBS, trypsinized, and analyzed via flow cytometry. For suspension cells, after incubation, cells were washed 3 times with PBS and analyzed via flow cytometry. For binding assays, adherent cells were scraped from the surface of a confluent dish, placed in growth media, and incubated on ice for 30 minutes. Liposomes were added at variable concentrations and incubated for 2 hours on ice. After incubation, cells were washed 3 times with PBS and analyzed via flow cytometry.

Confocal Microscopy. For breast cancer cells, $1\times10^5$ cells/well were plated 24 hours prior to each experiment onto 12 mm diameter borosilicate glass coverslips in a 24 well dish. Liposomes were added at 100 μM phospholipid concentration and incubated for 3 hours at 37° C. 1% rhodamine PE was added as a fluorescent marker to each liposomal formulation. After incubation, cells were washed 3 times with PBS and fixed with 4 w/w % paraformaldehyde (PFA). Coverslips were mounted on microscope slides with VectaShield antifade/DAPI (Vector Labs, Burlingame, Calif.). For suspension cells, after incubation, cells were washed 3 times and cytospinned onto slides before fixing and coverslip mounting. For co-localization studies, 1% fluorescein PE was added as a fluorescent marker to each liposomal formulation. After 3 hours of liposome incubation, the cells were washed 3 times with PBS and incubated with 50 nM Lysotracker Red (Molecular Probes, Carlsbad, Calif.) for 30 minutes at 37° C. to allow internalization. Cells were washed 3 times, fixed in PFA, and mounted on glass slides using Prolong Gold Antifade Reagent (Molecular Probes). Cells were visualized by Nikon A1R confocal microscope with a 40× oil lens (Nikon Instruments, Melville, N.Y.). Image acquisition was performed by Nikon Elements Ar software (Nikon).

Example 2

Enhanced Cellular Uptake of Peptide-Targeted Nanoparticles Through Increased Peptide Hydrophilicity and Optimized Ethylene Glycol Peptide-Linker Length Polyethylene glycol (PEG) coated nanoparticles are widely used drug delivery vehicles for the selective delivery of therapeutic agents, notably for cancer therapy. The PEGylation of both liposomal and micellar drug formulations results in nanoparticles with increased stability, bioavailability, and tumor accumulation due to the enhanced permeability and retention (EPR) effect, which is known as passive targeting. In an effort to improve tumor targeting and cellular uptake, nanoparticles can also be functionalized with active targeting molecules such as antibodies, antibody fragments, small molecules, and peptides (Sofou et al., *Expert Opin. Drug Deliv.* 2008, 5, 189-204; Torchilin, *Nat. Rev. Drug Discov.* 2005, 4, 145-160; Dubey et al., *J. Drug Target.* 2004, 12, 257-264; Zhao et al., *Expert Opin. Drug Deliv.* 2008, 5). To date, active targeting approaches, however, have not shown consistently successful outcomes in terms of drug delivery. This discrepancy has in part been attributed to the differences in the type of disease models and target receptors. There is, however, also a strong prevalence that differences in nanoparticle design including the synthetic methods used to prepare the nanoparticles, the linkers used to conjugate the targeting ligands, the type of targeting ligand, as well as the length and density of liposomal PEG coating significantly contribute to the apparent inconsistent outcomes.

PEG2000 (a mean of ~45 repeating units of ethylene glycol: EG45) is the polymer of choice for coating nanoparticles to enhance in vivo circulation by inhibiting immune system detection. In order to prepare ligand-targeted nanoparticles, targeting ligands have been traditionally grafted onto the distal end of PEG2000 or longer linkers such as PEG3350 and PEG5000 to effectively present the ligands above the PEG coating. However, long PEG polymers do not preserve a linear conformation in the aqueous phase; instead, they fold within themselves to form mushroom-like, globular structures. This unique morphology significantly lowers the percent of accessible ligand by burying it within the PEG coating and sterically hindering the association of the ligand-targeted nanoparticles with their target receptor.

Successful demonstrations of ligand targeted nanoparticles with such longer PEG chains have been largely observed with receptor-ligand pairs that exhibit high binding affinity ($K_d \approx$ low nM), such as the folic acid-folate receptor and antibody-antigen interactions. To the contrary, recent studies have demonstrated that for low to moderate affinity ligands, shorter EG ligand-linkers can yield more favorable results, highlighting the significance of ligand linker length and ligand-receptor physiochemical properties (see Example 1 above). Short EG linkers adopt a more linear morphology in the aqueous phase when compared to longer PEG linkers, thereby demonstrating reduced entropic penalties upon binding and resulting in improved ligand activity which drives increased cellular binding and subsequent uptake of targeted liposomes.

Cyclic peptides are gaining popularity as targeting ligands because of the advantages they provide including ease of preparation, lower cost, lower antigenicity, decreased opsonization, and increased resistance to enzymatic degradation in vivo. Peptides can be conjugated to lipids to generate amphiphilic molecules, which can be readily incorporated into liposomes or micellar nanoparticles during their formation, allowing for precise control over the stoichiometry of targeting ligands with high reproducibility. However, biophysical and chemical properties of peptides may affect their efficacy as targeting agents in a nanoparticle platform. For example, hydrophobic peptide sequences can promote nanoparticle aggregation or become buried in the lipid segment of the liposome or micelle, reducing ligand accessibility and increasing nanoparticle size. Limited chemical stability with respect to either the synthetic techniques for creating nanoparticles or physiological pH and temperature can also compromise peptide activity. These combined factors may limit the therapeutic potential of peptide-targeted nanoparticles.

In this Example, we demonstrated that the targeting efficacy of peptide-targeted nanoparticles can be dramatically enhanced by i) increasing the hydrophilicity of the targeting peptide sequence and ii) systematic optimization of the EG peptide-linker length. To validate our strategy, first we evaluated the effect of peptide hydrophilicity and EG linker length on the cellular uptake of Very Late Antigen-4 (VLA-4; also known as $\alpha_4\beta_1$ integrin) targeted liposomes and micelles. In our approach, we used a short cyclic peptide antagonist of VLA-4 as the targeting ligand and identified the optimal design elements for maximum cellular uptake by VLA-4-overexpressing multiple myeloma cells. We then validated our findings by applying and evaluating the optimized design elements in a Human Epidermal Growth Factor Receptor 2 (HER2) overexpressing breast cancer model. In both disease models, we consistently demonstrated that cellular uptake of nanoparticles is significantly enhanced by increasing the peptide hydrophilicity through the addition of a short oligolysine chain ($K_N$, where K refers to the lysines and N is number of repeat units) adjacent to the peptide targeting ligand and optimizing the EG peptide-linker to compromise between peptide presentation beyond the PEG cloud and compensation of entropic losses from long linkers. These results established the significance of using the right design elements in the efficient targeting of tumors.

Results and Discussion

Figure 11:
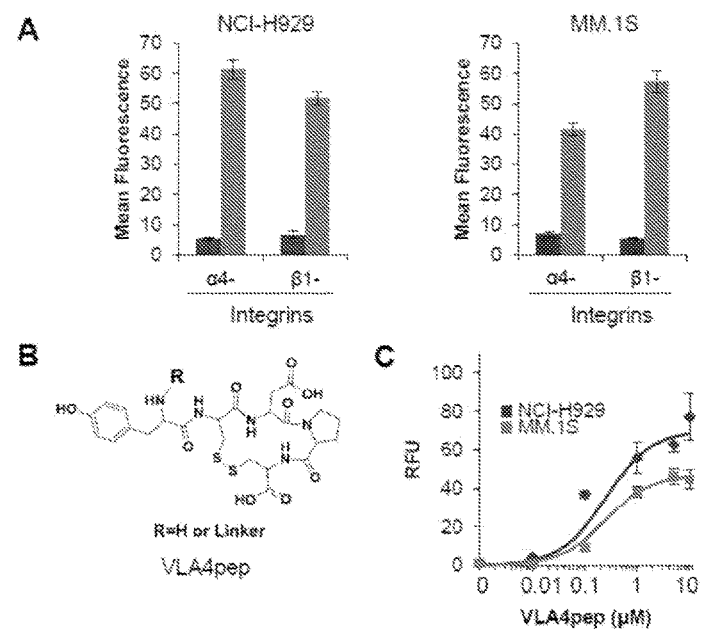
FIG. 11. VLA-4 expression in multiple myeloma cancer cells and identification of a VLA-4-antagonist peptide. (A) NCI-H929 and MM.1S myeloma cells express VLA-4 subunits $\alpha_4$- and $\beta_1$-integrins as determined by flow cytometry. Right columns are primary antibodies and left columns are isotype controls. (B) Structure of VLA-4-antagonist peptide (VLA4pep) is shown. (C) Cellular binding assays were performed using fluorescein labeled VLA4pep and binding was detected by flow cytometry (NCI-H929, diamonds; MM.1S, squares).

Validation of the Selective Binding of a VLA-4-Antagonist Peptide to VLA-4-Overexpressing Multiple Myeloma Cells. We validated the $\alpha_4\beta_1$ integrin expression levels in NCI-H929 and MM.1S multiple myeloma cell lines via flow cytometry by using fluorescently labeled, integrin specific antibodies (FIG. 11A). Due to the critical role of VLA-4 in cancers, several antagonistic peptides have been identified. The cyclic peptide sequence, YCDPC (SEQ ID NO: 2) (VLA4pep; FIG. 11B), has been shown to bind to VLA-4 expressing myeloma cells with specificity and was therefore selected for this study (Kiziltepe et al., *Blood Cancer J.* 2012, 2, e64). We validated selective binding of VLA4pep to NCI-H929 and MM.1S cells by labeling VLA4pep with fluorescein and analyzing its binding to cells by flow cytometry (FIG. 11C). Control experiments performed with a fluorescein labeled scrambled peptide showed only minimal background binding, which was subtracted from each data point. VLA4pep bound to both myeloma cell lines with an apparent $K_d$ of 250 nM.

Figure 12:
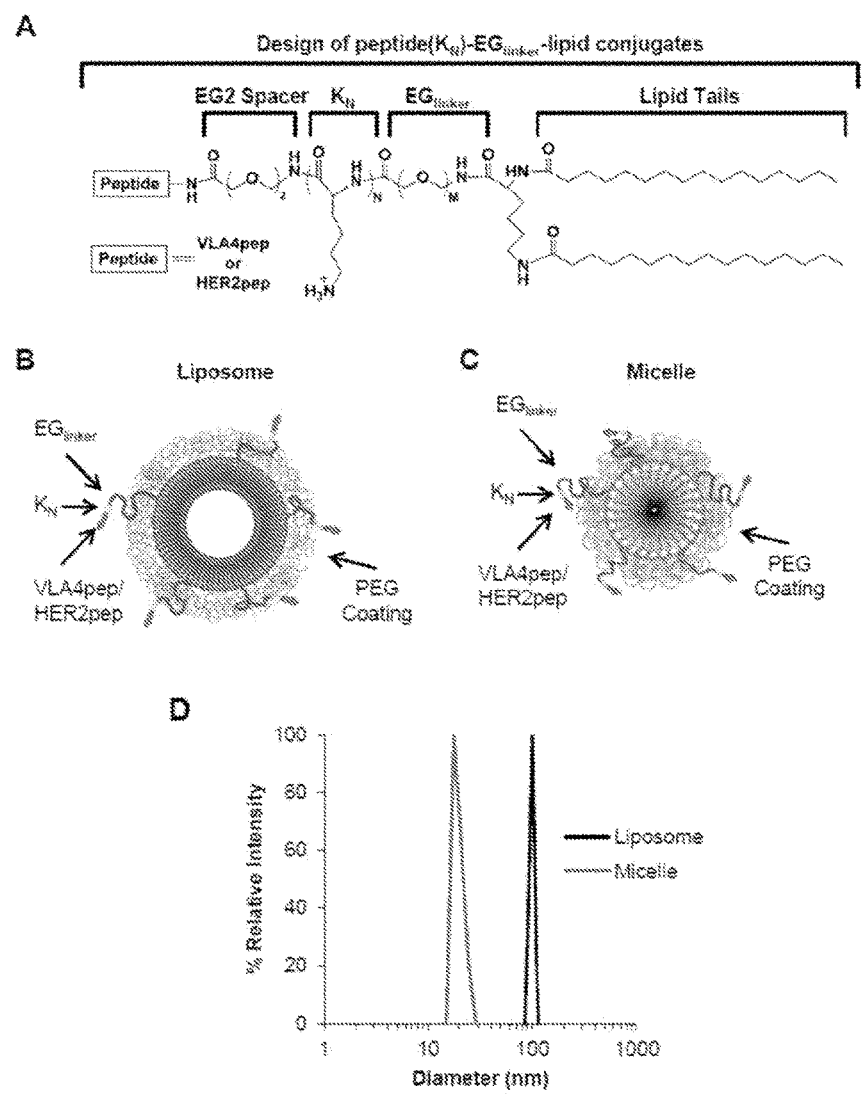
FIG. 12. Design and characterization of peptide conjugated nanoparticles. (A) Structure of peptide($K_N$)-EG$_{linker}$-lipid conjugates with variable oligolysine ($K_N$) content and EG peptide-linker lengths including EG6, EG12, EG18, EG24, EG30, EG36, and EG72. (B) Schematic of the peptide-targeted liposomes. (C) Schematic of peptide-targeted micelles. (D) Dynamic light scattering analysis of nanoparticles (left peak=micelles; right peak=liposomes).

Design and Preparation of Peptide-Targeted Liposomes and Micelles. The physiochemical properties of peptide-based targeting ligands and the length of the EG peptide-linker are important parameters for actively targeted nanoparticles. To assess the effect of peptide hydrophilicity and EG peptide-linker length on the cellular uptake of peptide-targeted nanoparticles, we synthesized several peptide($K_N$)-$EG_{linker}$-lipid conjugates (FIG. 12A). In our design, the conjugates consist of i) a receptor specific peptide (i.e. VLA4pep), ii) an EG2 spacer (which can be varies from EG1 to about EG4), iii) a short oligolysine chain ($K_N$, where K refers to the lysines and N is number of repeat units) to increase hydrophilicity, iv) an EG peptide-linker, and v) two hydrophobic fatty acid chains to enable insertion into the lipid bilayer of the liposomes or associate with the lipid core of micelles. An EG2 spacer minimizes interactions between the peptide and the oligolysine chain ($K_N$), and EG peptide-linker, which varies from EG6 to EG72, aids in presenting the targeting peptide beyond the PEG cloud on the nanoparticles to enable binding to the target receptor.

Figure 13:
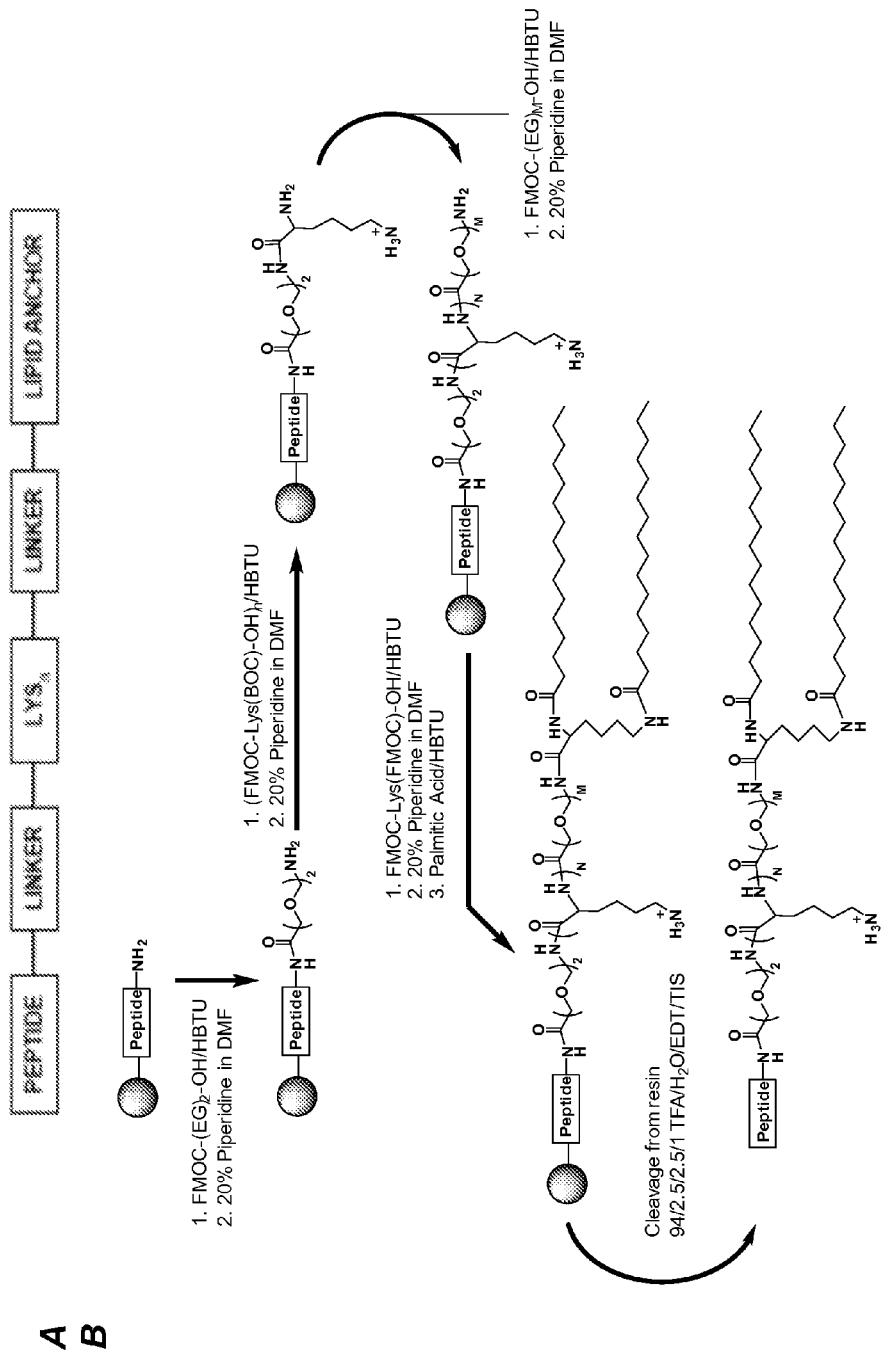
FIG. 13. Synthesis of peptide conjugated lipid amphiphilic molecules. (A) Schematic of a peptide-EG-lipid conjugate targeting ligand, according to an embodiment of the invention. (B) Schematic of the synthetic steps for the synthesis of amphiphilic peptide($K_N$)-EG$_{linker}$-lipid with variable oligolysine ($K_N$) content and EG peptide-linker length, including EG6, EG12, EG18, EG24, EG30, EG36, EG45, and EG72.

The two fatty acid chains were coupled to the EG linker via first coupling L-lysine to the N-terminus of the EG linker and then coupling the fatty acids to the $\alpha$- and $\epsilon$-amines of the L-lysine residue to generate the hydrophobic tail of the peptide($K_N$)-$EG_{linker}$-lipid conjugate. Palmitic acid was selected in lieu of a conventional carboxylic acid terminated phospholipid, such as DPPE-GA or DSPE-GA, due to its greater chemical stability as it lacks the phosphoester bond and increased solubility in typical solid phase reagents such as DCM and DMF. The synthesis of the peptide($K_N$)-$EG_{linker}$-lipid conjugates was carried out entirely on a solid support platform using standard Fmoc chemistry protocols. Completed products were then cleaved from the resin and purified via RP-HPLC. Peptide cyclization through disulfide bond formation was performed in DMF with DIEA at room temperature while stirring overnight. Full synthetic scheme, mass spectrometry data, and product yields of the synthesized peptide($K_N$)-$EG_{linker}$-lipid conjugates are provided (see FIG. 13, and Table 1.1 in Example 1 above).

Liposomes (FIG. 12B) were prepared using purified peptide($K_N$)-$EG_{linker}$-lipid conjugates, PEG2000-DSPE, HSPC, and cholesterol, while micelles (FIG. 12C) were prepared with peptide($K_N$)-$EG_{linker}$-lipid conjugates and PEG2000-DSPE to yield nanoparticles around 100 nm and 15-20 nm, respectively, as determined by dynamic light scattering (DLS) (FIG. 12D). The components were mixed at specific stoichiometries (molar ratios) to achieve precise control over the number of functional ligands on each particle, maintaining reproducibility in nanoparticle production. Note that for convenience, throughout the description and examples, reference to PEG2000 or PEG350 as components of a micelle or liposome refers to a pegylated lipid such as PEG2000-DSPE or PEG350-DSPE.

The liposomes were sized via extrusion through a polycarbonate membrane while micelles were formed by solvent evaporation and sonication, at lipid concentrations above the critical micelle concentration (CMC) of 5-10 µM to create relatively monodisperse particles with ~90 lipid molecules per micelle. Lissamine rhodamine B PE or fluorescein PE was incorporated into the nanoparticles for cellular uptake experiments. Regardless of the nanoparticle formulation, including the addition of fluorescent imaging agents or targeting moieties, the mean diameter of the particles remained constant (see Table 1.2 for particle size and zeta potential analysis of select nanoparticle formulations).

Figure 14:
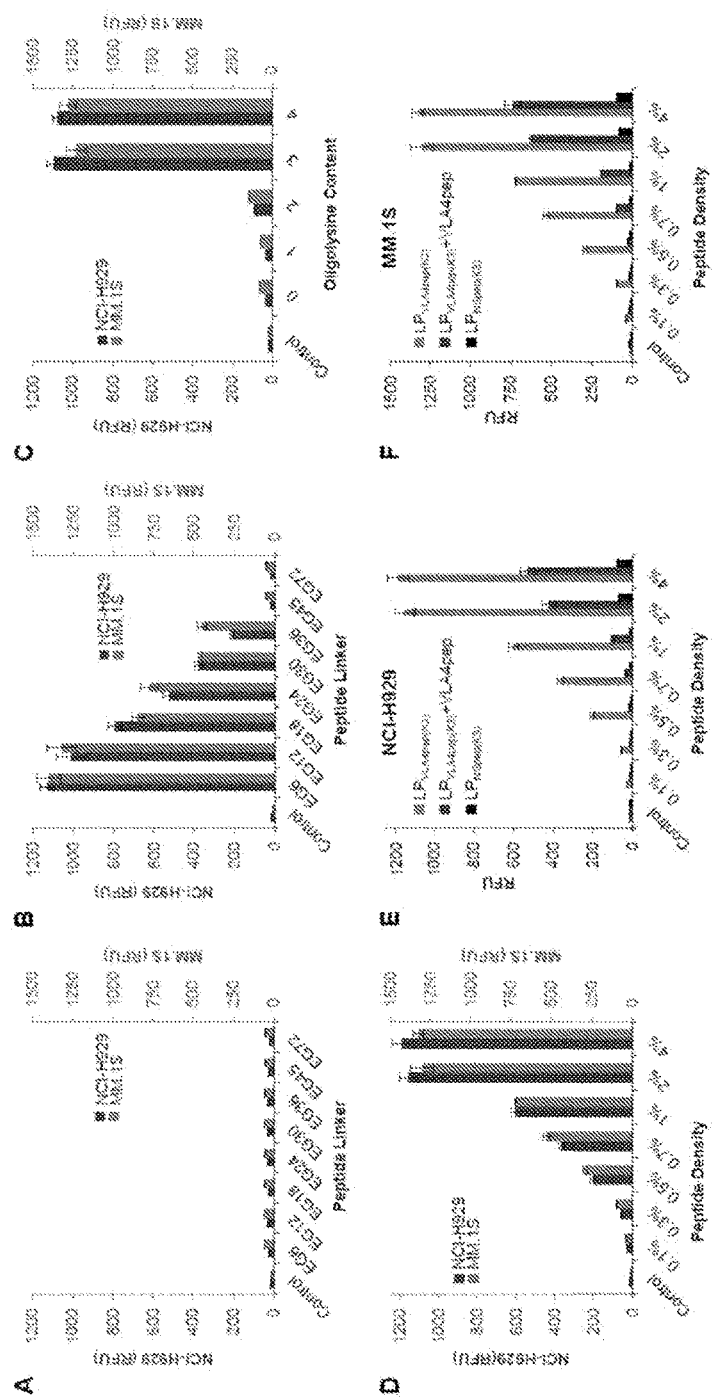
FIG. 14. Effect of EG peptide-linker length, oligolysine ($K_N$) content, and peptide valency on the cellular uptake of VLA-4-targeted liposomes. (A) The effect of EG peptide-linker length on the cellular uptake of liposomes targeted with VLA4pep($K_0$) was evaluated with NCI-H929 (left columns) and MM.1S (right columns) cells by flow cytometry. The EG linker lengths investigated include: EG6, EG12, EG18, EG24, EG30, EG36, EG45, and EG72. (B) The effect of EG peptide-linker length on the uptake of liposomes targeted with VLA4pep($K_3$). Cellular uptake by NCI-H929 (left columns) and MM.1S (right columns) cells was determined by flow cytometry. (C) The effect of oligolysine chain length ($K_N$) was evaluated using liposomes targeted with VLA4pep($K_N$) using an EG6 peptide-linker. Cellular uptake by NCI-H929 (left columns) and MM.1S (right columns) cells was evaluated by flow cytometry. The $K_N$ chain length varied from N=0-4. (D) The effect of peptide valency of the cellular uptake of liposomes targeted with VLA4pep($K_3$) (LP$_{VLA4pep(K3)}$) with an EG6 peptide-linker was determined. Peptide density was varied between 0-4% of the total lipid and cellular uptake was evaluated for NCI-H929 (left columns) and MM.1S (right columns). (E) Competition experiments performed with excess free VLA4pep were performed to determine specificity of uptake for NCI-H929 cells. LP$_{VLA4pep(K3)}$, left column; LP$_{VLA4pep(K3)}$+VLA4pep, middle column. Non-specific peptide (NSpep) was also incorporated into liposomes (LP$_{NSpep(K3)}$) as a control (right column). (F) Competition experiments performed with excess free VLA4pep were performed to determine specificity of uptake for MM.1S cells. LP$_{VLA4pep(K3)}$, left column; LP$_{VLA4pep(K3)}$+VLA4pep, middle column. Non-specific peptide (NSpep) was also incorporated into liposomes (LP$_{NSpep(K3)}$) as a control (right column). All experiments were done in triplicates and data represents means (±s.d.).

The Effect of EG Peptide-Linker Length, Oligolysine Content ($K_N$), and Peptide Valency on the Cellular Uptake of VLA-4-Targeted Liposomes. The length of the EG peptide-linker connecting the targeting peptide to the lipid anchor is an important parameter for consideration in the design of peptide-targeted liposomes. Therefore, to evaluate this, we examined the effect of the EG peptide-linker length on cellular uptake of liposomes by using VLA4pep with no lysines (VLA4pep($K_0$)) tethered to a variety of linkers including EG6, EG12, EG18, EG24, EG30, EG36, EG45, and EG72 (FIG. 14A). Targeted liposomes were formulated as 93:10:5:2 HSPC:CHOL:PEG2000:VLA4pep($K_0$) with a non-targeted control of 95:10:5 HSPC:CHOL:PEG2000. Our results showed that regardless of EG linker length, there was only minimal uptake despite the high density of VLA4pep($K_0$) on the surface of the liposomes. Given that the research standard for preparing ligand targeted liposomes has traditionally involved attaching the targeting ligand onto the distal end of functionalized PEG polymers that are at least 45 EG units in length (PEG2000), this observation was unexpected. We attributed the lack of uptake to limited peptide accessibility, as the shorter EG linkers may not effectively expose the peptide beyond the PEG2000 coating and the longer EG linkers may bury the peptide in the PEG2000 coating due to the globular, mushroom-like morphology.

In order to increase cellular uptake, we hypothesized that the binding activity of VLA-4-targeted liposomes can be enhanced by increasing the hydrophilicity of the peptide targeting sequence through the incorporation of oligolysine ($K_N$) residues adjacent to the peptide (FIG. 12A). Therefore, we next evaluated the effect of the chemical properties of the targeting peptide, specifically its hydrophilicity, in coordination with the EG peptide-linker length to increase peptide availability to bind to its target receptor. For this, we synthesized VLA4pep with 3 lysine residues (VLA4pep ($K_3$)) and examined the effect of EG linker length on cellular uptake by tethering VLA4pep($K_3$) to EG linkers ranging from EG6-EG72 (FIG. 14B). Targeted liposomes were formulated as 93:10:5:2 HSPC:CHOL:PEG2000:VLA4pep ($K_3$). Our results demonstrated a dramatic increase in cellular uptake of liposomes, with maximum enhancements of ~75 and ~85 fold for NCI-H929 and MM.1S myeloma cell lines, respectively, using the EG6 linker. The addition of the oligolysine chain ($K_3$) simultaneously increased hydrophilicity and improved exposure beyond the PEG coating, increasing the display of the peptide in the aqueous portion of the liposome exterior and enhancing the availability of VLA4pep to bind to its target receptor. The uptake enhancement declined with increasing EG peptide-linker length, completely diminishing with EG45 and EG72 linkers.

Given that longer linkers, such as EG45 (PEG2000), have traditionally been used for ligand-targeted nanoparticles, it is remarkable that shorter peptide-linkers, such as EG6, yielded greater enhancements in cellular uptake. Longer PEG linkers provide a steric hindrance to ligand binding due to the mushroom like globular structure and provide less thermodynamically favorable interactions. Conversely, shorter linkers can restrict the translational and conformational freedom of the peptide, thereby reducing the overall entropic loss when the liposome binds to the cell. Furthermore, a shorter linker can adopt a more linear conformation, unlike a longer linker. Although PEG2000 consists of a mean of 45 EG repeat units which is ~16 nm in length when linear, hydration studies have shown that PEG2000 actually only extends ~3-5 nm from the surface of the liposome due to the mushroom-like structure. The EG6 peptide-linker extends a net distance of ~5.5 nm from the lipid head to VLA4pep, which is sufficiently long enough to span through the PEG2000 cloud when linear. This provides a more favorable interaction, which results in improved cellular binding and subsequent uptake.

Next, to assess the optimal oligolysine chain length, we synthesized VLA4pep($K_N$) with an EG6 peptide-linker, varied N from 0-4, and evaluated cellular uptake (FIG. 14C). Targeted liposomes were formulated as 93:10:5:2 HSPC: CHOL:PEG2000:VLA4pep($K_N$). Our results showed minimal cellular uptake with the incorporation of 0-2 lysine residues, but the inclusion of 3 lysines resulted in a significant enhancement and reached a plateau for cellular uptake.

Next, we examined the effect of peptide valency on cellular uptake. We prepared targeted liposomes containing VLA4pep($K_3$) with an EG6 linker (95-x:10:5:x HSPC: CHOL:PEG2000:VLA4pep($K_3$), where x represents the peptide valency) to find the optimal conditions for maximal uptake (FIG. 14D). For both myeloma cell lines, the uptake reached a maximum and a plateau at 2% peptide density, likely due to the saturation of cellular uptake mechanisms. Competition experiments performed with excess free VLA4pep demonstrated efficient inhibition of uptake, establishing the specificity of receptor-ligand interactions and the involvement of VLA-4 receptor in the uptake of targeted liposomes (FIGS. 14E and 14F). In an additional control experiment, only negligible uptake was observed with liposomes that incorporated a non-specific peptide (NS) with 3 lysines and EG6 linker (NSpep($K_3$)), further establishing the selectivity and specificity of the uptake observed for VLA-4-targeted liposomes.

Figure 15:
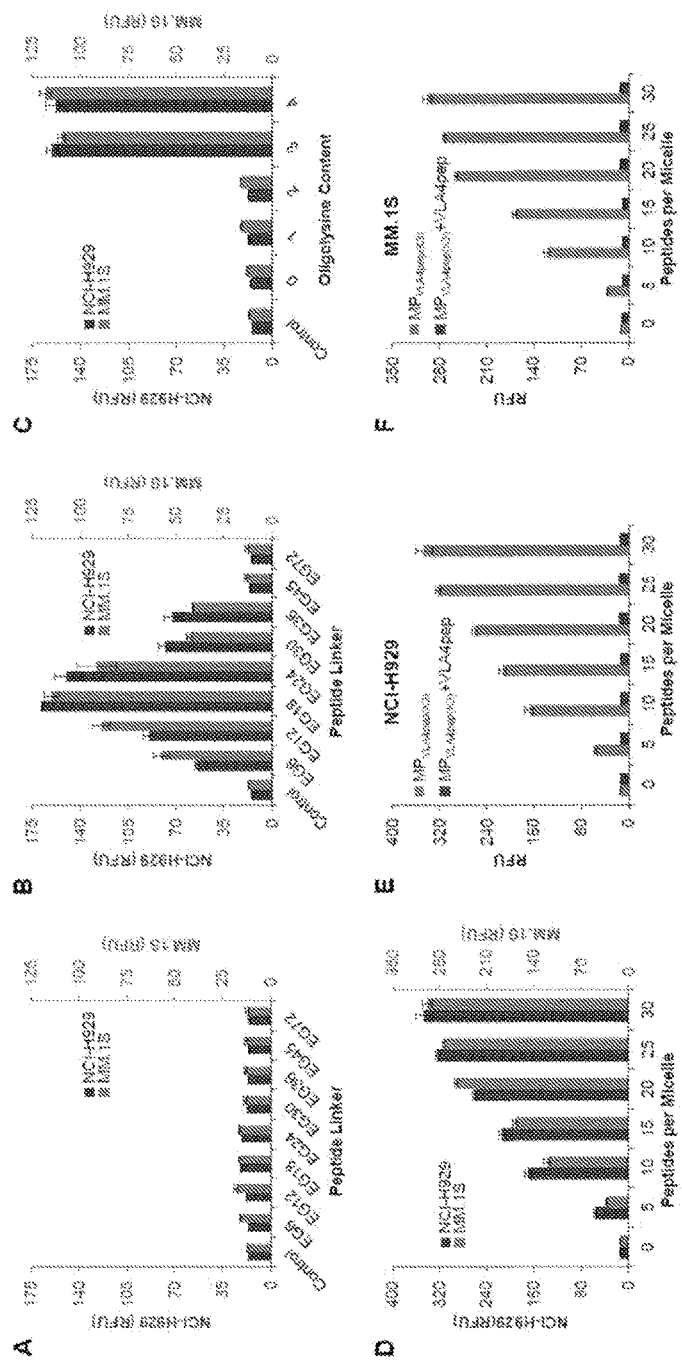
FIG. 15. Effect of EG peptide-linker length, oligolysine ($K_N$) content, and peptide density on the cellular uptake of VLA-4-targeted micelles. (A) The effect of EG peptide-linker length on the cellular uptake of micelles targeted with VLA4pep($K_0$) was evaluated using NCI-H929 (left columns) and MM.1S (right columns) cells by flow cytometry. The EG peptide-linker lengths investigated include: EG6, EG12, EG18, EG24, EG30, EG36, EG45, and EG72. (B) The effect of EG peptide-linker length on the uptake of micelles targeted with VLA4pep($K_3$). Cellular uptake by NCI-H929 (left columns) and MM.1S (right columns) cells was determined by flow cytometry. (C) The effect of oligolysine chain length ($K_N$) was evaluated using micelles targeted by VLA4pep($K_N$) with EG18 peptide-linker. Cellular uptake by NCI-H929 (left columns) and MM.1S (right columns) cells was evaluated by flow cytometry. The $K_N$ content varied from N=0-4. (D) The effect of peptide valency of the cellular uptake of micelles targeted with VLA4pep($K_3$) (MP$_{VLA4pep(K3)}$) using an EG18 peptide linker was determined. Peptide density was varied from 0-30 peptides per micelle and cellular uptake was evaluated for NCI-H929 (left columns) and MM.1S (right columns). (E) Competition experiments performed with excess free VLA4pep (right columns) were performed to determine specificity of uptake for NCI-H929 cells. (F) Competition experiments performed with excess free VLA4pep (right columns) were performed to determine specificity of uptake for MM.1S cells. All experiments were done in triplicates and data represents means (±s.d.).

Effect of EG Peptide-Linker Length, Oligolysine Content ($K_N$), and Peptide Valency on the Cellular Uptake of VLA-4-Targeted Micelles. In order to further validate our targeting strategy and determine if the results obtained with the liposomes can be applied broadly to other drug delivery systems, we evaluated our approach with micellar nanoparticles. Although micelles are another type of lipid-based drug delivery vehicle, their smaller size (~15-20 nm diameter), decreased number of lipids per particle (~90 lipids per micelle compared to ~80,000 lipids per 100 nm diameter liposome), and absence of a lipid bilayer provide noticeable differences compared to liposomes. To evaluate the effect of the EG peptide-linker length on the cellular uptake of VLA-4-targeted micelles, we formulated micelles that incorporated VLA4pep with no lysines (VLA4pep($K_0$)) and variable EG linker lengths of EG6, EG12, EG18, EG24, EG30, EG36, EG45, and EG72 (FIG. 15A). Targeted micelles were formulated as 80:10 PEG2000:VLA4pep($K_0$).

Similar to the liposomes, we did not observe improved cellular uptake through the EG peptide-linker length modification alone. However, when we increased the hydrophilicity of VLA4-pep through the addition of 3 lysines (VLA4pep($K_3$)) and evaluated the cellular uptake of micelles targeted with VLA4pep($K_3$) (80:10 PEG2000: VLA4pep($K_3$)), we observed a bell shaped distribution with respect to EG peptide-linker length, with maximum uptake using an EG18 linker (FIG. 15B).

These results are similar to the ones observed with liposomes as increasing the hydrophilicity of the peptide ligand significantly increased cellular uptake. In addition, traditional formulations using an EG45 or EG72 peptide linker showed negligible uptake for both myeloma cells lines. One notable difference was the optimal EG linker length for the liposomes (EG6, net extension distance ~5.5 nm) versus micelles (EG18, net extension distance ~10.1 nm), which can be due to the PEG surface morphology and curvature of the micelles. In the micellar structure, PEG2000 adopts a more brush-like structure as opposed to the mushroom shape in the liposomes, extending the PEG cloud further away from the lipid layer. Furthermore, the smaller size of the micelles significantly reduces the surface area of interaction between the micelle and the cell surface, as these micelles have only ~15-20 nm diameter (~3000 $nm^2$ total surface area), compared to a 100 nm liposome (~125000 $nm^2$ total surface area). Thus, a longer linker is necessary to sufficiently expose the peptide to initiate the multivalent binding interactions required for cellular uptake.

In order to determine if 3 lysine residues provided optimal cellular uptake for this system as well, we assessed the optimal oligolysine chain length on the cellular uptake of micelles by synthesizing VLA4pep($K_N$) with an EG18 peptide-linker and varying N from 0-4 (FIG. 15C). Targeted micelles were formulated as 80:10 PEG2000:VLA4pep ($K_N$). Our results showed minimal uptake with the incorporation of 0-2 lysine residues, but a significant enhancement was observed with the inclusion of 3 lysines. This is in agreement with our results demonstrated previously with the liposomes, indicating that the oligolysine content of 3 units sufficiently increased the peptide hydrophilicity in order to more effectively present the peptide above the PEG2000 coating for binding and uptake of nanoparticles.

To examine the relationship between peptide valency and cellular uptake, we prepared targeted micelles containing VLA4pep($K_3$) with EG18 linker, where the valency was varied from 0 to 30 peptides per micelle (FIG. 15D). The uptake efficacy reached a maximum and approached a plateau at higher densities with ~27 fold enhancement for both cell lines at 30 peptides per micelle. To verify the specificity of the observed interaction, competition experiments in the presence of free VLA4pep were performed (FIGS. 15E and 15F), which showed significant inhibition, demonstrating specificity and receptor involvement in uptake.

Figure 16:
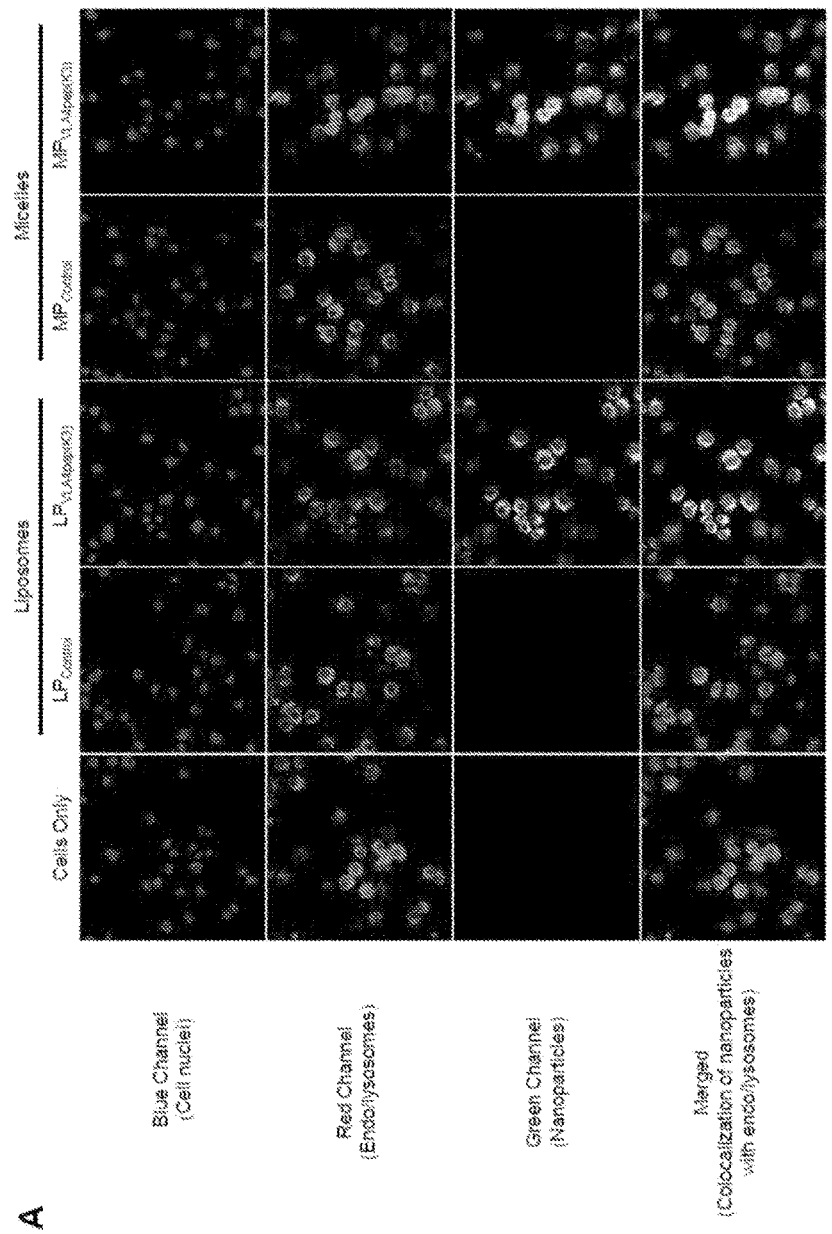
FIG. 16. Determination of cellular uptake via confocal microscopy. Fluorescein labeled nanoparticles were incubated with NCI-H929 (A) or MM.1S (B) cells for 3 hours at 37° C. The cells were counterstained with Lysotracker Red and Hoechst dyes. Merged images reveal co-localization. Internalization of nanoparticles was determined with a Nikon A1R confocal microscope using a 40× oil lens. Image acquisition was performed by Nikon Elements Ar software.
Figure 16:
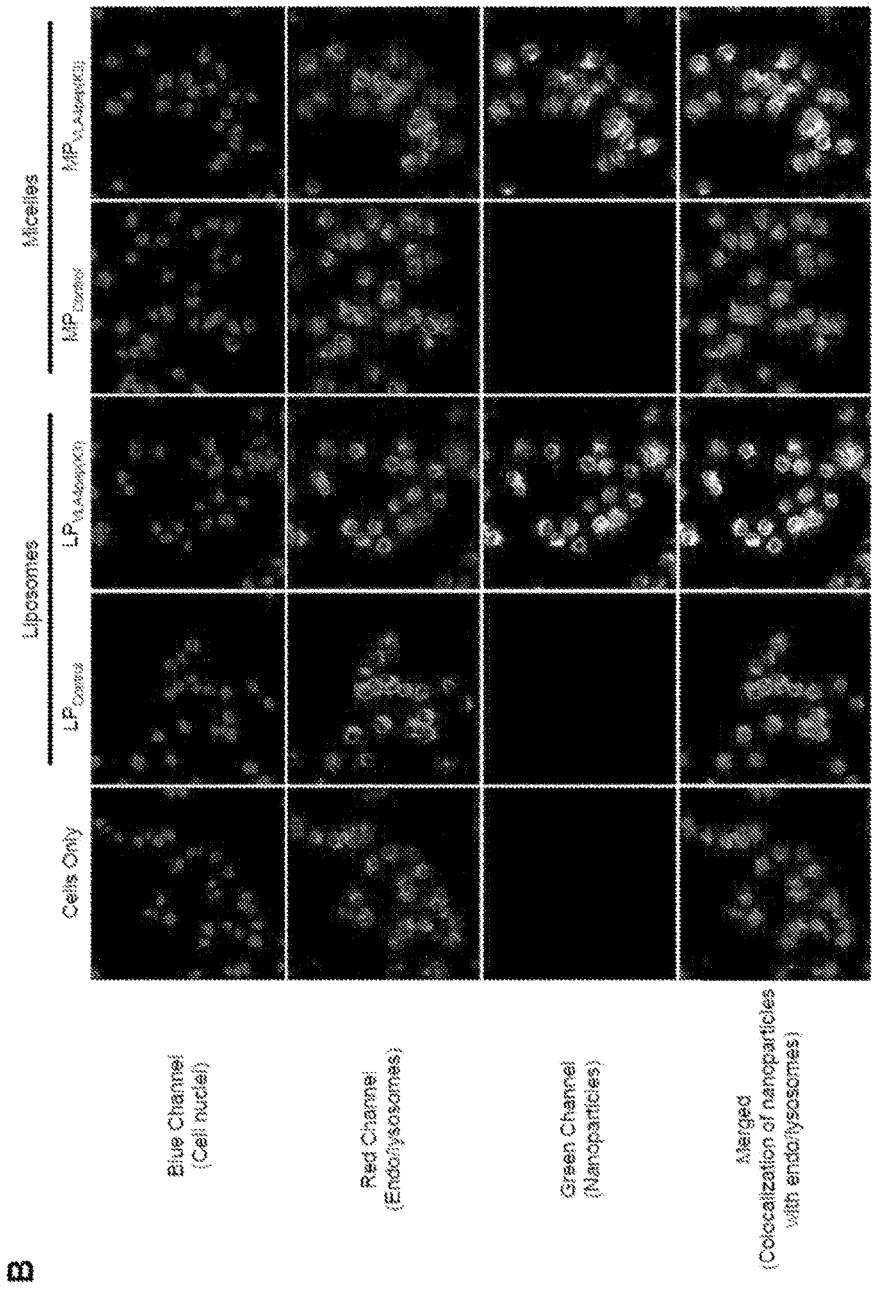

Validation of Cellular Uptake Results with Confocal Microscopy. While flow cytometry is a powerful tool to quantify association of nanoparticles with cells, it does not distinguish between cellular binding and cellular internalization. To confirm cellular uptake and internalization of the nanoparticles by the multiple myeloma cells, we performed confocal microscopy experiments with fluorescein labeled liposomes (93:10:5:2 HSPC:CHOL:PEG2000:VLA4pep ($K_3$)) and micelles (80:10 PEG2000:VLA4pep($K_3$)). Non-targeted nanoparticles and cell only controls were also included. Intracellular acidic vesicles (endosomes/lysosomes) were labeled with LysoTracker Red and the co-localization of the nanoparticles in intracellular vesicles was examined. In both NCI-H929 and MM.1S cell lines, we observed significant internalization into lysosomes with targeted formulations, with no internalization evident with non-targeted nanoparticles (FIGS. 16A and 16B).

Figure 17:
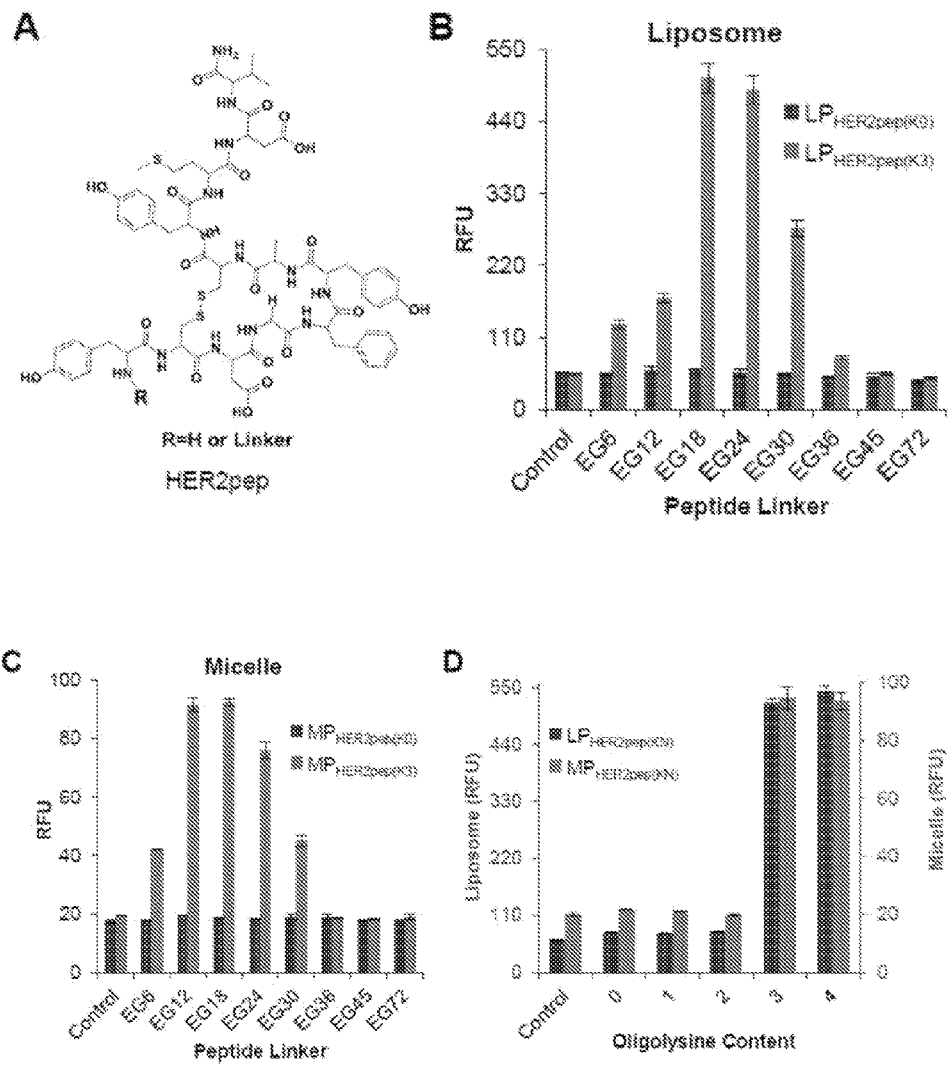
FIG. 17. Effect of EG peptide-linker length and oligolysine ($K_N$) content on the cellular uptake of HER2-targeted liposomes and micelles. (A) Structure of HER2-antagonist peptide (HER2pep) is shown. (B) The effect of EG peptide-linker length on the uptake of liposomes targeted with HER2pep($K_0$) ($LP_{HER2pep(K0)}$; left columns) and HER2pep ($K_3$) ($LP_{HER2pep(K3)}$; right columns) by SK-BR-3 cells. (C) The effect of EG peptide-linker length on the uptake of micelles targeted with HER2pep($K_0$) ($MP_{HER2pep(K0)}$; left columns) and HER2pep($K_3$) ($MP_{HER2pep(K3)}$; right columns) by SK-BR-3 cells. The EG peptide-linker lengths investigated include: EG6, EG12, EG18, EG24, EG30, EG36, EG45, and EG72. (D) The effect of oligolysine chain length on cellular uptake by SK-BR-3 cells was evaluated with liposomes (left columns) and micelles (right columns) targeted with HER2pep($K_N$)-pep using an EG18 peptide. The $K_N$ content varied from N=0-4. (E) Cellular uptake via confocal microscopy was determined by incubating SK-BR-3 cells with fluorescein labeled nanoparticles and then counterstaining with Lysotracker Red and Hoechst dyes. Merged images reveal co-localization and internalization of nanoparticles.
Figure 17:
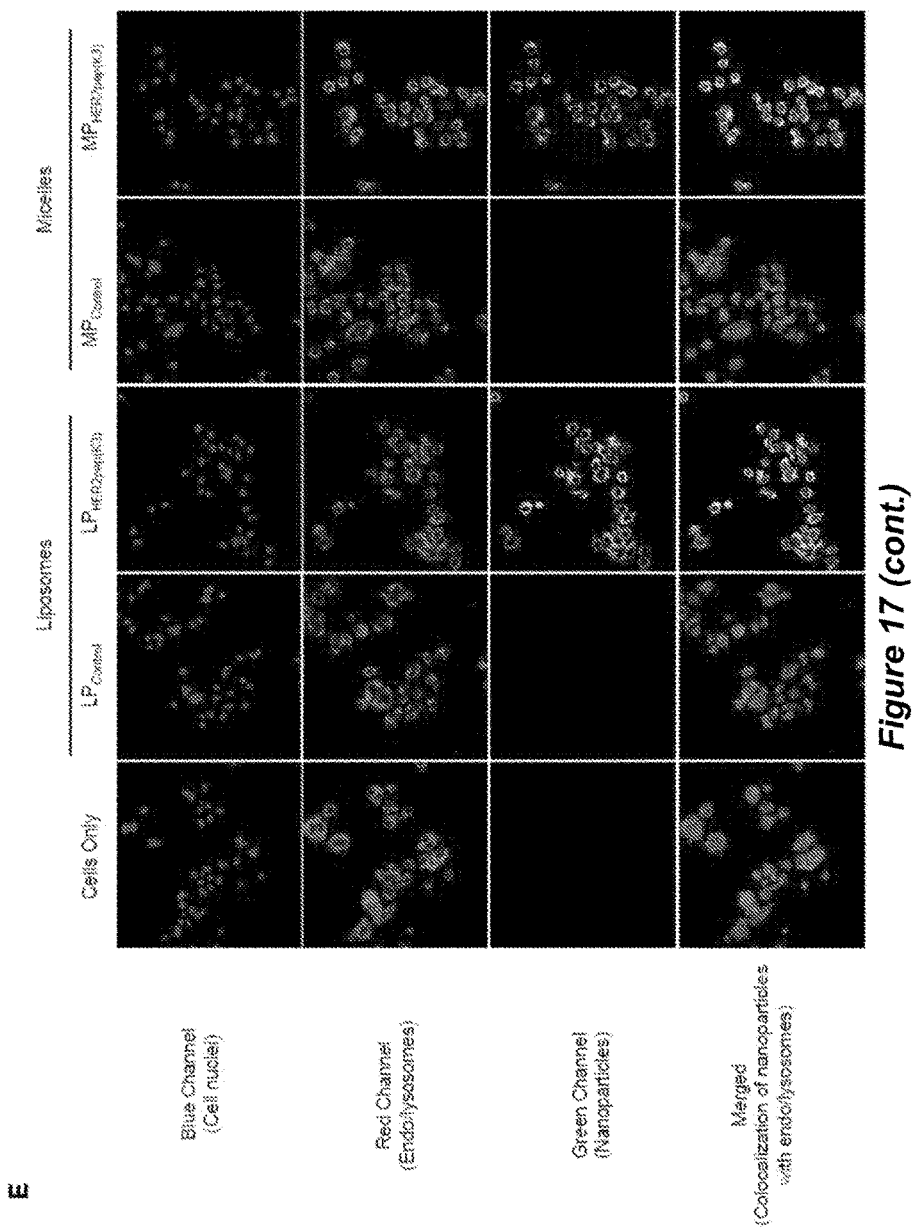

Effect of EG Peptide-Linker Length and Oligolysine Content ($K_N$) on the Cellular Uptake of HER2-Targeted Liposomes and Micelles. To confirm that the conclusions derived from the experiments presented with VLA-4-targeting liposomes and micelles can be applied broadly to other peptide-targeted delivery systems, we have undertaken a similar analysis with HER2-overexpressing breast cancer cells. HER2 is overexpressed in ~25% of breast cancer cases and several cell lines have been identified to overexpress HER2 including SK-BR-3 and BT-474 cells. First, we validated HER2 receptor expression in SK-BR-3 cells (see FIG. 15A). Several antagonistic peptides of HER2 have been identified. The cyclic peptide sequence, YCDGFYA-CYMDV (SEQ ID NO: 1) (HER2pep; FIG. 17A), has been reported to bind to an extracellular HER2 domain with submicromolar affinity ($K_d$=150 nM). We determined selective binding of this peptide to SK-BR-3 cells by flow cytometry using a fluorescein labeled version of the peptide (see FIG. 15C).

We then prepared HER2-targeted liposomal and micellar nanoparticles with variable oligolysine content ($K_N$; N=0 or 3) and EG peptide-linker length (EG6 to EG72) to analyze cellular uptake in SK-BR-3 cells by flow cytometry. Our results obtained with the HER2-targeting system demonstrated consistent results with the VLA-4 system. When HER2pep with no lysines (HER2pep($K_0$)) was incorporated into the targeted liposomes (93:10:5:2 HSPC:CHOL:PEG2000:HER2pep($K_0$)), we observed no enhancement in cellular uptake regardless of EG peptide-linker length (FIG. 17B). However, incorporation of HER2pep with a short oligolysine chain (HER2pep($K_3$)) in the targeted formulation (93:10:5:2 HSPC:CHOL:PEG2000:HER2pep($K_3$)) resulted in a significant enhancement in cellular uptake, reaching a maximum with an EG18 peptide-linker. Similarly, micelles targeted with HER2pep($K_0$) (75:15 PEG2000:HER2pep($K_0$)) displayed minimal uptake across the various EG linker lengths examined, while micelles targeted with HER2pep($K_3$) (75:15 PEG2000:HER2pep ($K_3$)) were efficiently taken up by the cells, with maximum uptake observed using an EG18 peptide-linker as well (FIG. 17C).

These results demonstrated that the cellular uptake of both HER2-targeted liposomes and micelles can be significantly enhanced by increasing the peptide hydrophilicity and optimizing the EG peptide-linker length. One minor difference between the VLA-4- and HER2-targeted liposomes was that while an EG6 peptide-linker was optimal for the VLA-4 system, an EG18 linker was optimal for the HER2 system. This is likely due to the distinct chemical properties for each targeting peptide. HER2pep is a 12 residue peptide compared to the 5 residue VLA4pep and is more hydrophobic with several aromatic residues. Therefore, a longer linker may be required to further increase its aqueous solubility when compared to the VLA4pep. In addition, the particular receptor-ligand interactions and location of the binding pocket could also play a role. The EG18 linker is possibly the optimum distance necessary to allow HER2pep to adopt a proper conformation to bind to the binding pocket on the target receptor and permit multivalent interactions.

To determine the optimal oligolysine chain length necessary for most efficient cellular uptake, we synthesized HER2pep($K_N$) with an EG18 peptide-linker, varied N from 0-4, and evaluated cellular uptake for both micelles and liposomes (FIG. 17D). Our results showed minimal cellular uptake with 0-2 lysines, but a significant enhancement was observed with the inclusion of 3 lysines. Confirmation of nanoparticle uptake was also demonstrated through co-localization studies performed with the lysosomal marker Lysotracker Red and fluorescein labeled nanoparticles using confocal microscopy. Both liposomes and micelles targeted with HER2pep($K_3$) and EG18 linker showed significant internalization into lysosomes (FIG. 17E). Collectively, these results were consistent with the VLA-4 targeting system, validating that the conclusions drawn can be applied broadly to other peptide targeted systems, although exact properties, such as the optimal EG linker length, may differ slightly.

Effect of EG Peptide-Linker Length and Oligolysine Content ($K_N$) on the Cellular Uptake of Nanoparticles Under Fluidic Conditions. To further validate our experimental findings under physiologically relevant conditions, we examined the uptake efficiency of our peptide-targeted nanoparticle formulations under fluidic conditions to mimic those found in physiological systems. Because our study included two cancer cell types with distinct in vitro culture conditions (multiple myeloma cells grow in suspension, while breast cancer cells are adherent), we employed two model flow channel systems for use in our experiments. For the multiple myeloma system, a peristaltic pump connected to a reservoir was used to load the myeloma cells (NCI-H929 or MM.1S) and nanoparticles into the circulating system. After loading, the reservoir inlet and outlets were connected to create a closed circulating system. This design minimized any cellular uptake of nanoparticles that may have occurred in the reservoir under more static conditions. For the breast cancer system, the model flow system was adopted from previous studies (Zebli et al., *Langmuir* 2005, 21, 4262-4265; del Pino et al., *Nano Lett.* 2010, 10, 3914-3921).

Breast cancer cells (SK-BR-3) were cultured overnight on a tissue culture treated flow channel to promote cell adhesion. Then, a reservoir containing the nanoparticles was connected to the flow channel through a peristaltic pump. For both model systems, the velocity of the flow was regulated by the pump and varied between 5 and 16 cm/s in our experiments to be comparable to the blood flow rates in the circulatory system. The flow channel, reservoirs, and connective tubing were placed inside an incubator to maintain a constant temperature of 37° C. Fluidic experiments were performed for 1 hour, and cellular uptake was analyzed by flow cytometry.

Figure 18:
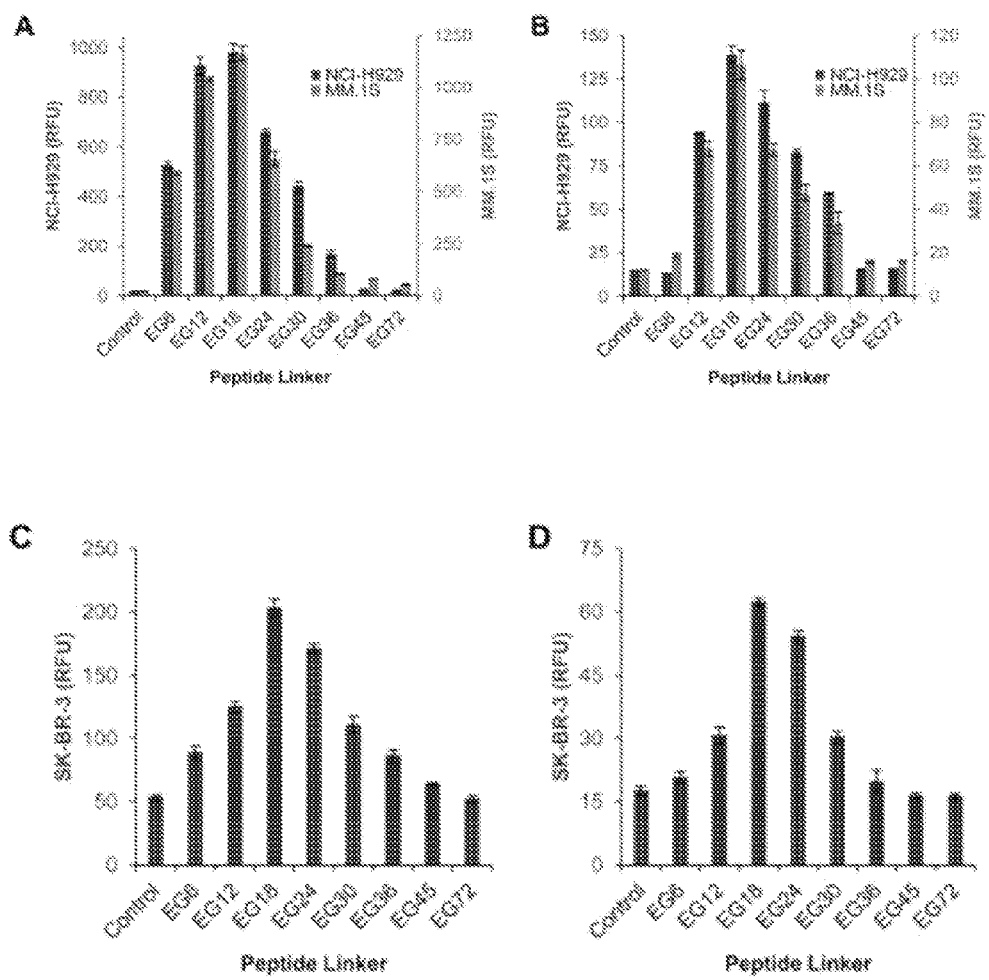
FIG. 18. Effect of EG peptide-linker length and oligolysine ($K_N$) content on the cellular uptake of VLA-4- and HER2-targeted liposomes and micelles under fluidic conditions. The effect of EG peptide-linker length on the cellular uptake of VLA-4-targeted liposomes (A) or micelles (B) using VLA4pep($K_3$) was evaluated using NCI-H929 (left columns) and MM.1S cells (right columns) by flow cytometry. The effect of EG peptide-linker length on the cellular uptake of HER2-targeted liposomes (C) or micelles (D) using HER2pep($K_3$) was evaluated using SK-BR-3 cells by flow cytometry. The effect of oligolysine chain length ($K_N$) was evaluated using liposomes (E) or micelles (F) targeted with VLA4pep($K_N$) with EG18 peptide-linker (NCI-H929 (left columns) and MM.1S cells (right columns)). The effect of oligolysine chain length ($K_N$) was evaluated using liposomes (G) or micelles (H) targeted with HER2pep($K_N$) with EG18 peptide-linker.
Figure 18:
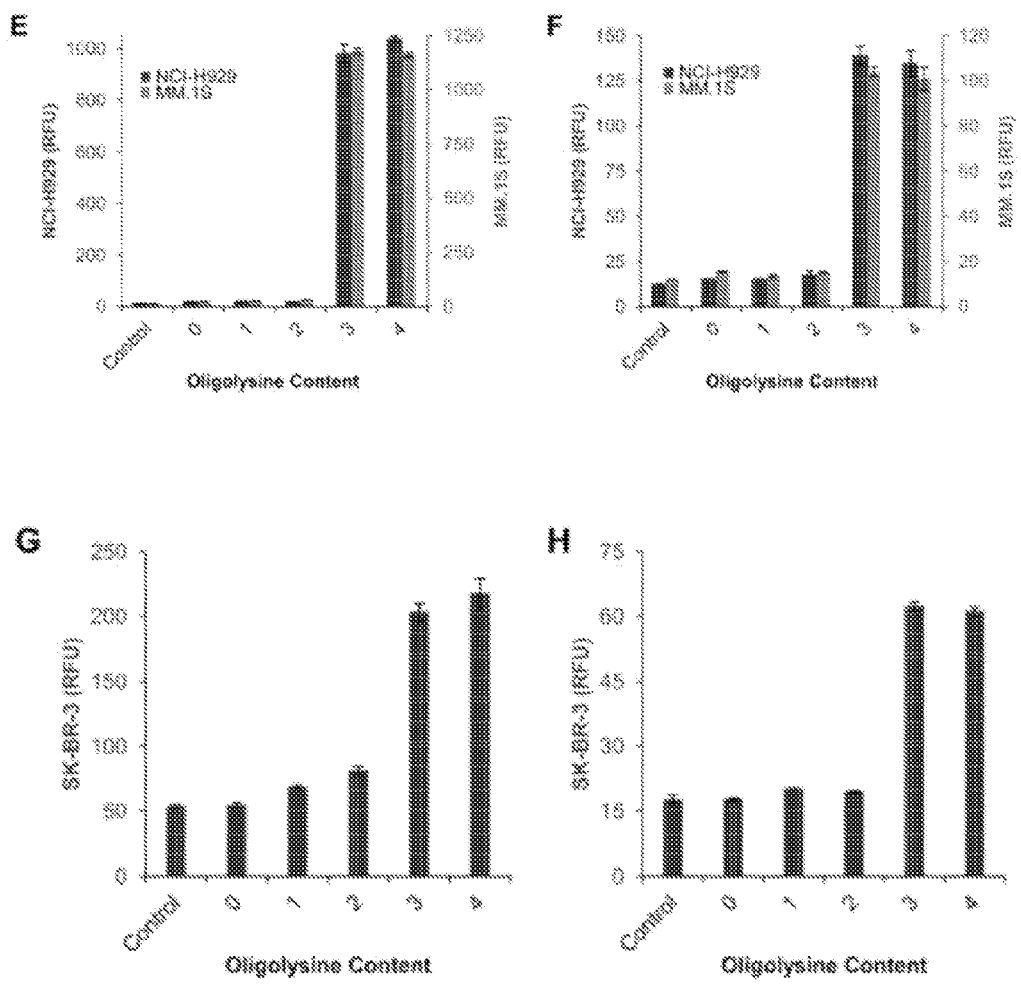

In the fluidic experiments, we examined the effect of EG peptide-linker length and peptide hydrophilicity on the cellular uptake of both VLA-4 and HER2-targeted liposomes and micelles. First, we formulated VLA-4-targeted liposomes and micelles that incorporated VLA4pep($K_3$) with variable EG peptide-linker lengths of EG6, EG12, EG18, EG24, EG30, EG36, EG45, and EG72 (FIGS. 18A and 18B). Targeted liposomes and micelles were formulated as 93:10:5:2 HSPC:CHOL:PEG2000:VLA4pep($K_3$) and 80:10 PEG2000:VLA4pep($K_3$), respectively. Although the results for the cellular uptake of micelles under fluidic conditions were similar to those under static conditions with maximum cellular uptake occurring with the use of the EG18 peptide-linker, we observed a distinct shift for optimal peptide-linker length for the liposome system. Under fluidic conditions, an EG18 peptide-linker provided maximum cellular uptake of liposomes, while an EG6 peptide-linker was optimal under static conditions. This can possibly be attributed to the deformation of the liposomes that occurs under fluidic conditions, which may necessitate the use of a longer linker to more effectively present the peptide for binding to its target receptor. Additionally, although an EG18 peptide-linker may be less energetically favorable compared to EG6, the extra ~5 nm extension may be imperative for initiating receptor-ligand interactions under fluidic conditions. Importantly, traditional formulations including an EG45 or longer linker in the targeting sequence still resulted in negligible cellular uptake.

Next, we evaluated the effect of EG peptide linker length using HER2-targeted liposomes (93:10:5:2 HSPC:CHOL: PEG2000:HER2pep($K_3$)) and micelles (75:15 PEG2000: HER2pep($K_3$)) on cellular uptake in fluidic conditions (FIGS. 18C and 18D). In the breast cancer system, we observed very similar trends to the experiments performed in static conditions, with an EG18 peptide linker providing maximum cellular uptake of both liposomes and micelles. Next, we determined the optimal oligolysine chain length under fluidic conditions by formulating VLA-4-targeted liposomes (93:10:5:2 HSPC:CHOL:PEG2000:VLA4pep ($K_N$)), VLA-4-targeted micelles (80:10 PEG2000:VLA4pep ($K_N$)), HER2-targeted liposomes (93:10:5:2 HSPC:CHOL: PEG2000:HER2pep($K_N$)), and HER2-targeted micelles (75: 15 PEG2000:HER2pep-($K_N$)) and evaluating cellular uptake (FIGS. 18E-H). In both cancer models and both nanoparticle types, our results showed minimal cellular uptake with zero to two lysines, but a significant enhancement was observed with the inclusion of three lysines, in agreement with the experiments performed under static conditions. Altogether, these results demonstrated the significance of peptide hydrophilicity and EG peptide-linker length in the efficient cellular uptake of our nanoparticle formulations under physiologically relevant conditions, with an EG18 peptide-linker and three lysine residues providing maximum cellular uptake across all systems analyzed.

Conclusion. Nanotechnology has been recognized as a paradigm-changing opportunity by National Cancer Institute with the potential to make significant breakthroughs in cancer diagnosis and therapy. Ligand-targeted nanoparticles, however, have not consistently delivered successful outcomes. In this study, we evaluated how the chemical properties of peptide ligands, specifically their hydrophilicity, the EG peptide-linker length, and peptide valency affect cellular uptake of peptide-targeted liposomal and micellar nanoparticles. Our results demonstrated, in both the myeloma and breast cancer models, that the cellular uptake of liposomes and micelles can be significantly enhanced by increasing the hydrophilicity of the targeting peptide ligand via incorporation of a short oligolysine chain ($K_3$) adjacent to the targeting peptide. It is noteworthy that, previously, the use of oligoarginine (R8, 8 repeat units of arginine) as a cell penetrating peptide in liposomes has demonstrated efficiency in promoting cellular uptake through nonreceptor-dependent-pathways. However, in our design, we selected lysine as the residue of choice due to its much weaker cell penetrating effects in order to minimize cellular uptake due to non-specific interactions. Importantly, successful inhibition of cellular uptake during competition experiments using excess soluble peptide demonstrated that the targeted nanoparticles were highly specific, and confirmed receptor involvement for the observed cellular uptake.

Our results also demonstrated a strong dependence of cellular uptake on the EG peptide-linker length. In accordance with traditional "stealth" liposome formulations, our design maintained the PEG2000 coating, which has been shown to provide improved stealth and bioavailability to nanoparticles in vivo. However, in contrast to the previous groups who have used PEG2000 (~EG45) or longer polymers as ligand linkers, we increased targeting effectiveness by decreasing the length of the EG peptide-linker. Due to the complex structures long PEG polymers adopt on the surface of liposomes and micelles (see Barenholz, Curr. Opin. Colloid Interface Sci. 2001, 6, 66-77 and Vukovic et al., J. Am. Chem. Soc. 2011, 133, 13481-13488, respectively), using long linkers such as PEG2000 to present the ligand does not effectively promote binding, as the PEG will sterically hinder the association of the ligand-targeted nanoparticles with their target receptor. Shorter linkers, on the other hand are more likely to adopt a linear conformation compared to their longer counterparts and will restrict the translational freedom of the peptide, reducing the overall entropic losses upon binding, thereby providing significant thermodynamic advantages in binding to the respective cell surface receptors.

Our results validated this hypothesis by demonstrating that EG6 and EG18 linkers provided most effective cellular uptake of VLA-4-targeted liposomes and micelles, respectively. Notably, similar results were also obtained with the HER2-targeted nanoparticles, confirming that our approach is not peptide, receptor, or disease specific. Taken together, these results establish the significance of ligand chemical properties, EG peptide-linker length, and location of ligand-receptor interactions in the cellular uptake of nanoparticles.

In summary, the results presented in this our study demonstrate a universal approach to systematically improve the cellular uptake of peptide-targeted nanoparticles by increasing the hydrophilicity of peptide ligands with oligolysine chains and by using the appropriate EG peptide-linker length. Despite the identification of a wide variety of potential peptides and peptidomimetics as targeting ligands through the use of in silico screenings and phage display libraries, not all identified ligands may readily have suitable characteristics to be used in an active-targeting platform. For example, chemical properties of the ligand, specifically hydrophobicity, may limit ligand accessibility for binding. Here, we have shown increased cellular uptake of nanoparticles functionalized with both hydrophilic (VLA4pep) and hydrophobic (HER2pep) targeting peptides, both of which have only moderate affinities for their target receptors, demonstrating the widespread application of our method for enhancing active targeting approaches. Importantly, our results established a strategy to achieve favorable results in cellular targeting and uptake, which was otherwise unattainable with traditional targeting strategies. Taken together, this study demonstrates the importance of using effective design elements, such as the appropriate EG peptide-linker length, optimal ligand density, and solubility enhancements to drive efficient cellular uptake of nanoparticles.

Methods.

Materials. Materials were obtained according to the Materials section of Example 1. Additionally, 1,2-distearoyl-sn-glycero-3-phosphocholine (DSPC), 1,2-dipalmitoyl-sn-glycero-3-phosphocholine (DPPC), and methoxy PEG2000-DSPE (PEG2000-DPSE) were obtained from Avanti Polar Lipids, Inc (Alabaster, Ala.).

Synthesis of Peptides and Peptide($K_N$)-$EG_{linker}$-Lipid Conjugates. See the corresponding Synthesis of Peptides section of Example 1.

Characterization of Liposomes. See the corresponding section of Example 1.

Cell Culture. SK-BR-3, NCI-H929, and MM.1S cell lines were obtained from American Type Culture Collection (Rockville, Md.). SK-BR-3 cells were cultured in McCoy's 5A (ATCC) media, while NCI-H929 and MM.1S cell lines were cultured in RPMI 1640 media (Cellgro, Manassas, Va.). All lines were supplemented with 10% fetal bovine serum (FBS), 2 mM L-glutamine (Gibco, Carlsbad, Calif.), 100 U/mL penicillin, and 100 µg/mL streptomycin (Gibco). NCI-H929 cells were supplemented with an additional 10% FBS and 55 µM 2-mercaptoethanol. MM.1S cells were supplemented with an additional 10% FBS.

Receptor Expression Analysis and Cell-Based Peptide Binding Assays. For VLA-4 expression assays, cells were incubated with anti-CD49d (phycoerythrin) or anti-CD29 (fluorescein) antibodies (BD Biosciences, San Jose, Calif.) in binding buffer (1.5% BSA in PBS pH 7.4) on ice for 1 hour and were washed twice. For HER2 expression assays, cells were incubated with primary antibody in binding buffer on ice for 1 hour and washed twice. Fluorescein conjugated secondary antibody was added for 1 hour on ice, samples were washed, and analyzed on Guava easyCyte 8HT flow cytometer (Millipore). Isotype matched antibodies were used as negative controls. For cell-based peptide binding assays, cells were incubated with increasing concentrations of fluorescein-conjugated peptides for 2 hours on ice. Samples were washed twice and analyzed on Guava easy-Cyte 8HT flow cytometer.

Nanoparticle Preparation. Liposomes were prepared by dry film hydration. Briefly, a lipid mixture of chloroform stocks was prepared and dried to form a thin film using nitrogen gas then placed under vacuum overnight to remove residual solvent. The lipid films were hydrated at 65° C. in PBS pH 7.4, gently agitated, and extruded at 65° C. through a 0.1 µm polycarbonate filter. Liposomes all adhered to the following formula (95-x):10:5:x HSPC:CHOL:PEG2000-DSPE:peptide($K_N$)-$EG_{linker}$-lipid conjugate where x was varied between 0-4 to control the peptide density. Control liposomes were always formulated as 95:10:5 HSPC:CHOL:PEG2000. For micelle formation, nonfunctionalized and functionalized lipids were mixed at desired molar ratios in $CHCl_3$, followed by solvent removal via evaporation. The mixture was then re-suspended in PBS and sonicated until clear. Micelles adhered to the formula (90-x):x PEG2000-DSPE:peptide($K_N$)-$EG_{linker}$-lipid conjugate where x was varied between 0-30 to control the peptide density. Control micelles were always formulated with 100% PEG2000-DSPE. Fluorescein PE and lissamine rhodamine B PE we added as fluorescent agents for uptake quantification.

In Vitro Nanoparticle Uptake Assays. $1 \times 10^5$ cells/well were plated 24 hours prior to each experiment in a 24 well dish. Nanoparticles were added at 100 µM phospholipid concentration and incubated for 3 hours at 37° C. Fluorescein PE was added as a fluorescent marker to each liposomal formulation while lissamine rhodamine B PE was added to micelle formulations. For suspension cells, after incubation, cells were washed 3 times with PBS and analyzed via flow cytometry. For adherent cells, after incubation, cells were washed 3 times with PBS, trypsinized, and analyzed via flow cytometry.

Confocal Microscopy. $1 \times 10^5$ cells/well were plated 24 hours prior to each experiment in a 24 well dish (suspension cells) or onto 12 mm borosilicate glass coverslips (adherent cells). Nanoparticles were labeled with fluorescein PE, added at 100 µM phospholipid concentration, and incubated for 3 hours at 37° C. After incubation, the cells were washed 3 times with PBS and incubated with 50 nM Lysotracker Red (Molecular Probes, Carlsbad, Calif.) for 30 minutes at 37° C. to allow internalization. Cells were washed 3 times, fixed in PFA, stained with 2 µg/mL Hoescht dye (Sigma) for 15 minutes, washed 3 times, and mounted on glass slides using Prolong Gold Antifade Reagent (Molecular Probes). Cells were visualized by Nikon A1R confocal microscope with a 40x oil lens (Nikon Instruments, Melville, N.Y.). Image acquisition was performed by Nikon Elements Ar software (Nikon).

Example 3

Liposomal Drug Delivery of Proteasome Inhibitors for the Treatment of Cancers

Bortezomib and carfilzomib are FDA approved first and second generation proteasome inhibitors for the treatment of multiple myeloma. However, the effectiveness of therapy involving bortezomib and carfilzomib is reduced by dose limitations due to their non-specific toxicities. This example describes the incorporation of bortezomib and carfilzomib into long circulating liposomes for improved drug delivery and enhanced tumor accumulation. The methods described herein can be extended to other anticancer agents including hydrophobic actives. The drug-loaded nanoparticles are internalized by and cytotoxic to cancer cells, including multiple myeloma cell lines. Xenograph models showed that administration of the nanoparticles reduces systemic toxicity and improves tumor growth inhibition compared to the corresponding free drug. This example thus describes the successful incorporation and administration of bortezomib and carfilzomib loaded nanoparticles. These methods can be extended to other therapeutic agents such as hydrophobic anticancer drugs.

Methods.

Materials. Membranes (30, 50, and 100 nm), mini-extruder and lipid components were purchased from Avanti Polar Lipids, Inc. (Alabaster, Ala.). Carfilzomib was obtained from ChemieTek (Indianapolis, Ind.). Bortezomib was obtained from GenDepot (Barker, Tex.). Fmoc-$(EG)_6$-OH modification reagents were from Quanta Biodesign (Powell, Ohio). N-Fmoc-amino acids, NovaPEG Rink amide resin, Wang resin, and 2-(1H-benzotriazole-1-yl)-1,1,3,3-tetramethyluronium hexafluorophosphate (HBTU) were obtained from EMD Millipore (Billerica, Mass.). All other chemicals were obtained from Sigma-Aldrich (St. Louis, Mo.).

Liposome Preparation.

A. Carfilzomib Loaded Liposomes. Liposomes were prepared by dry film hydration. Briefly, a lipid mixture of chloroform stock was prepared and dried to form a thin film using nitrogen gas, then was placed under vacuum overnight to remove residual solvent. The lipid films were hydrated at 65° C. in PBS pH 7.4, gently agitated, and extruded at 65° C. through a 0.1 µm polycarbonate filter. Liposomes all adhered to the following formula: (95-x-n):x:5:n DSPC:Carf.:PEG-DSPE:VLA4-pep-EG6-lipid conjugate where n was either 0, or 0.5 if a targeting peptide was desired; and x varied between 0 and 10 depending on the desired drug loading.

B. Bortezomib Loaded Liposomes. Liposomes were prepared by dry film hydration. Briefly, a lipid mixture of chloroform stock was prepared and dried to form a thin film using nitrogen gas, then was placed under vacuum overnight to remove residual solvent. The lipid films were hydrated at 65° C. in PBS pH 7.4, gently agitated, and extruded at 65° C. through a 0.1 µm polycarbonate filter. Liposomes all adhered to the following formula: (92.5-n):2.5:5:n DSPC:Bort Conjugate:PEG-DSPE:VLA4-pep-EG6-lipid conjugate, where n was either 0, or 0.5 if a targeting peptide was desired.

Cell Culture. MM.1S and NCI-H929 cell lines were obtained from American Type Culture Collection (Rockville, Md.). All lines were supplemented with 20% fetal bovine serum (FBS), 2 mM I-glutamine (Gibco, Carlsbad, Calif.), 100 μg/mL penicillin, and 100 μg/mL streptomycin (Gibco). NCI-H929 cells were further supplemented with 55 μM 2-mercaptoethanol.

Particle Sizing. Particle size was observed using DLS analysis via the 90Plus Nanoparticle Size Analyzer (Brookhaven Instruments Corp.), using 658 nm light observed at a fixed angle of 90° at 20° C.

Cytotoxicity Assays. A Cell Counting Kit-8 (Dojindo Molecular Technologies, Rockville, Md.) was used for cytotoxicity assays.

Figure 19:
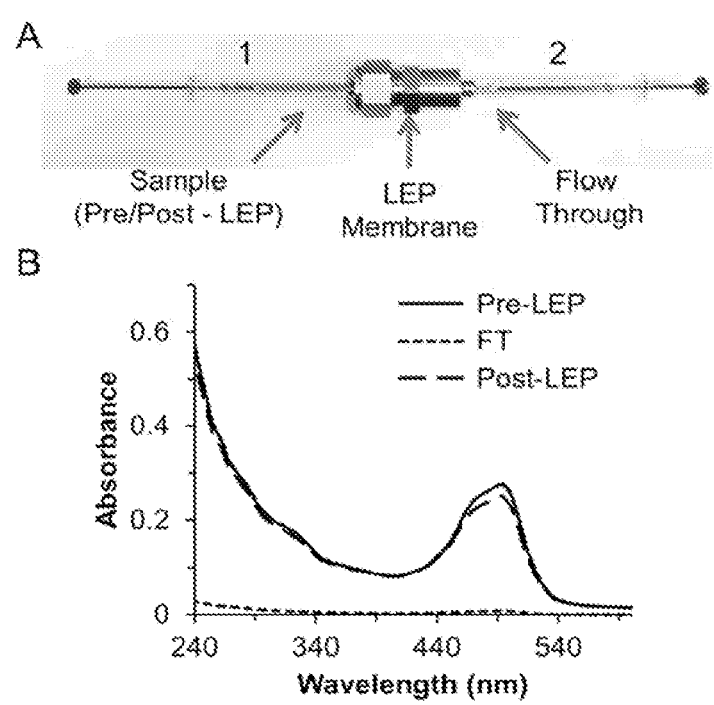
FIG. 19. A) Picture of the liposome extrusion and LEP apparatus with significant components identified. B) Pegylated liposomes were formed incorporating 1% FITC lipid to aid in liposome visualization. LEP was performed on a 250 μL liposome sample and absorbance scans were preformed Pre- and Post-LEP after the concentrate was diluted back to its original 250 μL volume. No liposomes were observed in the flow through fraction and a >94% liposome recovery was achieved.

Liposome Extruder Purification. A simple technique that can be universally applied across many liposome formulations, for the efficient and economical purification of liposomes, can be carried out as follows. The Liposome Extruder Purification (LEP) technique requires only the same components that were necessary to initially extrude/form the liposome samples: an extruding device, syringes and specifically sized extrusion membranes (FIG. 19A). Essentially, the formed and functionalized liposome solutions can be passed through a membrane of a lesser pore diameter at a temperature below the lipid glass transition temperature. The liposomes are retained on the starting side of the membrane while unreacted components flow freely through the membrane. This technique is very simple to implement, reduces purification costs, and provides for the ability to rapidly test and purify diverse liposome formulations preventing contamination from previously purified liposomes. The result is a lab scale batch process for efficiently purifying liposomes using, for example, a 50 nm membrane with a greater than 94% liposome recovery and the capacity to efficiently separate liposomes from proteins as large as antibodies (~10 nm globular protein size). See FIG. 19B. Using LEP, liposome solutions can also be concentrated many fold and buffers can be exchanged without reducing their concentration.

Figure 20:
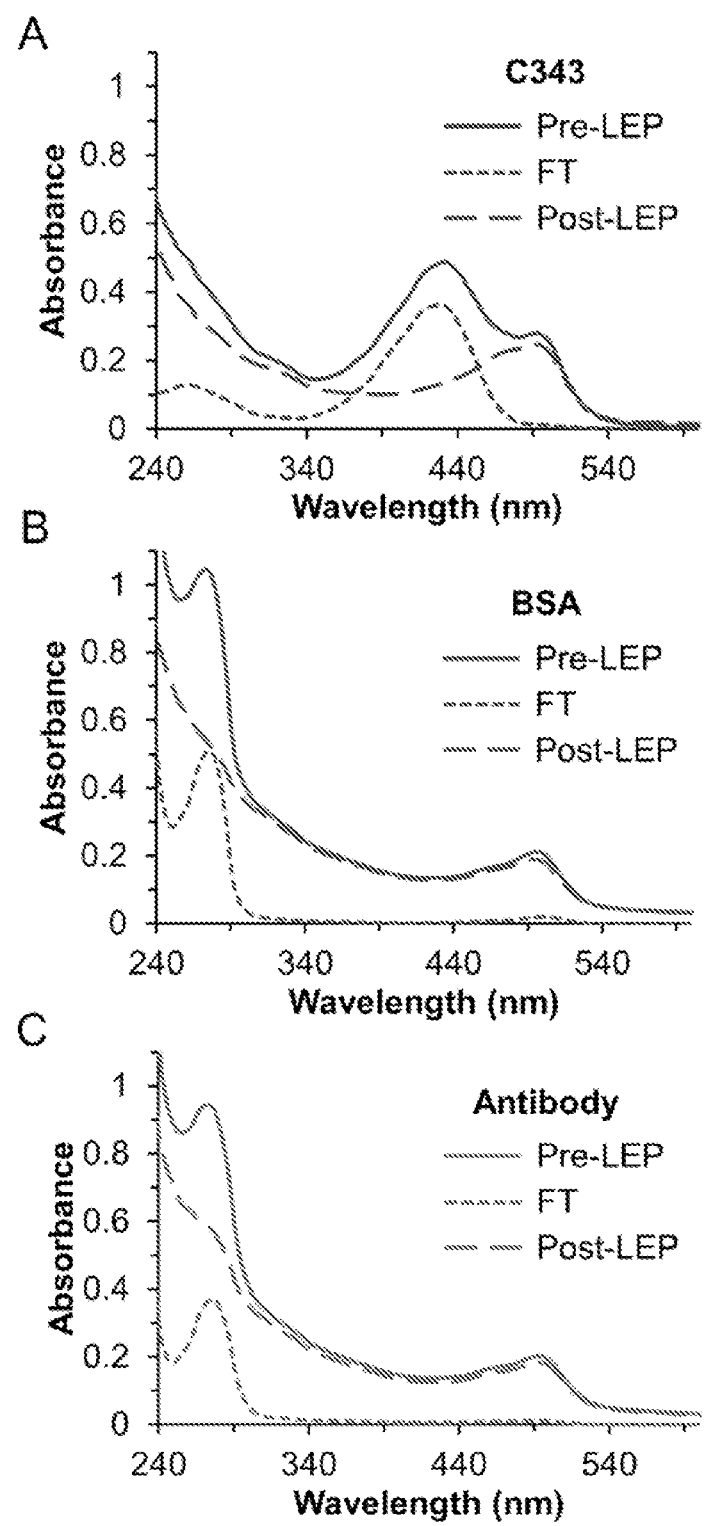
FIG. 20. One cycle of LEP absorbance scans of Pre-LEP sample (solid line), flow through (FT, short dashed line) and Post-LEP sample (long dashed line) for mixed 100 nm liposome and contaminant samples. A) Coumarin 343 (32 μM), B) BSA (3 mg/mL), C) Trastuzumab (1 mg/mL).

The LEP technique removes contaminants while retaining the liposomes. As a set of example purifications, 100 nm pegylated liposomes at 1 mM lipid concentration were contaminated with 32 μM Coumarin 343, 3 mg/mL BSA and 1 mg/mL trastuzumab. LEP was carried out on the liposomes using a 50 nm membrane to a final volume of 5 μL, followed by rehydration to their original 250 μL starting volumes. Absorbance scans of the Pre-LEP, flow through (FT) and Post-LEP samples were used to assess liposome recovery and contaminant clearance (FIG. 20). In all cases a >93% liposome recovery with a >92% contaminant clearance was observed. This translates to a >14 fold contaminate reduction after a single LEP cycle, where the theoretical maximum fold reduction in contaminant is 16.7 fold.

Figure 21:
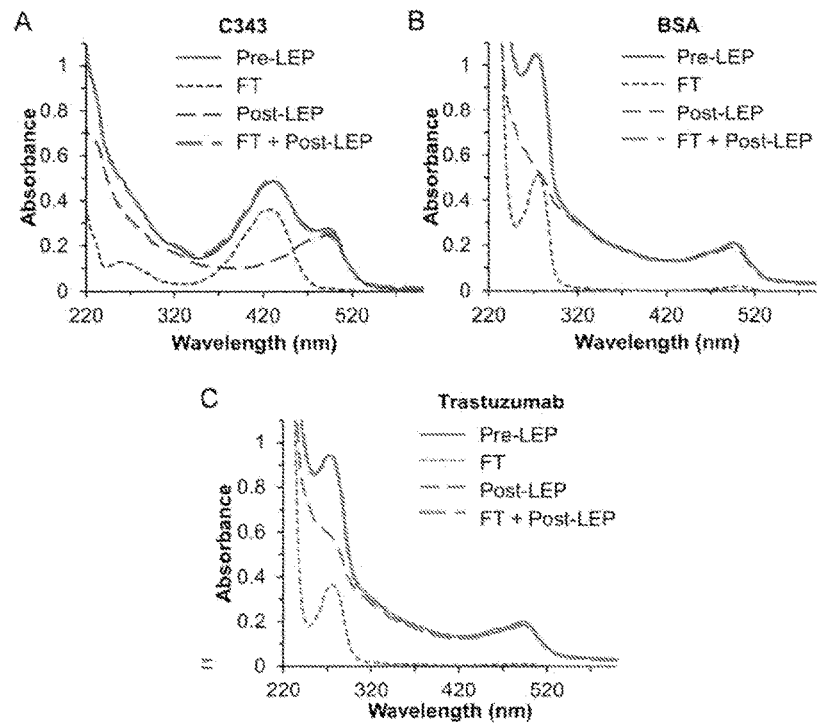
FIG. 21. Absorbance scans for the purification of liposomes from $C_{343}$ (A), BSA (B) and Trastuzumab (C). To demonstrate that there is a minimal loss of liposomes or contaminate to the LEP system, the Post-LEP purified liposome absorbance curve and the flow through (FT) curve were summed. In all cases this new curve nearly perfectly overlays onto the Pre-LEP sample absorbance curve. If there were loses of any kind associated with the process we would expect the sum of the Post-LEP and FT curves to be less than the initial absorbance scan of the Pre-LEP sample.

As was expected, the contaminant clearance rates in the presence of liposomes was slightly reduced when compared to their clearance rates in the absence of liposome due to nonspecific interactions between the contaminants and the liposomes in solution. This is most evident in the case of Coumarin 343 as it is a relatively hydrophobic small molecule that is capable of imbedding into the lipid bilayer. Adding the absorbance spectrums of the Post-LEP and FT nearly perfectly overlay with the Pre-LEP sample demonstrating very little loss of liposome or contaminate to the system (FIG. 21). Contaminate clearance results and total liposome recoveries are summarized in Table 3.1.

TABLE 3.1

Liposome recovery and contaminant clearance of mixed liposome and contaminant samples.

| | Contaminant | Liposome Recovery (%) | Contaminant Reduction (%) | Contaminant (Fold Reduction) |
|---|---|---|---|---|
| No Liposome | C343 | — | 93.36 ± 0.24 | 15.1 |
| | BSA | — | 93.83 ± 0.39 | 16.2 |
| | Trastuzumab | — | 93.70 ± 0.49 | 15.9 |
| Liposome | C343 | 93.79 ± 0.50 | 92.90 ± 1.24 | 14.1 |
| | BSA | 91.45 ± 1.12 | 93.66 ± 1.39 | 15.8 |
| | Trastuzumab | 92.19 ± 3.24 | 93.52 ± 0.85 | 15.4 |

To demonstrate the utility and breadth of the LEP technique, various liposome formulations were selected and tested to assess liposome recovery. As can be seen in Table 3.2, >94% of the diverse liposome formulations were recovered after a single LEP cycle.

TABLE 3.2

Recovery of various liposome formulations after one LEP cycle.

| Sample | Liposome Size (nm) | PEG (%) | PEG MW (Da) | LEP Membrane (nm) | Liposome Recovery (%) |
|---|---|---|---|---|---|
| 1 | 100 | 0 | 0 | 50 | 97.58 ± 1.28 |
| 2 | 100 | 5 | 350 | 50 | 97.43 ± 0.37 |
| 3 | 100 | 5 | 1000 | 50 | 97.93 ± 0.40 |
| 4 | 100 | 5 | 2000 | 50 | 94.37 ± 2.90 |
| *5 | 100 | 5 | 2000 | 50 | 96.01 ± 4.81 |
| 6 | 100 | 1 | 2000 | 50 | 97.59 ± 1.02 |
| 7 | 100 | 5 | 2000 | 30 | 96.84 ± 1.11 |
| 8 | 50 | 5 | 2000 | 30 | 87.12 ± 1.55 |

*Indicates three LEP cycles.

Figure 22:
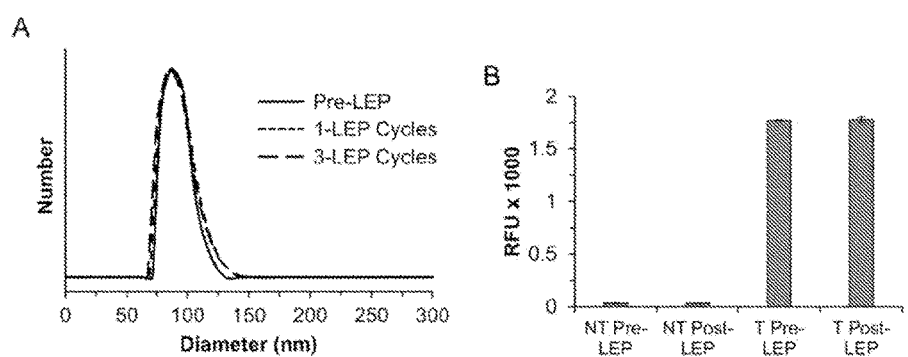
FIG. 22. A) Liposome size distribution determined by dynamic light scattering (DLS) Pre- and Post-LEP. Liposomes were formed via extrusion through a 100 nm pore size membrane and LEP was carried out using a 50 nm pore size membrane. B) In-vitro cellular uptake assay using targeted liposomes (T) Pre- and Post-LEP compared to non-targeted control liposomes (NT) as determined via flow cytometry.

It is important that the purification technique employed is not detrimental to the liposomes and that the process does not affect their ability to carry out their designated function. A significant indicator of liposome integrity is its hydrodynamic diameter, which can be determined by dynamic light scattering (DLS). Common problems associated with liposome purification are aggregation and a reduction in liposome size due to excessive stress on the bilayer; both of which can be assessed by DLS. DLS was carried out on all liposome samples both before and after LEP was performed. In all cases the process resulted in no effect on the LEP purified liposome size distribution (FIG. 22A).

Figure 23:
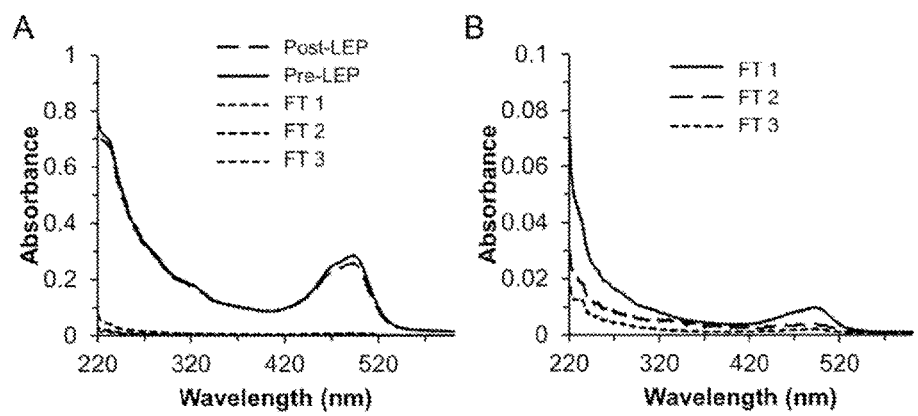
FIG. 23. A) Absorbance scans of 3 cycles of LEP being performed on a single liposome sample demonstrating a liposome recovery of 96.01±4.81%. B) Absorbance scans of the flow through (FT) from each of the 3 LEP cycles showing a reduced flow through of liposomes through the membrane with each consecutive LEP cycle. The initial flow through shows a liposome absorbance of 0.0096 at 494 nm which is <3.5% of the initial liposome sample with significantly less liposome passing through the membrane in the second and third FT fractions. This process demonstrates a ~14-16 fold reduction in contaminate after each LEP cycle with a final reduction in contaminate of ~2750-4100 fold after 3 cycles.
Figure 24:
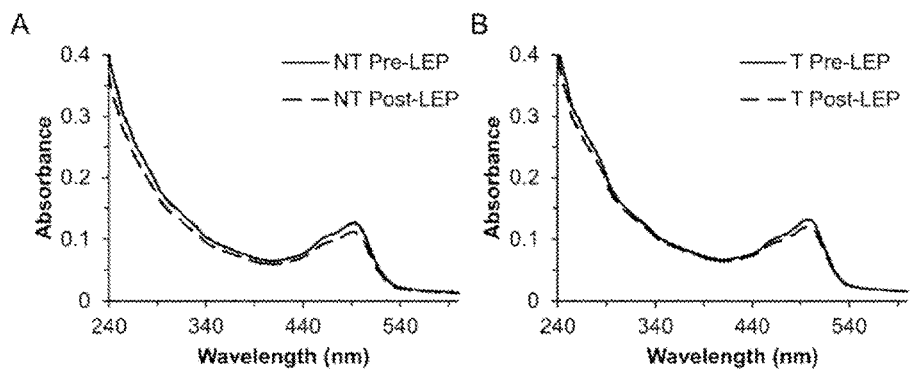
FIG. 24. A) Absorbance scans of the non-targeted (NT) liposomes Pre- and Post-LEP demonstrating a liposome recovery of 89.2% (94.5:10:5:0.5 HSPC:CHOL:mPEG2000-DSPE:CF-PE). B) Absorbance scans of the targeted (T) liposomes Pre and Post-LEP demonstrating a liposome recovery of 91.3% (93.5:10:5:1:0.5 HSPC:CHOL:mPEG2000-DSPE:VLA4-pep:CF-PE).
Figure 25:
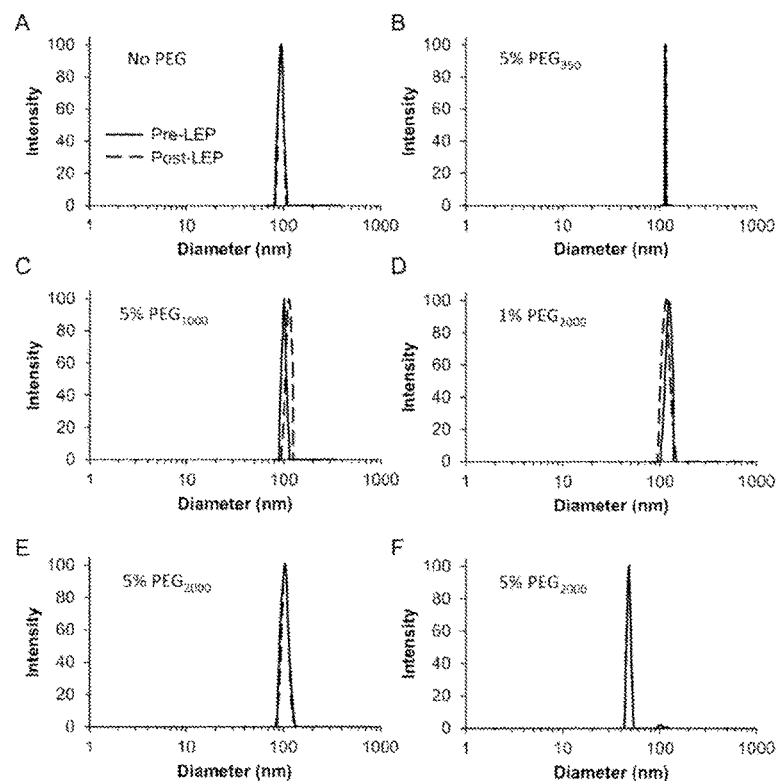
FIG. 25. DLS data for the diverse liposome formulations tested to verify no aggregation or liposome fragmentation occurring as a result of the LEP process. A) No PEG, 100 nm liposome, 50 nm LEP membrane. B) 5% PEG350, 100 nm liposome, 50 nm LEP membrane. C) 5% PEG1000, 100 nm liposome, 50 nm LEP membrane. D) 1% PEG2000, 100 nm liposome, 50 nm LEP membrane. E) 5% PEG2000, 100 nm liposome, 30 nm LEP membrane. F) 5% PEG2000, 50 nm liposome, 30 nm LEP membrane.

To further verify that the LEP process was not detrimental to the liposome, a cell targeting liposome uptake assay was carried out in which LEP was performed on targeted and non-targeted liposome formulations and cellular uptake was assessed via flow cytometry. As shown in FIG. 22B, there is no change in the amount of fluorescently labeled liposomes that were taken up by the cells Pre- or Post-LEP with the targeted or non-targeted liposomes, demonstrating that LEP had no negative effects on the liposome targeting. In this case, the targeting moiety on the liposome was a peptide modified lipid incorporated directly in the liposome formulation at the time of extrusion and therefore LEP was carried out to simply test its effect on targeting and not for the purposes of purification. Absorbance spectrums for the 3-LEP sample, targeted and non-targeted Pre- and Post-LEP samples are shown in FIGS. 23 and 24. DLS was carried out on all liposome formulations tested and a summary of the results are shown in FIG. 25. Liposomes were purified as previously described using a 30 nm polycarbonate membrane.

Confocal Microscopy. Liposomes were added at 100 μM phospholipid concentration and incubated for 3 hours at 37° C. 1% Rhodamine-PE was added as a fluorescent marker to each liposomal formulation. After incubation, cells were washed 3 times with PBS and spun onto slides, using a Cytospin (Thermo Fisher Scientific, Waltham, Mass.) before being fixed with 4 w/w % paraformaldehyde. Coverslips were mounted on microscope slides with VectaShield antifade/DAPI (Vector Labs, Burlingame, Calif.). Cells were visualized by Nikon A1R confocal microscope with a 40× oil lens (Nikon Instruments, Melville, N.Y.). Image acquisition was performed by Nikon Elements Ar software (Nikon).

Carfilzomib Loading and Release Analysis. Liposomes were purified as previously described using a 30 nm polycarbonate membrane. The filtrate was collected, then analyzed for the carfilzomib content using Zorbax semi-preparative C3 column on the Agilent series 1200 HPLC, monitoring the absorbance at 220 nm and 265 nm.

MM Xenograft Mouse Model. C.B.-17 SCID mice (Harlan Laboratories) were irradiated with 150 rad and were inoculated subcutaneously with $5 \times 10^6$ NCI-H929 cells. When tumors were palpable, mice were distributed into 6 groups of 5 mice and were treated intravenously with the various bortezomib pro-drugs, free bortezomib, or vehicle (PBS), on days 1, 4, 8, and 11. Animals were monitored for body weight and tumor volume.

Hydrolysis of Boronic Esters. The isobutylboronic ester hydrolysis was monitored using $^{11}$B-NMR. Hydrolysis of the bortezomib pro-drugs were analyzed using Zorbax semi-preparative C3 column on the Agilent series 1200 HPLC, monitoring the absorbance at 220 nm and 265 nm.

Synthesis of VLA4-Pep-EG6-Lipid Conjugate. Ligands were synthesized using Fmoc chemistry on a solid support using the Wang resin. The molecules were cleaved from the resin with 94/2.5/2.5/1 TFA/H$_2$O/EDT/TIS and purified using RP-HPLC on an Agilent (Santa Clara, Calif.) 1200 series system with a semi-preparative Zorbax C3 column with isopropanol gradients in the mobile phase. The purified product was characterized using a Bruker Autoflex III Smartbeam Matrix Assisted Laser Desorption Ionization Time of Flight Mass Spectrometer (MALDI-ToF-MS, Billerica, Mass.). Peptide cyclization through disulfide bond formulation was performed in DMF with DIEA under stirring overnight.

Synthesis of 2-((2-hydroxyethyl)amino)acetic acid. 2 mmol of ethanolamine and 2 mmol of diisopropylethylamine were mixed together in 30 mL of methanol in a flame-dried 200 mL round bottom flask. 2 mmol of methyl bromoacetate was added dropwise into the solution while stirring. The flask was connected to a partial condenser (T=5° C.) and set in an oil bath (T=85° C.). The reaction was stirred and proceeded under reflux overnight. The solution was cooled to room temperature and the solvent was removed via rotary evaporation. The solids were dissolved in 1.3 mL of EtOH and diluted into 6 mL of 1 M NaOH. The solution was allowed to reflux for 1 hour. The pH of the solution was then adjusted to pH=7 with HCl and evaporated to dryness. Mass spec analysis shows [M+H]=120.0691 m/z.

Synthesis of 2,2'-(hexadecylazanediyl)diacetic acid. Hexadecylamine (1.81 g, 7.5 mmol) was dissolved in 75 mL of MeOH in a flame-dried 250 mL round bottom flask. Diisopropylethylamine (3.92 mL, 30 mmol) and 2.29 g of methyl bromoacetate (15 mmol) were added to the flask while stirring. The flask was connected to a partial condenser (T=5° C.) and set in an oil bath (T=85° C.). The solution was stirred and allowed to react under reflux for 96 hours. After the 96 hours, the solvent was removed via rotary evaporation and the solids were dissolved in chloroform. The intermediate product was purified via flash chromatography. The solution was concentrated then diluted into 400 mL of 0.5 M NaOH. The solution was boiled until it turned clear (approx. 2 hours). The solution was then cooled to room temperature and the pH was adjusted to pH=2 using 10 M HCl. White precipitate formed and the product was filtered, washed, and allowed to dry in vacuo overnight. Mass spec analysis shows [M+H]=358.2899 m/z.

Synthesis of 2-(hexadecyl(2-hydroxyethyl)amino)acetic acid. Bromohexadecane (3.05 g, 10 mmol) was diluted in 50 mL of MeOH in a flame-dried 250 mL round bottom flask. 671.8 mg of ethanolamine (11.1 mmol) along with ~3 mL of diisopropylethylamine (~20 mmol) was added to the solution. The flask was connected to a partial condenser (T=5° C.) and set in an oil bath (T=85° C.). The solution was stirred and allowed to react under reflux for 24 hours. The solution was then evaporated to dryness then dissolved in 35 mL of MeOH. Diisopropylethylamine (~3 mL, ~20 mmol) and 1.5 g of methyl bromoacetate (10 mmol) was added to the solution. The flask was connected to a partial condenser (T=5° C.) and set in an oil bath (T=85° C.). The solution was stirred and allowed to react under reflux for 96 hours. After the 96 hours, the solvent was removed via rotary evaporation and the solids were dissolved in chloroform. The intermediate product was purified via flash chromatography. The solution was concentrated then diluted into 400 mL of 0.5M NaOH. The solution was boiled until it turned clear (approx. 2 hours). The solution was cooled to room temperature and pH adjusted to pH=2 using 10 M HCl. White precipitate formed and the product was filtered, washed, and allowed to dry in vacuo overnight. Mass spec analysis shows [M+H]=344.3191 m/z.

Synthesis of 2,2'-(hexadecylazanediyl)diethanol. Diethanolamine (1.06 g, 11.1 mmol) was diluted in 75 mL of MeOH in a flame-dried 250 mL round bottom flask. 3.48 mL of diisopropylethylamine (20 mmol) was added to the solution. 3.05 g of bromohexadecane (10 mmol) was added to the solution while stirring. The flask was connected to a partial condenser (T=5° C.) and set in an oil bath (T=85° C.). The solution was stirred and allowed to react under reflux for 96 hours. After the 96 hours, the solution was concentrated via rotary evaporation before being diluted into 50 mL of water. White precipitate formed and the product was filtered, washed, and allowed to dry in vacuo overnight. Mass spec analysis shows [M+H]=330.3390 m/z.

Synthesis of N,2-dihydroxy-4-methylbenzamide. 4-Methylsalicylic acid (252.5 mg, 1.66 mmol) was dissolved with 20 mL of MeOH in a 50 mL round bottom flask. 0.5 mL of concentrated sulfuric acid was added while stirring. The flask was connected to a partial condenser (T=5° C.) and set in an oil bath (T=85° C.). The solution was stirred and allowed to react under reflux for 24 hours. The reaction was quenched by adding 100 mL of water to the solution. The intermediate was extracted with ethyl ether (3×30 mL). The organic phases were combined and washed with a saturated sodium bicarbonate solution (2×100 mL). The ether was evaporated in vacuo and the intermediate was dissolved in 0.5 mL of THF. In a separate vial, 6.72 mL of 1.64 M hydroxylamine in water was added to 8.38 mL of 3 M NaOH. The intermediate solution was added drop wise to the NaOH/NH$_2$OH solution while stirring. The reaction was allowed to proceed at room temperature for 24 hours. After 24 hours, the reaction was cooled to 0° C. using an Ice bath, and the pH was adjusted to pH=5 with 10 M HCl. The solution was allowed to warm to room temperature before extracting the product with ethyl acetate (3×15 mL). The organic layers were combined and the solvent was evaporated. Mass spec analysis shows [M+H]=168.0711 m/z.

Synthesis of 4-((hexadecylamino)methyl)-2-hydroxybenzoic acid. 1.521 g of methyl salicylic acid (10 mmol) was dissolved in 50 mL of MeOH in a 200 mL round bottom flask. 3 mL of concentrated sulfuric acid was added to the solution. The flask was connected to a partial condenser (T=5° C.) and set in an oil bath (T=85° C.). The solution was stirred and allowed to react under reflux for 24 hours. The reaction was quenched by adding 100 mL of water to the solution. The intermediate was extracted with ethyl ether (3×50 mL). The organic phases were combined and washed with a saturated sodium bicarbonate solution (2×100 mL). The ether was evaporated in vacuo and the intermediate was dissolved in 40 mL of carbon tetrachloride. 2.225 g of N-bromosuccinimide (12.5 mmol) and 0.726 g of benzoyl peroxide (3 mmol) were mixed in the solution. The flask was connected to a partial condenser (T=5° C.) and set in an oil bath (T=85° C.). The solution was stirred and allowed to react under reflux for 4 hours. The brominated intermediate was purified via flash chromatography and concentrated to a volume of 5 mL. The concentrate solution, 2.4 g of hexadecylamine (10 mmol), and 2.5 g of diisopropylethylamine (20 mmol) were mixed in 70 mL of MeOH. The flask was connected to a partial condenser (T=5° C.) and set in an oil bath (T=85° C.). The solution was stirred and allowed to react under reflux for 24 hours. After the 24 hours, the solvent was removed via rotary evaporation and the solids were dissolved in chloroform. The intermediate product was purified via flash chromatography. The solution was concentrated then diluted into 400 mL of 0.5 M NaOH. The solution was allowed to boil for 2 hours. White precipitate formed and the product was filtered, washed, and allowed to dry in vacuo overnight. Mass spec analysis shows [M+H]=392.3116 m/z.

Synthesis of 2,3-dimethylhenicosane-2,3-diol. Octadecylmagnesium chloride (4 mL, 0.5 M, 2 mmol) in THF was placed in a flame dried vial. 3-Hydroxy-3-methyl-2-butone (204.3 mg, 2 mmol) was diluted in 1 mL of diethyl ether. The ether solution was added drop wise into the THF solution. The reaction was stirred and allowed to proceed for 2 hours. The solution was diluted in 60 mL of 1 M HCl to quench the reaction. The product was extracted with 3×30 mL of diethyl ether. The organic phases were combined and the solvent removed via evaporation. Mass spec analysis shows [M+H]=357.3527.

Synthesis of the Boronic Acid Conjugates. The boronic acid and the respective molecule (R=A, B, or C) were placed in a flame dried 25 mL flask along with 7 mL of toluene. The flask was placed in an oil bath (T=125° C.) and connected to a condenser (T=5° C.). The solution was allowed to reflux for 2 hours before being removed from the heat. The solvent was then evaporated in vacuo. Conjugation was verified using $^{11}$B-NMR spectroscopy via Bruker 400 MHz spectrometer.

A. Carfilzomib Results. Carfilzomib, a second generation proteasome inhibitor, has been recently approved by the FDA for the treatment of multiple myeloma (MM). Due to its low solubility in water, carfilzomib has to be administered with the aid of sulfobutyl ether beta cyclodextrin (Captisol®) to improve its solubility for clinical use. In such formulations, carfilzomib binds inside the ring of the cyclodextrin which improves its solubility in aqueous solution.

Figure 26:
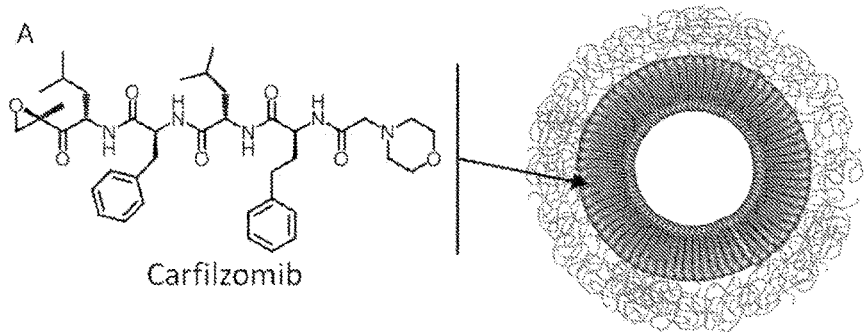
FIG. 26. A) Illustration of carfilzomib loaded liposomes. B) Dynamic light scattering analysis of the liposomes. All carfilzomib loaded liposomes gave the same average size distribution of ~70 nm.
Figure 26:
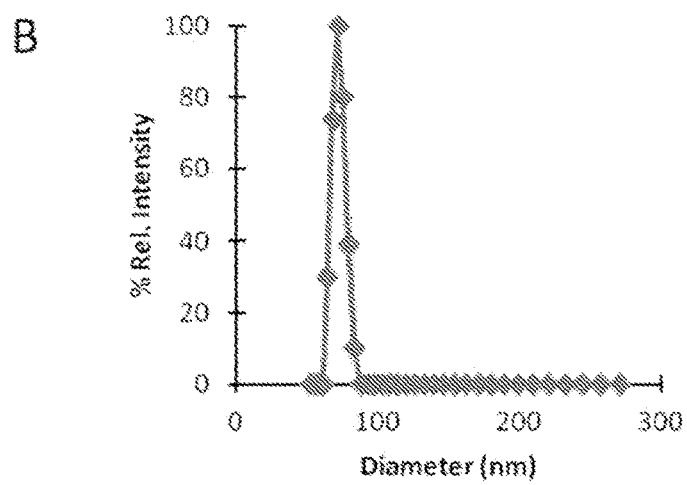

Carfilzomib Embedded in the Bilayer of Stealth Liposomes. Carfilzomib was embedded into the bilayer of liposomes by mixing it with lipids in an organic solution prior to forming the lipid film. When the lipid film is hydrated, carfilzomib remains in the bilayer due to hydrophobic interactions and takes advantage of the EPR effect and longer circulation times conferred by the liposomes' size, ~70 nm, and PEG coating (FIGS. 26A and 26B). In addition, targeting moieties can be incorporated into the liposomes to further enhance accumulation of the drug in the tumor.

Figure 27:
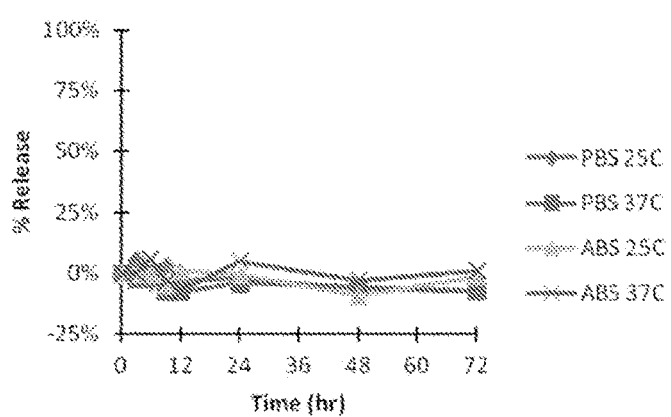
FIG. 27. Release of carfilzomib from the liposomes. Carfilzomib in solution was purified away from the liposomal carfilzomib and HPLC analysis was used to assess the amount released. Top: percent carfilzomib released over a 72 hour time period. Bottom: chromatograms (mAu) of the free carfilzomib in solution.
Figure 27:
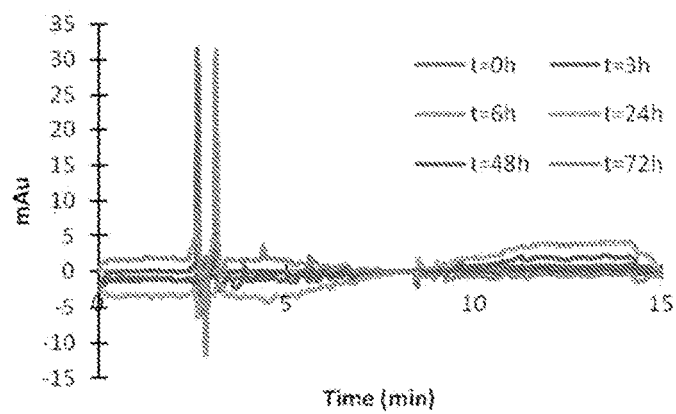

Embedding carfilzomib in the liposome bilayer reduces the non-specific toxicity associated with the free drug. The release profile of the liposomes indicates that carfilzomib is not released from the liposomes regardless of temperature or pH (FIG. 27). This indicates that the drug is only released when the liposomes are degraded within the cell.

Figure 28:
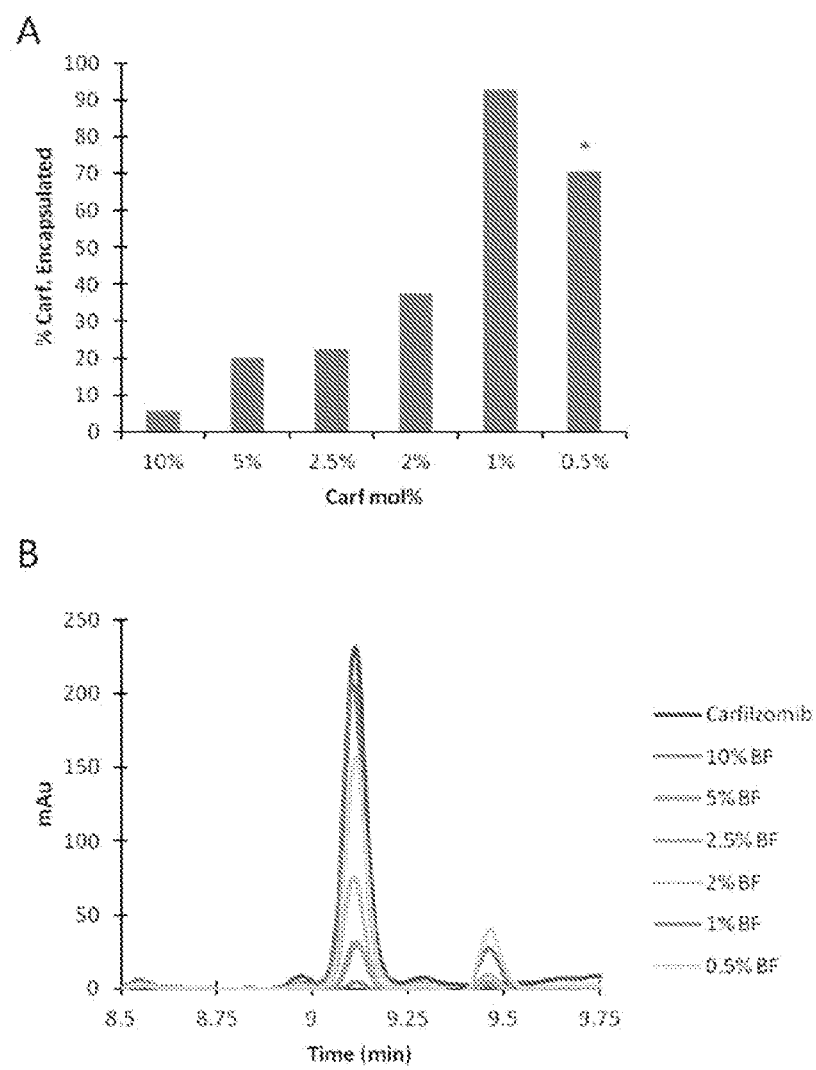
FIG. 28. Loading efficiency of carfilzomib into liposomes at various molar ratios. A) Bar graph depicting the total percent of carfilzomib embedded in the liposomes. B) Chromatograms of carfilzomib-loaded liposomes after being purified away from the free drug in solution. *The reduced percentage in loading efficiency is due to losses during purification.

An optimal loading of carfilzomib is about 1 mol % of the lipid concentration. Increasing the carfilzomib molar percentage reduces the loading efficiency of embedded carfilzomib (FIG. 28A). The amount of embedded carfilzomib was determined by using liposome extruder purification in conjunction with HPLC analysis (FIG. 28B).

Figure 29:
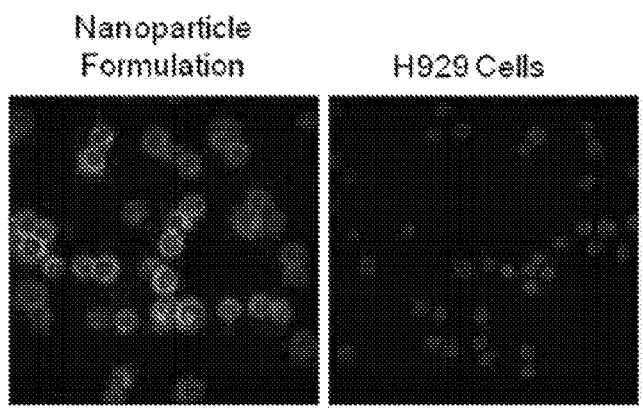
FIG. 29. Confocal images of cellular uptake of rhodamine labeled liposomes using a Nikon A1R confocal microscope with a 40× oil lens. The nanoparticles are the same formulation used in the in vitro and in vivo studies except without drug loading. Image acquisition was performed by Nikon Elements Ar software.
Figure 30:
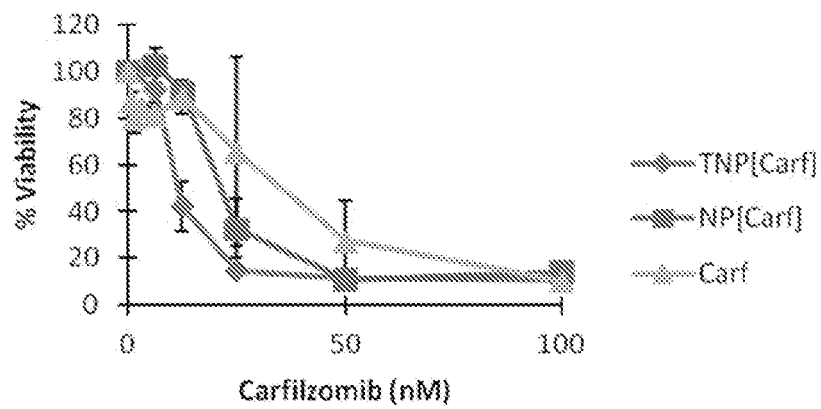
FIG. 30. Cytotoxic assays of free carfilzomib, non-targeting liposomal carfilzomib, and targeting liposomal carfilzomib. MM.1S (top) and NCI-H929 (bottom) cells were cultured in the presence of the equivalent carfilzomib concentrations for 48 hours. Cell viability was assessed using Cell Counting Kit-8 and data represents means of (±s.d.) of triplicate cultures.
Figure 30:
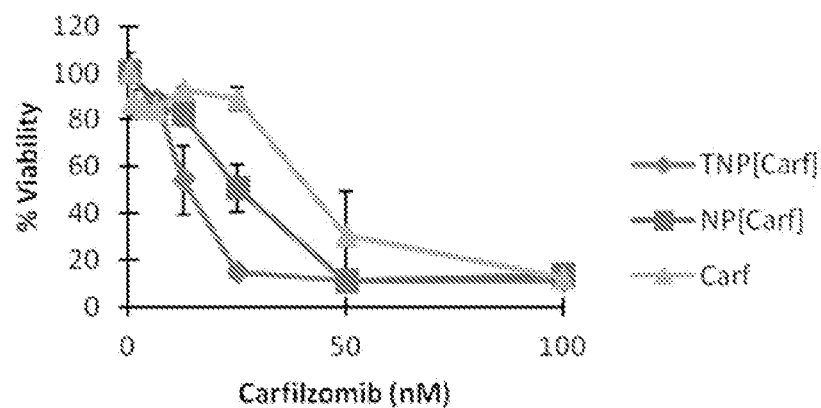

Liposomal Carfilzomib is Cytotoxic to Multiple Myeloma Cell-Lines. We have demonstrated that the peptide targeted liposome formulation without any drug loading were taken up by cell-lines expressing VLA-4. Confocal microscopy experiments show that the liposomes are taken up by the cells (FIG. 29), with the targeted liposomes taken up by the cells at a significantly increased rate compared to the non-targeting liposomes. With this knowledge, carfilzomib was loaded into liposomes and the cytotoxicity was evaluated and compared to that of the free drug (FIG. 30). The results show that the targeting and non-targeting liposomes display equal or greater cytotoxicity to multiple myeloma cell-lines compared to the free drug.

B. Bortezomib Results.

Figure 31:
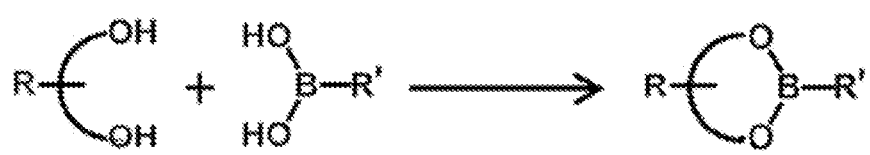
FIG. 31. Schematic of the formation of boronic esters.

Screening for Viable Boronic Ester Coniugates for the Creation of Bortezomib Pro-Drugs. Bortezomib contains a boronic acid moiety which plays a major role in its ability to inhibit proteasome activity. Boronic acids are known to form boronic esters with diol-containing molecules, or molecules that have moieties conducive to boronic ester formation (FIG. 31). These boronic ester bonds are also known to be pH sensitive. By creating such a bond to the boronic acid on bortezomib, it can be used to create a pro-drug that will render bortezomib inactive until it is delivered to the diseased site, thereby reducing the amount of non-specific toxicities associated with the therapeutic.

Figure 32:
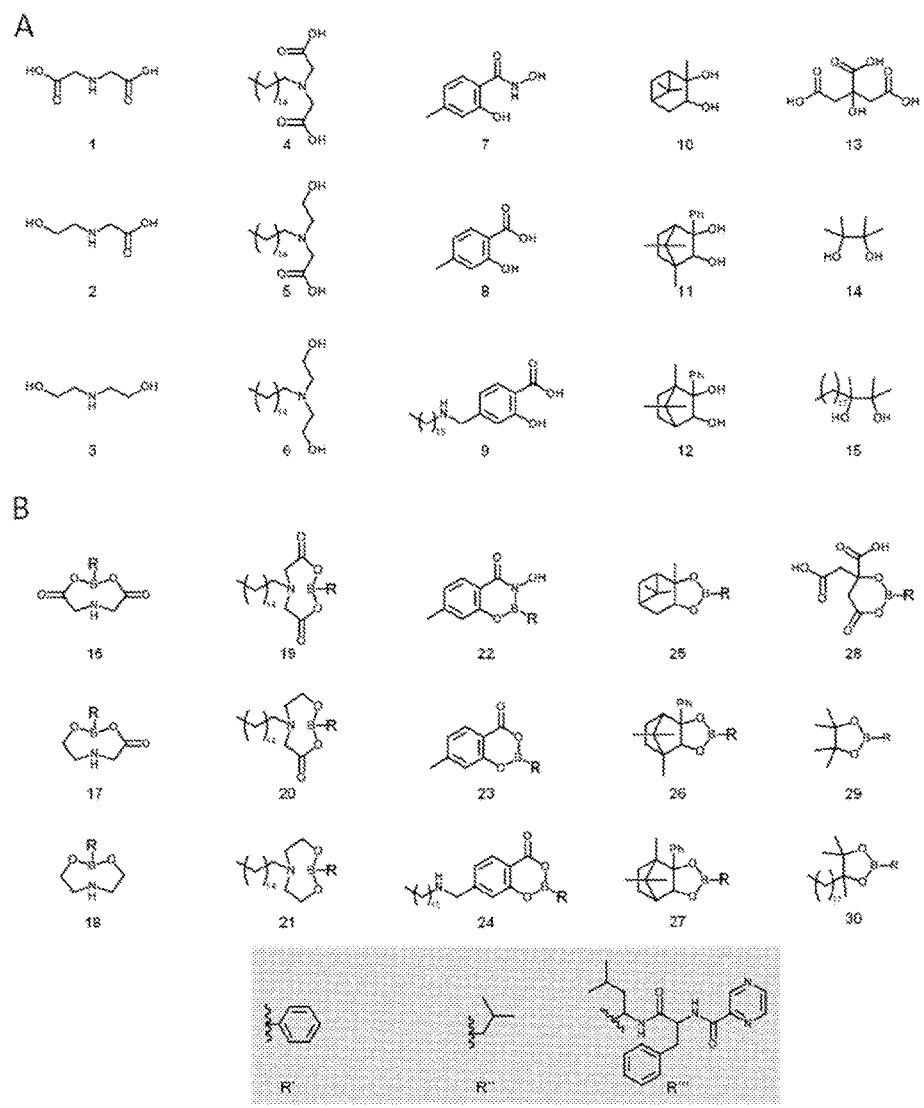
FIG. 32. A) Molecules to be screened based on the formation of stable boronic esters for the creation of a bortezomib pro-drug and their B) respective boronic ester conjugates (i.e., 14 is the conjugate of 1). To form a distinction between the different boronic acids conjugated to the same molecule, the following notation applies: R'=A; R''=B; R'''=C.

Many studies have been performed observing the formation of boronic esters. Unfortunately, the molecule primarily used in the studies is phenylboronic acid (PBA) which, due to the electron structure surrounding the boronic acid, forms more stable boronic esters than bortezomib with various molecules. Thus, to find a viable molecule to conjugate to the boronic acid of bortezomib, isobutylboronic acid (IBBA) was selected to screen various molecules to search for a molecule that forms a stable boronic ester (FIGS. 32A and 32B). Isobutylboronic acid was chosen for the initial screening of molecules instead of bortezomib because it is more conducive for the rapid screening of multiple molecules and has a similar structure surrounding the boronic acid.

Initially, PBA was conjugated to a select few molecules, 19A and 22A, to validate the stability recorded in literature. After verifying the stability via $^{11}$B-NMR, isobutylboronic acid was substituted for PBA in forming the boronic ester conjugates. Molecules 1, 2, 3, and 8 (FIG. 32A) proved to be viable candidates and were modified to incorporate an alkyl chain for incorporation into liposomes. After conjugation to IBBA, 19B, 20B, 21B, and 24B were incorporated into liposomes before evaluating the rate of hydrolysis. The hydrolysis profiles of these molecules show that they exhibit similar hydrolysis rates to their non-alkylated counter-parts. Thus, these molecules were selected for further evaluation with bortezomib.

Figure 33:
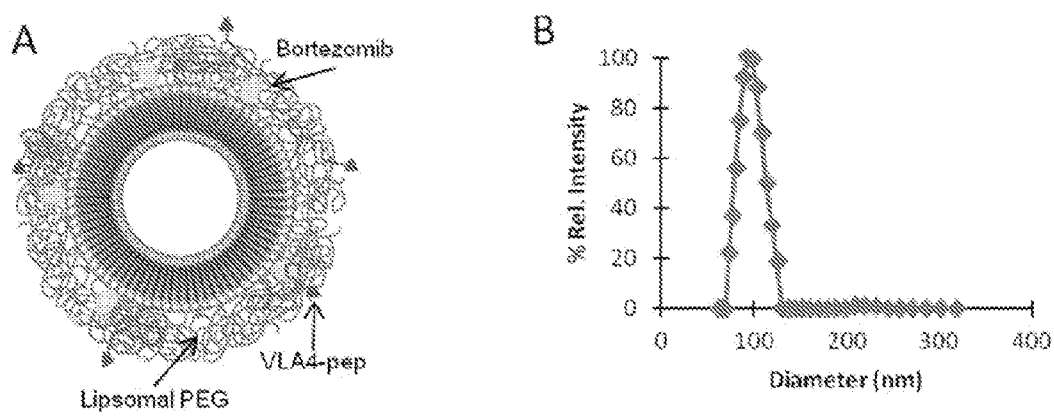
FIG. 33. A) Illustration of multifunctional liposomes that incorporate VLA4-pep and the bortezomib pro-drugs. B) Dynamic light scattering analysis of the liposomes. All liposomes gave the same average size distribution of ~100 nm.

Incorporation of the Bortezomib Pro-Drug Candidates into Liposomes. Pro-drug candidates, 19C, 20C, 21C, and 24C, were synthesized and incorporated into liposomes (FIG. 33A). The liposomes' average diameter was determined to be ~100 nm using dynamic light scattering analysis (FIG. 33B), which indicates that the incorporation of the pro-drugs does not alter the size of the liposomes.

Figure 34:
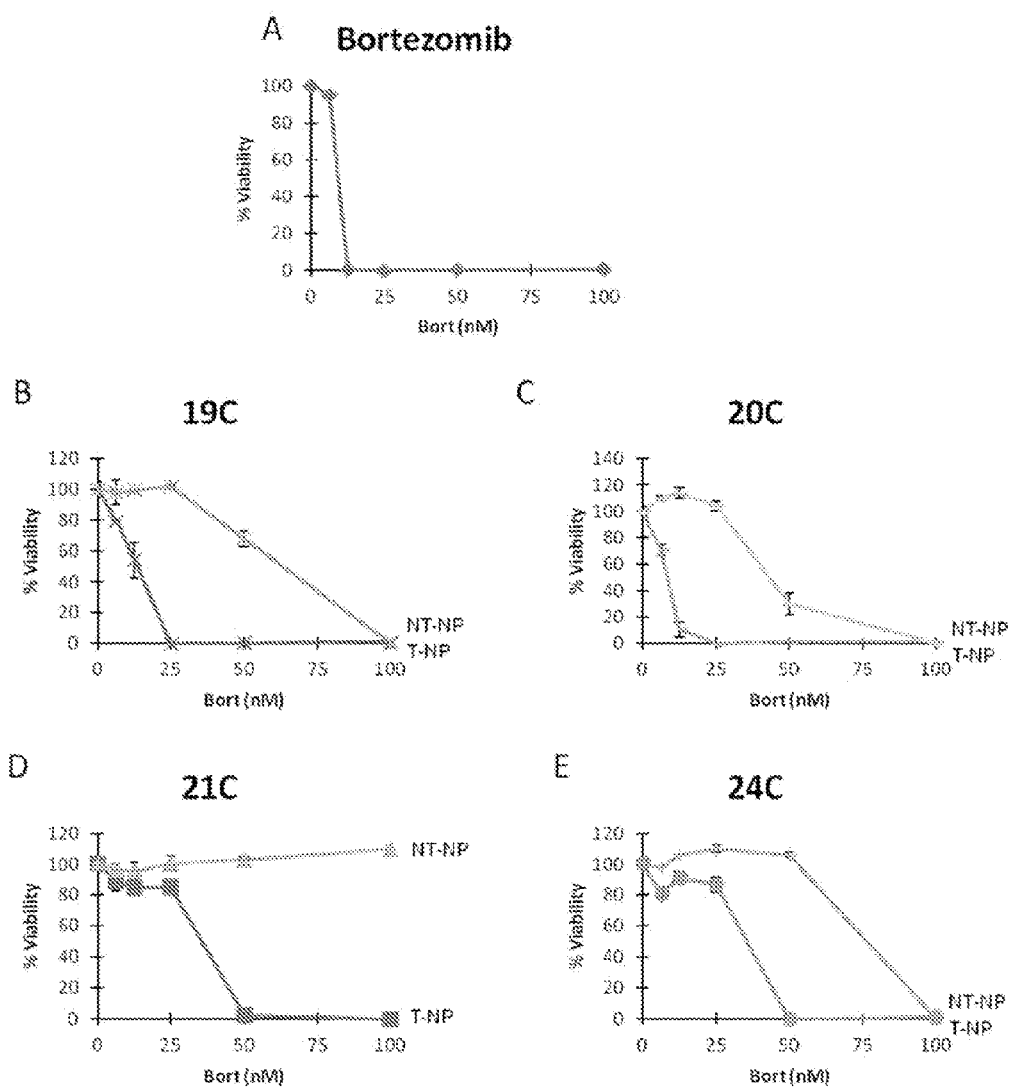
FIG. 34. Cytotoxic assays of A) free bortezomib, B) liposomal 19C, C) liposomal 20C, D) liposomal 21C, and E) liposomal 24C. For liposomal pro-drug, targeting and non-targeting liposomes were evaluated. MM.1S cells were cultured in the presence of the equivalent bortezomib concentrations for 48 hours. Cell viability was assessed using Cell Counting Kit-8 and data represents means of (±s.d.) of triplicate cultures.

Pro-Drug Candidates are Cytotoxic to Multiple Myeloma Cells. Even though the bortezomib drug conjugates are less stable than boronic esters formed with IBBA, they can still prove to be effective in delivering the therapeutic while reducing overall toxicity. Therefore, the cytotoxic effects of the pro-drugs were evaluated with multiple myeloma cell lines MM.1S and NCI-H929. Both a non-targeted liposome and a peptide-targeted liposome against the VLA-4 integrin were examined. The results show that there is a significant difference between the targeting and non-targeting pro-drug liposomes, with the targeting liposomes being, in some cases, significantly more cytotoxic to the cells than the non-targeting liposomes (FIG. 34B-E). Although the drug-loaded liposomes are effective in inhibiting cell growth, they are not as effective as the free bortezomib (FIG. 34A). This difference could be attributed to the difference in uptake pathways between the liposomes and the free drug. Confocal microscopy experiments show that the liposomes are taken up by the cells (FIG. 29), with the targeted liposomes being taken up by cells at a significantly increased rate compared to the non-targeting liposomes.

Liposomal Pro-Drugs Inhibit Tumor Growth with Reduced Systemic Toxicity In Vivo. The cytotoxicity of the pro-drug candidates observed with the in vitro studies suggests potential in vivo efficacy. Thus, in vivo studies were performed on C.B-17 SCID mice injected with NCI-H929 tumors to evaluate the efficacy of the liposomal pro-drugs in inhibiting tumor growth and limiting toxicity. The mice were divided into six groups (control, free bortezomib, and one group for each pro-drug) of five mice. The mice were monitored for body weight and tumor volume every other day. When the tumors became palpable, intravenous injections of the respective bortezomib formulations at a dose of 1 mg/kg bortezomib equivalent nanoparticles were performed on days 1, 4, 8, and 11.

Figure 35:
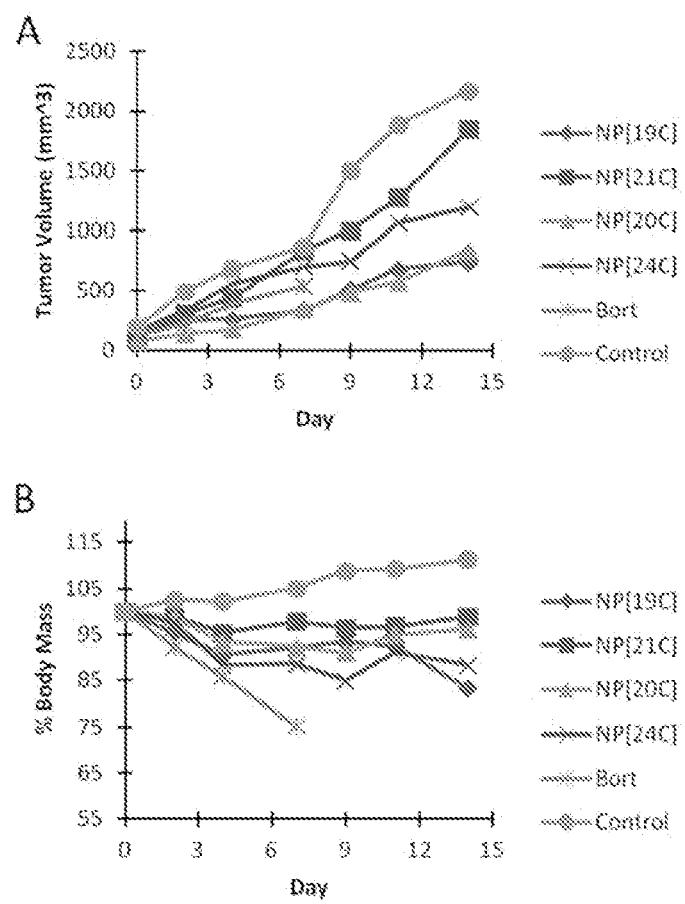
FIG. 35. In vivo characterization of bortezomib pro-drugs in a xenograft multiple myeloma model. Tumor bearing SCID mice were injected on days 1, 4, 8, and 11 with the different bortezomib formulations at a dose of 1 mg/mg. A) Tumor volume was measured via calipers. B) Percentage of body weight of the animals as a measure of systemic toxicity. The mice in the free bortezomib group showed moribundity by day 7. Therefore, mice in this group were sacrificed on day 7.

The results indicate that pro-drugs 19C and 24C were as efficacious in tumor growth inhibition as free bortezomib while reducing systemic toxicity, evident by the reduced weight loss (FIG. 35A). The drug-loaded liposomes resulted in <15% loss in mass while the mice injected with free bortezomib showed moribundity on day 7 and were sacrificed (FIG. 35B). This demonstrates the improved therapeutic index of the liposomal bortezomib pro-drugs.

Example 4

Pharmaceutical Dosage Forms

The following formulations illustrate representative pharmaceutical dosage forms that may be used for the therapeutic or prophylactic administration of a liposome or micelle composition described herein, or a combination of compositions described herein (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |

| (x) Topical Cream 1 | wt. % |
| --- | --- |
| Polysorbate 80 | 2% |
| Methyl paraben | 0.2% |
| Purified water | q.s. to 100 g |

| (x) Topical Cream 1 | wt. % |
| --- | --- |
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
| --- | --- |
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient in 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A pharmaceutical composition comprising liposomes that contain one or more anticancer drugs wherein the liposomes comprise:

a) a phospholipid and optionally a lipid that is not a phospholipid;

b) a pegylated lipid;

c) a targeting ligand (TL)-ethylene glycol (EG)-lipid conjugate wherein the targeting ligand is a peptide, an antibody, an antibody fragment, or a small molecule;

d) one or more drug-conjugated lipids, encapsulated drugs, or a combination thereof; and e) a hydrophilic oligolysine chain between the TL and the EG moiety comprising two to six lysine units;

wherein the ethylene glycol (EG) segment of the TL-EG-lipid conjugate is EG6 to about EG36; and the EG segment is conjugated to a second lysine moiety wherein the conjugation comprises an amide linkage, and wherein the second lysine moiety is conjugated to two ($C_{14}$-$C_{24}$)acyl moieties through amide bonds.

2. The pharmaceutical composition of claim 1 wherein the phospholipid is hydrogenated soy L-α-phosphatidylcholine (HSPC).

3. The pharmaceutical composition of claim 1 wherein the lipid that is not a phospholipid is cholesterol.

4. The pharmaceutical composition of claim 1 wherein the pegylated lipid is polyethylene glycol-1,2-distearoyl-sn-glycero-3-phosphoethanolamine (PEG-DSPE).

5. The pharmaceutical composition of claim 1 wherein the pegylated lipid has about 6 repeating PEG moieties to about 30 repeating PEG moieties.

6. The pharmaceutical composition of claim 1 wherein the peptide of the peptide-EG-lipid conjugate is HER2-pep (SEQ ID NO: 1).

7. The pharmaceutical composition of claim 1 wherein the peptide of the peptide-EG-lipid conjugate is VLA4-pep (SEQ ID NO: 2).

8. The pharmaceutical composition of claim 1 wherein the $(C_{14}-C_{24})$acyl moieties are palmitate moieties.

9. The pharmaceutical composition of claim 1 wherein about 5% of the molecules of the liposome are PEG350-lipids.

10. The pharmaceutical composition of claim 1 wherein the components of the liposome comprise HSPC, cholesterol (CHOL), DSPE-PEG2000 or DSPE-PEG350, and an encapsulated free drug, wherein the peptide moiety of the peptide-EG-lipid conjugate is VLA4-pep.

11. The pharmaceutical composition of claim 10 wherein the components HSPC:CHOL:DSPE-PEG2000:VLA4-pep, or the components HSPC:CHOL:DSPE-PEG350:VLA4-pep, are present in a molar ratio of about 95:10:3:2, wherein the term about refers to a variation of plus or minus 20%.

12. The pharmaceutical composition of claim 1 wherein the components of the liposome comprise HSPC, cholesterol (CHOL), DSPE-PEG2000 or DSPE-PEG350, and an encapsulated free drug, wherein the peptide moiety of the peptide-EG-lipid conjugate is HER2-pep.

13. The pharmaceutical composition of claim 12 wherein the components HSPC:CHOL:DSPE-PEG2000:HER2-pep, or the components HSPC:CHOL:DSPE-PEG350:HER2-pep are present in a molar ratio of about 95:10:3:2, wherein the term about refers to a variation of plus or minus 20%.

14. The pharmaceutical composition of claim 1 wherein the peptide-EG-lipid conjugate comprises about 1 mol % to about 3 mol % of the molecules in the liposomes.

15. The pharmaceutical composition of claim 1 wherein the peptide-EG-lipid conjugate comprises about 2 mol % of the molecules in the liposomes.

16. The pharmaceutical composition of claim 1 wherein the targeting ligand is an antibody, an antibody fragment, or a small molecule.

17. The pharmaceutical composition of claim 1 wherein the diameter of the liposomes is about 30 nm to about 200 nm.

18. The pharmaceutical composition of claim 1 wherein the diameter of the liposomes is about 90 nm to about 110 nm.

19. The pharmaceutical composition of claim 1 wherein the $(C_{14}-C_{24})$acyl moiety is a straight chain or branched, saturated or partially unsaturated with one to three double bonds; and
the targeting ligand is an amino acid chain, optionally cyclic, of 3 to about 50 amino acids.

20. The pharmaceutical composition of claim 1 wherein the encapsulated drug comprises carfilzomib or an HDAC inhibitor, or a combination thereof; the one or more drug-conjugated lipids comprise bortezomib or doxorubicin, or a combination thereof.

21. A pharmaceutical composition comprising liposomes that contain one or more anticancer drugs wherein the liposomes comprise:
a) a phospholipid and optionally a lipid that is not a phospholipid;
b) a pegylated lipid;
c) a peptide-ethylene glycol (EG)-lipid conjugate wherein the peptide is a targeting ligand, and
d) one or more drug-conjugated lipid, encapsulated drugs, or a combination thereof;
wherein the ethylene glycol (EG) segment of the peptide-EG-lipid conjugate is EG6 to about EG36; and the EG segment is conjugated to a lysine moiety wherein the conjugation comprises an amide linkage, and wherein the lysine moiety is conjugated to two $(C_{14}-C_{24})$acyl moieties through amide bonds,
wherein the pegylated lipid has a PEG moiety of PEG750 or greater and the peptide-EG-lipid conjugate comprises a hydrophilic oligolysine chain between the peptide and the EG moiety, wherein the oligolysine comprises 2, 3, 4, or 5 lysine units.

22. The pharmaceutical composition of claim 21 wherein the oligolysine comprises 3 or 4 lysine units.

23. A pharmaceutical composition comprising liposomes that contain one or more anticancer drugs wherein the liposomes comprise:
a) a phospholipid and optionally a lipid that is not a phospholipid;
b) a pegylated lipid;
c) one or more drug-conjugated lipid, encapsulated drugs, or a combination thereof; and
d) a peptide-ethylene glycol (EG)-lipid conjugate of Formula (II), wherein Formula (II) is:

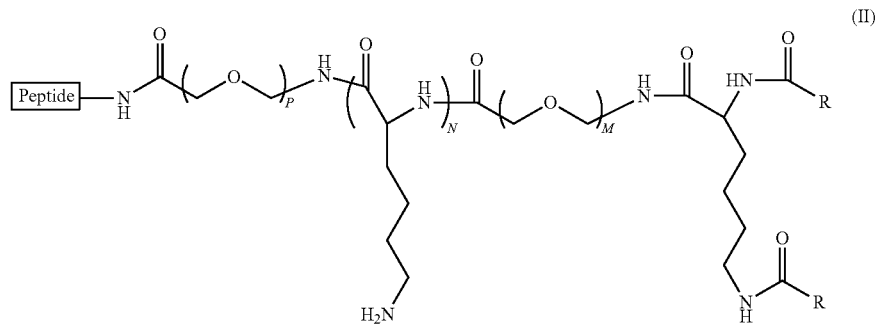

wherein
- M is about 6 to about 36;
- N is 2, 3, 4, 5, or 6;
- P is 1-6;
- each R is independently a $(C_{13}-C_{23})$alkyl, wherein the alkyl is a straight chain or branched, saturated or partially unsaturated with one to three double bonds; and
- Peptide is a targeting ligand comprising an amino acid chain, optionally cyclic, of 3 to about 50 amino acids; or an ion or salt thereof.

24. A method of delivering a drug to a cancer cell in a patient or of treating cancer comprising administering to cell or a subject in need of cancer therapy an effective amount of a pharmaceutical composition of claim 1, wherein the composition comprises a drug-conjugated lipid or encapsulated drug, wherein the drug is effective for killing or inhibiting the cell or treating the cancer, and wherein the composition is taken up by cancer cells, the composition releases the drug in the cells, and the cancer cells are thereby killed or inhibited from growing, thereby treating the cancer.

* * * * *